(12) United States Patent
Connor

(10) Patent No.: US 11,429,151 B2
(45) Date of Patent: Aug. 30, 2022

(54) WEARABLE DEVICES FOR THE WRIST AND/OR ARM WITH MULTIPLE AND MULTI-CONFIGURATION DISPLAYS

(71) Applicant: Robert A. Connor, St. Paul, MN (US)

(72) Inventor: Robert A. Connor, St. Paul, MN (US)

(73) Assignee: Medibotics LLC, St. Paul, MN (US)

( * ) Notice: Subject to any disclaimer, the term of this patent is extended or adjusted under 35 U.S.C. 154(b) by 249 days.

(21) Appl. No.: 16/819,147

(22) Filed: Mar. 15, 2020

(65) Prior Publication Data

US 2020/0218312 A1 Jul. 9, 2020

Related U.S. Application Data

(63) Continuation-in-part of application No. 16/598,514, filed on Oct. 10, 2019, which is a continuation-in-part of application No. 15/294,746, filed on Oct. 16, 2016, now Pat. No. 10,627,861, application No. 16/819,147, which is a continuation-in-part of application No. 15/294,746, filed on Oct. 16, 2016, now Pat. No. 10,627,861, which is a continuation-in-part of application No. 14/623,337, filed on Feb. 16, 2015, now Pat. No. 9,582,035.

(60) Provisional application No. 62/882,560, filed on Aug. 4, 2019, provisional application No. 62/820,337, filed on Mar. 19, 2019, provisional application No. 62/115,691, filed on Feb. 13, 2015, provisional application No. 62/113,423, filed on Feb. 7, 2015, provisional application No. 62/111,163, filed on Feb. 3, 2015, provisional application No. 62/106,856, filed (Continued)

(51) Int. Cl.
*G06F 1/16* (2006.01)
*G06F 3/14* (2006.01)
*A61B 5/00* (2006.01)
*A61B 5/24* (2021.01)
*A61B 5/389* (2021.01)

(52) U.S. Cl.
CPC ............ *G06F 1/1652* (2013.01); *G06F 1/163* (2013.01); *G06F 1/1641* (2013.01); *G06F 3/1446* (2013.01); *A61B 5/0075* (2013.01); *A61B 5/24* (2021.01); *A61B 5/389* (2021.01); *A61B 5/681* (2013.01); *A61B 2562/0219* (2013.01)

(58) Field of Classification Search
CPC .... G06F 3/1446; G06F 1/1649; G06F 1/1624; G06F 1/1641; G06F 1/1652; G06F 1/1622; G06F 1/163; G09G 2300/026; G09G 2380/02; G09G 2356/00; G09G 2354/00; A61B 5/681; A61B 5/24; A61B 2562/0219; A61B 5/0075; A61B 5/389
See application file for complete search history.

(56) References Cited

U.S. PATENT DOCUMENTS 6,035,035 A  3/2000  Firooz
6,883,961 B1 4/2005  Ray
(Continued)

*Primary Examiner* — Yaron Cohen

(57) ABSTRACT

This invention provides innovative designs for wearable devices for the wrist and/or arm which include multiple displays and/or multi-configuration displays. This provides larger overall display size for better human-to-computer interaction, while being relatively comfortable and attractive. Designs with multi-configuration displays enable transition to larger overall display configurations when needed for human-to-computer interaction and more compact display configurations when not in use for such interaction.

1 Claim, 15 Drawing Sheets

Related U.S. Application Data on Jan. 23, 2015, provisional application No. 62/100,217, filed on Jan. 6, 2015, provisional application No. 61/948,124, filed on Mar. 5, 2014, provisional application No. 61/944,090, filed on Feb. 25, 2014.

(56) References Cited

U.S. PATENT DOCUMENTS

| | | |
|---|---|---|
| 6,970,157 B2 | 11/2005 | Siddeeq |
| 7,450,107 B2 | 11/2008 | Radley-Smith |
| 7,460,085 B2 | 12/2008 | Ishii |
| 7,558,057 B1 * | 7/2009 | Naksen .............. G06F 1/1688 361/679.56 |
| 8,149,212 B2 | 4/2012 | Radley-Smith |
| 8,279,716 B1 | 10/2012 | Gossweiler et al. |
| 8,379,488 B1 | 2/2013 | Gossweiler et al. |
| 8,662,362 B1 | 3/2014 | Bastian et al. |
| 8,851,372 B2 | 10/2014 | Zhou et al. |
| 2009/0219788 A1 | 9/2009 | Henley |
| 2015/0029227 A1 * | 1/2015 | Park ...................... G06F 1/1622 345/659 |
| 2015/0109723 A1 | 4/2015 | Holtzman |
| 2015/0113473 A1 | 4/2015 | Otsuka et al. |
| 2015/0338882 A1 | 11/2015 | Yun et al. |
| 2016/0239190 A1 | 8/2016 | Forutanpour et al. |
| 2016/0240154 A1 | 8/2016 | Forutanpour et al. |
| 2016/0246558 A1 | 8/2016 | Prushinskiy et al. |
| 2016/0267310 A1 | 9/2016 | AlNasser et al. |
| 2017/0185170 A1 | 6/2017 | Magi et al. |
| 2018/0120901 A1 | 5/2018 | Jin et al. |
| 2018/0137801 A1 | 5/2018 | An |
| 2019/0243597 A1 | 8/2019 | Hong et al. |
| 2019/0268771 A1 | 8/2019 | Seo et al. |
| 2020/0042037 A1 | 2/2020 | Sun |

* cited by examiner

Device in
first configuration --
bottom and middle displays
recessed in housing under
top display; and band
configured at first
(narrow) width Device in
second configuration --
bottom and middle displays
extended (slid/telescoped)
out from under top display;
and band extended
proximally to second
(wide) width

WEARABLE DEVICES FOR THE WRIST AND/OR ARM WITH MULTIPLE AND MULTI-CONFIGURATION DISPLAYS

CROSS-REFERENCE TO RELATED APPLICATIONS

This application claims the priority benefit of U.S. provisional patent application 62/882,560 filed on 2019 Aug. 4. This application claims the priority benefit of U.S. provisional patent application 62/820,337 filed on 2019 Mar. 19. This application is a continuation in part of U.S. patent application Ser. No. 16/598,514 filed on 2019 Oct. 10. This application is a continuation in part of U.S. patent application Ser. No. 15/294,746 filed on 2016 Oct. 16.

U.S. patent application Ser. No. 16/598,514 was a continuation in part of U.S. patent application Ser. No. 15/294,746 filed on 2016 Oct. 16. U.S. patent application Ser. No. 15/294,746 claimed the priority benefit of U.S. provisional patent application 62/349,277 filed on 2016 Jun. 13. U.S. patent application Ser. No. 15/294,746 was a continuation in part of U.S. patent application Ser. No. 14/951,475 filed on 2015 Nov. 24 which issued as U.S. patent Ser. No. 10/314,492 on 2019 Jun. 11. U.S. patent application Ser. No. 15/294,746 claimed the priority benefit of U.S. provisional patent application 62/245,311 filed on 2015 Oct. 23. U.S. patent application Ser. No. 15/294,746 was a continuation in part of U.S. patent application Ser. No. 14/623,337 filed on 2015 Feb. 16 which issued as U.S. Pat. No. 9,582,035 on 2017 Feb. 28.

U.S. patent application Ser. No. 14/623,337 claimed the priority benefit of U.S. provisional patent application 62/115,691 filed on 2015 Feb. 13. U.S. patent application Ser. No. 14/623,337 claimed the priority benefit of U.S. provisional patent application 62/113,423 filed on 2015 Feb. 7. U.S. patent application Ser. No. 14/623,337 claimed the priority benefit of U.S. provisional patent application 62/111,163 filed on 2015 Feb. 3. U.S. patent application Ser. No. 14/623,337 claimed the priority benefit of U.S. provisional patent application 62/106,856 filed on 2015 Jan. 23. U.S. patent application Ser. No. 14/623,337 claimed the priority benefit of U.S. provisional patent application 62/100,217 filed on 2015 Jan. 6. U.S. patent application Ser. No. 14/623,337 claimed the priority benefit of U.S. provisional patent application 61/948,124 filed on 2014 Mar. 5. U.S. patent application Ser. No. 14/623,337 claimed the priority benefit of U.S. provisional patent application 61/944,090 filed on 2014 Feb. 25.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to wearable computing devices such as smart watches.

Introduction

Wearable devices for a person's wrist and/or arm such as smart watches, smart bands, and smart sleeves have many potential advantages over handheld computing devices such as cell phones and tablets. For example, wearable devices can include sensors which use contact with a person's body to measure selected biometric parameters in a continuous manner which is not possible with handheld devices. Also, wearable devices can be easily transported and accessed, even during activities such as sports and driving. However, current wearable devices designed for the wrist have disadvantages compared to handheld computing devices such as cell phones and tablets. For example, the display for wrist-worn devices is relatively small. The small display size of current wrist-worn devices limits viewing size as well as touch-screen interaction. There is a need for innovative display designs (which are not cumbersome, uncomfortable, and/or downright ugly) which enable larger display sizes for people to interact with wearable devices worn on the arm and/or wrist.

Review of the Relevant Art

There is innovation in the relevant art to try to address the problem of display size in wearable devices for the wrist and/or arm. A first approach to this problem which is disclosed in the prior art is to increase the size of a single display on a wrist and/or arm to roughly the size of a cell phone display. This is basically the—"strap a cellphone to your arm"—strategy. There are some situations in which this approach is acceptable, but generally this approach is too cumbersome, narrow flexible display (such as a flexible display watch band) which encircles a person's wrist. However, even if the technical challenges of creating a truly flexible electronic display can be overcome, a narrow flexible display which encircles a person's wrist requires the person to rotate their arm in order to see different areas around the circumference of the device. This may prove awkward and/or uncomfortable, especially this motion if repeated many times per day. A third approach to this problem is to create an accordion-like display (e.g. a connected series of hinged display screens) which unfolds out from a wrist band and protrudes several inches out into nearby space. This can provide greater display area, but current designs are vulnerable to being snagged and/or broken. Also, current designs can potentially pinch or poke a person's body as the hinged screens are folded or unfolded. The following are some specific examples of innovation in the relevant art.

U.S. Pat. No. 6,035,035 (Firooz, Mar. 7, 2000, "Wrist Mounted Telephone Device") discloses a wrist-mounted telephone device. U.S. Pat. No. 7,460,085 (Ishii, Dec. 2, 2008, "Display Device, Method of Controlling Display Device, Control Program, and Recording Medium") discloses a wearable device with a circumferential display. U.S. Pat. No. 7,558,057 (Naksen et al., Jul. 7, 2009, "Personal Digital Device with Adjustable Interface") discloses a personal digital device with a variable stiffness screen. U.S. Pat. No. 8,851,372 (Zhou et al., Oct. 7, 2014, "Wearable Personal Digital Device With Changeable Bendable Battery and Expandable Display Used as Standalone Electronic Payment Card") discloses a wearable device with methods for enlarging the display space.

U.S. patent application 20090219788 (Henley, Sep. 3, 2009, "Combination Watch and Cell Phone Foldable onto Each Other for Use Around a Wrist of a User") discloses a combination watch and cell phone. U.S. patent application 20150029227 (Park et al., Jan. 29, 2015, "Wrist-Wearable Display Apparatus and Method for Controlling the Same") discloses a wrist-wearable display apparatus with a hidden display part. U.S. patent application 20160240154 (Forutanpour et al., Aug. 18, 2016, "Efficient Operation of Wearable Displays") and 20160239190 (Forutanpour et al., Aug. 18, 2016, "Efficient Display of Content on Wearable Displays") disclose a wearable display devices with a flexible display region which can operate in a wrinkled state. U.S. patent application 20180120901 (Jin et al., May 3, 2018, "Foldable Display Device and Electronic Apparatus with the Same and Control Method of the Same") discloses a foldable display device with a first display screen, a second display screen, and a third display screen. U.S. patent application 20200042037 (Sun, Feb. 6, 2020, "Wearable Display Device") discloses a wearable display device including a flexible screen and a component supporting the flexible screen.

U.S. Pat. No. 6,970,157 (Siddeeq, Nov. 29, 2005, "Wearable Computing, Input, and Display Device") discloses a wearable device with a band wrapped around a wrist, one or more input mechanisms, a display mechanism, and a computing mechanism. U.S. Pat. No. 7,450,107 (Radley-Smith, Nov. 11, 2008, "Bracelet with Information Display and Inputting Capability") and U.S. Pat. No. 8,149,212 (Radley-Smith, Apr. 3, 2012, "Bracelet with Information Display and Inputting Capability") disclose a bracelet with information display and inputting capability comprising twelve segments which are hinged together. U.S. Pat. No. 8,279,716 (Gossweiler et al., Oct. 2, 2012, "Smart-Watch Including Flip Up Display") and U.S. Pat. No. 8,379,488 (Gossweiler et al., Feb. 19, 2013, "Smart-Watch Including Flip Up Display") disclose a smart-watch with a wristband, a base, and a flip up portion. U.S. Pat. No. 8,662,362 (Bastian et al., Mar. 4, 2014, "Apparatus and Method for Supporting and Operating an Electronic Device Upon a User's Forearm") discloses an wearable apparatus for supporting and operating a phone.

U.S. patent application 20150113473 (Otsuka et al., Apr. 23, 2015, "Electronic Device") discloses an electronic device with a touch panel display having an elongated shape. U.S. patent application 20160246558 (Prushinskiy et al., Aug. 25, 2016, "Foldable Display") discloses a foldable display panel including first to fourth regions adjacent to each other. U.S. patent application 20160267310 (AlNasser et al., Sep. 15, 2016, "Wearable Device") discloses a wearable device having a display component, a network component, a computing component, and at least one reader of at least one of a barcode or Radio-frequency identification (RFID). U.S. patent application 20180137801 (An, May 17, 2018, "Flexible Display Device and Displaying Method of Flexible Display Device") discloses a flexible display device with a sensor which obtains user gaze information and determines an activated region on the flexible display based on the user gaze.

U.S. Pat. No. 6,883,961 (Ray, Apr. 26, 2005, "Hinged Electronic Watch") discloses an articulated watch with two juxtaposed cases, each containing an electronic movement, and a connector for mechanically joining the two cases in an articulated manner. U.S. patent application 20150109723 (Holtzman, Apr. 23, 2015, "System for Modular Expansion of Mobile Computer Systems") discloses a mobile computing system in a wristwatch form factor which incorporates a computing element, a display element, and a belt or strap-like band. U.S. patent application 20150338882 (Yun et al., Nov. 26, 2015, "Electronic Device With Foldable Display and Method of Operating the Same") discloses a method of operating an electronic device having a foldable display by displaying information on a screen of the foldable display. U.S. patent application 20170185170 (Magi et al., Jun. 29, 2017, "Flexible Display Sensing") discloses a flexible display detection system to detect movement of a flexible display screen and interpret the movement as a gesture or selection of a device mode. U.S. patent application 20190243597 (Hong et al., Aug. 8, 2019, "Multi-Display Based Device") discloses an electronic device with a first display and a second display. U.S. patent application 20190268771 (Seo et al., Aug. 29, 2019, "Mobile Device of Bangle Type, Control Method Thereof, and UI Display Method") discloses a bangle worn on a user body, a display, a motion sensor configured to detect a motion, and a controller configured to change a screen of the display according to the detected motion.

SUMMARY OF THE INVENTION

This application addresses the above-discussed problem of limited display size for devices which are worn on a person's wrist and/or arm. It discloses innovative designs for wearable devices for the wrist and/or arm which have multiple displays and/or multi-configuration displays. These designs can provide larger overall display size for better human-to-computer interaction, while being relatively comfortable and attractive. These designs include wearable devices with displays with multiple configurations, enabling transition to larger overall display configurations when needed for human-to-computer interaction and more compact display configurations when not in use for human-to-computer interaction. These designs also include wearable devices with multiple displays which are distributed along the longitudinal axis of the dorsal or ventral surface of a person's arm. These designs provide multiple and/or multi-configuration display surfaces (e.g. screens) which provide more surface area for human-to-computer interaction than is available in the prior art, while also being relatively comfortable and not-too-hideous looking.

This invention can be embodied in a wearable computing device comprising: a flexible and/or multi-segmented display which is configured to be worn around at least 50% of the circumference of a person's wrist and/or forearm; a dorsal portion of the flexible and/or multi-segmented display which is configured to be worn on the dorsal side of the person's wrist and/or forearm; a left portion of the flexible and/or multi-segmented display which has: (a) a first configuration in which the left portion is around the left side of the person's wrist, (b) a second configuration in which the left portion pivots, lifts, and/or straightens to extend out to the left of the dorsal portion away from the left side of the person's wrist, and (c) a third configuration in which the left portion rotates around the dorsal portion to extend in a distal or proximal direction relative to the dorsal portion; and a right portion of the flexible and/or multi-segmented display which has: (a) a first configuration in which the right portion is around the right side of the person's wrist, (b) a second configuration in which the right portion pivots, lifts, and/or straightens to extend out to the right of the dorsal portion away from the right side of the person's wrist, and (c) a third configuration in which the right portion rotates around the dorsal portion to extend in a distal or proximal direction relative to the dorsal portion.

DETAILED DESCRIPTION OF THE FIGURES

Figure 1:
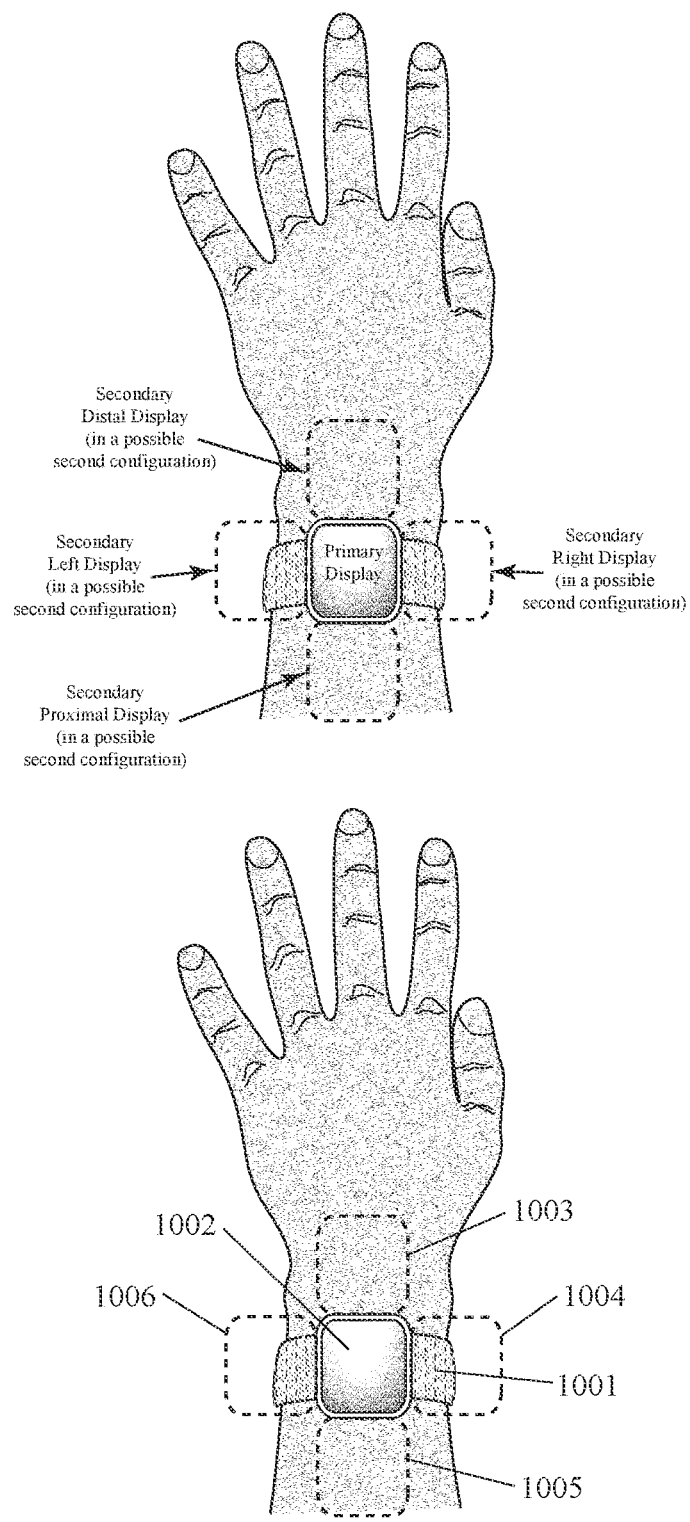
FIG. 1 shows four ways that a wrist-worn device can include a primary display and secondary displays.

FIG. 1 shows an example of four ways in which a wrist-worn computing device with multiple displays and/or a multi-configuration display can comprise: a primary display (screen) located on the dorsal side of a person's wrist; and one or more secondary displays (screens) at one or more different locations relative to the primary display. The upper half of FIG. 1 provides conceptual insight into this example, with written explanations instead of component numbers. The lower half of FIG. 1 shows this same example in conventional patent diagram format with component numbers. These two different perspectives of the same example (in the upper and lower halves of FIG. 1, respectively) combine to provide the reader with a better conceptual understanding of the invention than either perspective alone.

In an example, a secondary display (screen) can be located in a proximal location (e.g. closer to a person's elbow) relative to the primary display. In an example, a secondary display (screen) can be located in a distal location (e.g. farther from the person's elbow) relative to the primary display. In an example, a secondary display (screen) can be located to the left of the primary display. In an example, a secondary display (screen) can be located to the right of the primary display.

The lower half of FIG. 1 shows wrist-worn computing device comprising: a wrist band 1001 worn on a person's wrist; a primary display (screen) 1002 on the dorsal side of the person's wrist; a first possible location 1005 for a secondary display (screen), wherein this first location is proximal (e.g. closer to a person's elbow) relative to the primary display; a second possible location 1003 for a secondary display (screen), wherein this second location is distal (e.g. farther from the person's elbow) relative to the primary display; a third possible location 1006 for a secondary display (screen), wherein this third location is to the left of the primary display; and a fourth possible location 1004 for a secondary display (screen), wherein this fourth location is to the right of the primary display. In an example, a wrist-worn computing device can comprise a primary display (screen) and one or more secondary displays (screens) at one or more of these four secondary display locations. Relevant variations described elsewhere in this disclosure or priority-linked disclosures can also be applied to these examples.

Figure 2:
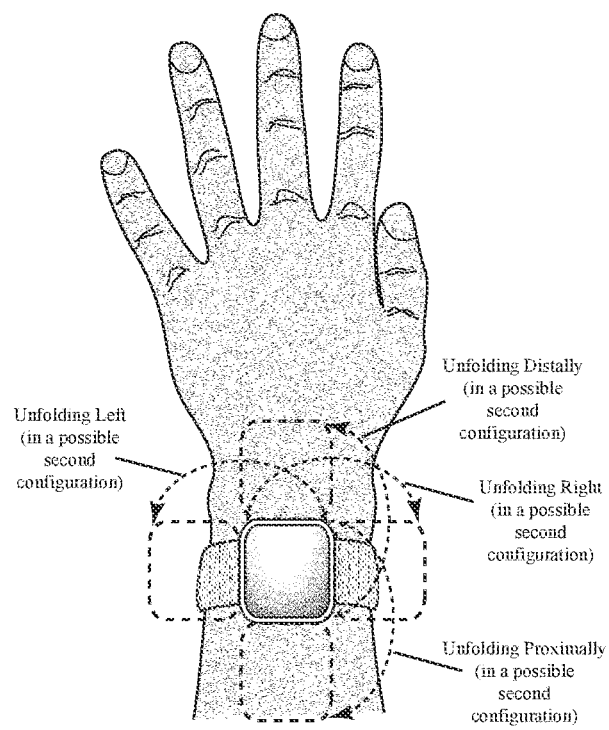
FIG. 2 shows four ways that secondary displays can unfold out from a central location.
Figure 2:
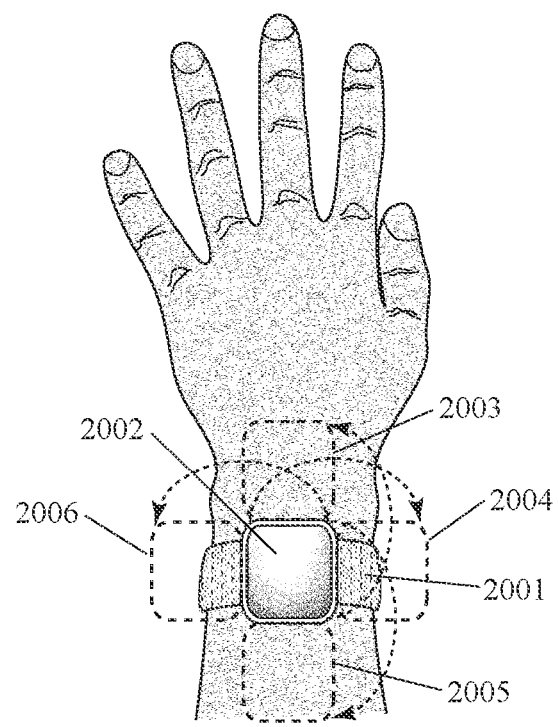

FIG. 2 shows an example of four ways in which one or more secondary displays (screens) can unfold (or "flip") outward from a central location which is aligned with (e.g. above or under) a primary display (screen) or a housing which holds a primary display. The upper half of FIG. 2 provides conceptual insight into this example, with written explanations instead of component numbers. The lower half of FIG. 2 shows this same example in conventional patent diagram format with component numbers. These two different perspectives of the same example (in the upper and lower halves of FIG. 2, respectively) combine to provide the reader with a better conceptual understanding of the invention than either perspective alone.

In an example, a secondary display (screen) can unfold (or "flip") out to a proximal location (e.g. closer to the person's elbow) relative to the primary display. In an example, a secondary display (screen) can unfold out to a distal location (e.g. farther from the person's elbow) relative to the primary display. In an example, a secondary display (screen) can unfold out to a location to the left of the primary display. In an example, a secondary display (screen) can unfold out to a location to the right of the primary display.

The lower half of FIG. 2 shows wrist-worn computing device comprising: a wrist band 2001 worn on a person's wrist; a primary display (screen) 2002 on the dorsal side of the person's wrist; a first possible location 2005 to which a secondary display (screen) can unfold, wherein this first location is proximal (e.g. closer to a person's elbow) relative to the primary display; a second possible location 2003 to which a secondary display (screen) can unfold, wherein this second location is distal (e.g. farther from the person's elbow) relative to the primary display; a third possible location 2006 to which a secondary display (screen) can unfold, wherein this third location is to the left of the primary display; and a fourth possible location 2004 to which a secondary display (screen) can unfold, wherein this fourth location is to the right of the primary display. In an example, a wrist-worn computing device can comprise a primary display (screen) and one or more secondary displays (screens) which unfold (or "flip") out to one or more of these four secondary display locations. Relevant variations described elsewhere in this disclosure or priority-linked disclosures can also be applied to these examples.

Figure 3:
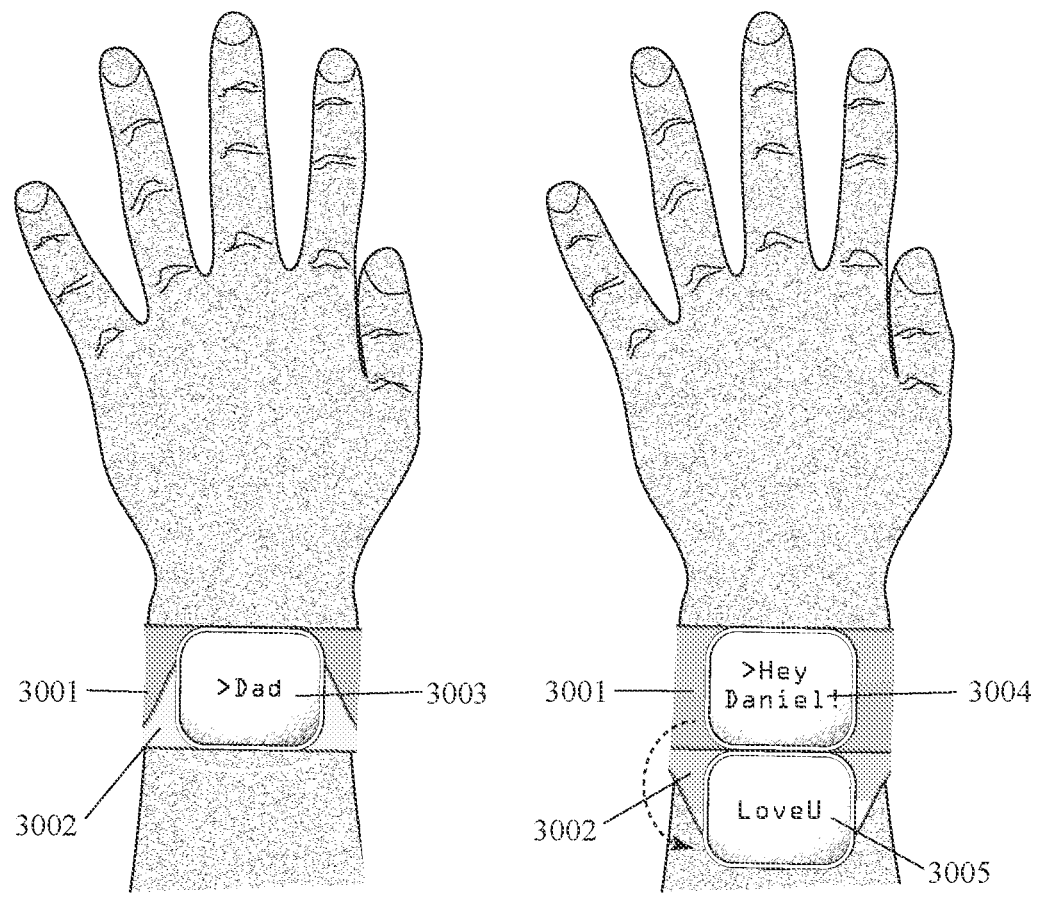
FIG. 3 shows a band which flips open to expose two displays instead of one.

FIG. 3 shows two sequential views of an example of a wrist-worn computing device with a multi-configuration display comprising: (a) primary attachment member (e.g. wrist band) 3001, wherein this primary attachment member is configured to attach the device to a person's wrist and/or forearm by encircling at least 50% of the circumference of the person's wrist and/or forearm; (b) a folding attachment member 3002, wherein this folding attachment member has a first configuration in which it overlaps the primary attachment member by a first amount, wherein this folding attachment member has a second configuration in which it overlaps primary attachment member by a second amount, wherein the second amount is less than the first amount, and wherein the folding attachment member is moved from the first configuration to the second configuration by rotation of the folding attachment member relative to the primary attachment member; (c) a first display 3003, wherein this first display is on the exterior surface of the device and visible to the person when the folding attachment member is in the first configuration; (d) a second display 3004, wherein this second display is on the exterior surface of the device and visible to the person when the folding attachment member is in the second configuration; and (e) a third display 3005, wherein this third display is on the exterior surface of the device and visible to the person when the folding attachment member is in the second configuration.

The left portion of FIG. 3 shows this device when folding attachment member 3002 is in the first configuration. The right portion of FIG. 3 shows this device when folding attachment member 3002 has been moved into the second configuration. This movement is symbolically represented by a dotted-line arrow in the right portion of FIG. 3. In the right portion of FIG. 3, folding attachment member 3002 has been moved from the first configuration to the second configuration by being rotated around a side-to-side axial joint which connects the folding attachment member to the primary attachment member. In this example, the axial joint is along the surface of the person's wrist and/or forearm and the edge of the folding attachment member which is opposite to the axial joint is rotated away from the surface of the wrist and/or forearm during the transition from the first configuration to the second configuration. In the right portion of FIG. 3, folding attachment member 3002 has been moved manually (e.g. by the person) from the first configuration to the second configuration. In another example, a folding attachment can be automatically moved from the first configuration to the second configuration by an actuator which is part of the device.

In the example shown in FIG. 3, the device can be said to have been "flipped open" when folding attachment member 3002 has been moved from the first configuration to the second configuration. In this example, folding attachment member 3002 completely overlaps primary attachment member 3001 in the first configuration and does not overlap primary attachment member 3001 at all in the second configuration. In this example, the folding attachment member lies flat against the surface of the person's wrist and/or forearm in the second configuration. In this example, folding attachment member 3002 "flips open" in a proximal direction—moving closer to the person's elbow in the transition from the first configuration to the second configuration. In another example, folding attachment member 3002 could "flip open" in a distal direction—moving away from the person's elbow in the transition from the first configuration to the second configuration.

In an example, primary attachment member 3001 can be a band, strap, chain, bracelet, or bangle. In an example, primary attachment member 3001 can be a flexible and/or elastic band, strap, mesh, cuff, or chain which spans the entire circumference of the person's wrist and/or forearm. In an example, primary attachment member 3001 can be sufficiently flexible and/or elastic that it can be slipped over the hand onto the wrist and/or forearm. In an example, primary attachment member 3001 can be a band, strap, or chain which further comprises a buckle, clasp, clip, hook, hook-and-eye material, pin, latch, button, and/or zipper which fastens it around the circumference of the person's wrist and/or forearm. In an example, primary attachment member 3001 can be a bracelet or bangle. In an example, primary attachment member 3001 can be sufficiently rigid and/or resiliently-flexible that it holds the device on the person's wrist and/or forearm even though it does not span the entire circumference of the person's wrist and/or forearm.

In an example, folding attachment member 3002 can be a band, strap, or protrusion. In an example, folding attachment member 3002 can be a flexible and/or elastic band, strap, or protrusion which spans less of the circumference of the person's wrist and/or forearm than is spanned by primary attachment member 3001. In an example, folding attachment member 3002 may span only the upper (or frontal) surface of the person's wrist and/or arm. In an example, a folding attachment member can have arcuate edges which connect to the lateral sides of the second display. Such arcuate edges can reduce snagging of the second display in the second configuration.

In an example, at least 75% of folding attachment member 3002 overlaps primary attachment member 3001 in the first configuration. In an example, at least 90% of folding attachment member 3002 overlaps primary attachment member 3001 in the first configuration. In an example, folding attachment member 3002 completely overlaps primary attachment member 3001 in the first configuration. In an example, less than 75% of folding attachment member 3002 overlaps primary attachment member 3001 in the second configuration. In an example, less than 10% of folding attachment member 3002 overlaps primary attachment member 3001 in the second configuration. In an example, folding attachment member 3002 does not overlap primary attachment member 3001 at all in the second configuration.

In an example, a folding attachment member can be connected to a primary attachment member by a side-to-side (lateral) axial joint. In an example, the surface area of a person's wrist or arm which is covered by the device can be increased when the folding attachment member is moved from the first configuration to the second configuration. This enables the outward-facing surface device to be smaller when only the first display is in use and larger when the second and third displays are in use. In an example the folding attachment member can be parallel to the plane of the primary attachment member in the first configuration. In an example the folding attachment member can be parallel to the plane of the primary attachment member in both the first configuration and second configuration. In an example, the folding attachment member may temporarily not be parallel to the plane of the primary attachment member during the transition from the first configuration to the second configuration.

In an example, a display can be a computer display screen. In an example, a display can have a cross-sectional shape which is selected from the group consisting of: rectangular with rounded vertexes, hexagonal with rounded vertexes, square, rectangular, hexagonal, circular, elliptical, and oblong. In an example, the second and third displays can be centrally aligned along the same proximal-to-distal axis of the person's wrist and/or forearm. In an example, a display can have a flat display surface. In an example, a display can be a touch screen which responds to finger movements. In this example, the first, second, and third displays are separate components. In another example, the first and third displays can be top and bottom views of the same component. In another example, the device may not have a first display and only have the second and third displays.

In an example, the first display can display a summary of the information which is displayed in more detail on the second and third displays. In an example, the second and third displays can display two different sections of the same text content. In an example, the second and third displays can display two different sections of the same image content. In an example, the second and third displays can display text and image, respectively, from the same multi-media content.

In an example, a display can display information with a proximal-to-distal or distal-to-proximal orientation. In an example, a display can display information with a lateral orientation. In an example, the device can automatically change the radial orientation of information on a display based on the orientation and/or movement of the device as detected by a gyroscope and/or motion sensor which is incorporated into the device. In an example, the orientation of information on a display can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

In an example, a wrist-worn computing device can further comprise one or more sensors. In an example, a sensor can be a multi-axial accelerometer. In an example, a sensor can be a gyroscope. In an example, a sensor can be a light energy sensor. In an example, a sensor can be a spectroscopic sensor which collects data concerning the spectrum of light reflected from and/or transmitted through tissue of the person's wrist and/or forearm. In an example, a sensor can be an electromagnetic energy sensor. In an example, a sensor can measure the resistance, impedance, and/or conductivity of tissue of the person's wrist and/or forearm with respect to the transmission of electromagnetic energy. In an example, a sensor can measure electromagnetic energy emitted from muscles and/or nerves in the person's wrist and/or forearm. In an example, a sensor can be a capacitive electromagnetic energy sensor.

In an example, a sensor can be an environmental light energy sensor. In an example, a display can have a first display mode which requires less energy and a second display mode which requires more energy. In an example, a display can automatically switch from the first display mode to the second display mode when the second display mode is required for the person to be able to see information on the display. In an example, the device can switch the display from the first mode to the second mode when there is a high level of environmental light energy and the display would not be visible in bright light in the first display mode. In an example, the device can switch the display from the first mode to the second mode when there is a low level of environmental light energy and the display would not be visible in dim light (or darkness) in the first display mode.

In an example, this device can change one or more displays from a first (lower energy) display mode to a second (higher energy) display mode, or vice versa, based on data from one or more motion and/or inertial sensors which are incorporated into the device or with which the device is in wireless communication. In an example, when a motion and/or inertial sensor indicates a first level of movement of the device or a first orientation of the device, then the assumption is that the person is not looking at the device and the device sets the display to the first (lower energy) display mode. In an example, when a motion and/or inertial sensor indicates a second level of movement of the device or a second orientation of the device, then the assumption is that the person may be looking at the device and the device sets the display to the second (higher energy) display mode.

In an example, this device can be part of a multi-device system which includes other locations on a person's body, such as the person's head or torso. In an example, this device can be in communication with a motion and/or inertial sensor which is located elsewhere on the person's body so that the relative motion or relative orientation of the device (relative to the rest of the person's body) can be monitored. Measuring the relative motion or orientation of the device (e.g. relative to the rest of the person's body) rather than absolute motion or position of the device (e.g. relative to the earth) can help to factor out changes in motion or orientation which are due to being in a car, elevator, or airplane. Even though the absolute position or orientation of a device might be changing rapidly in a car, elevator, or airplane, the relative position of the device (relative to the rest of the person) may be stable and the person may wish see the display. Relevant variations described elsewhere in this disclosure or priority-linked disclosures can also be applied to these examples.

Figure 4:
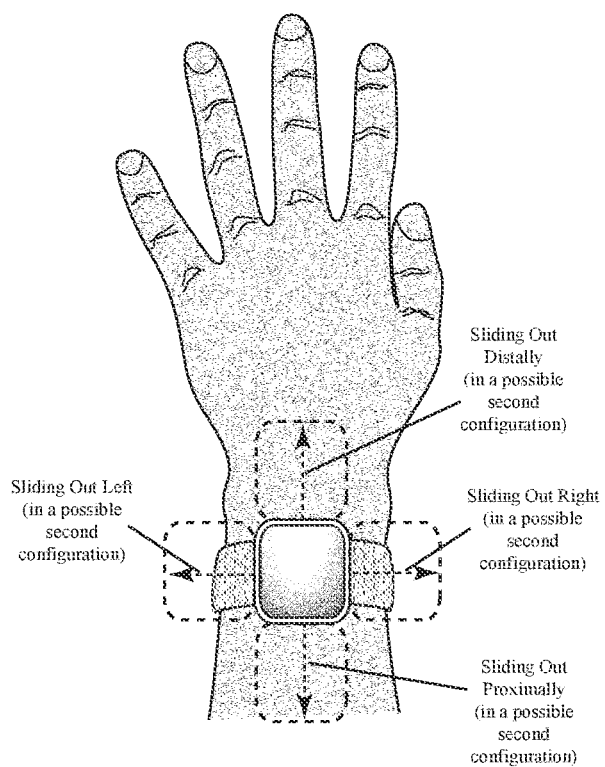
FIG. 4 shows four ways that secondary displays can slide out from a central location.
Figure 4:
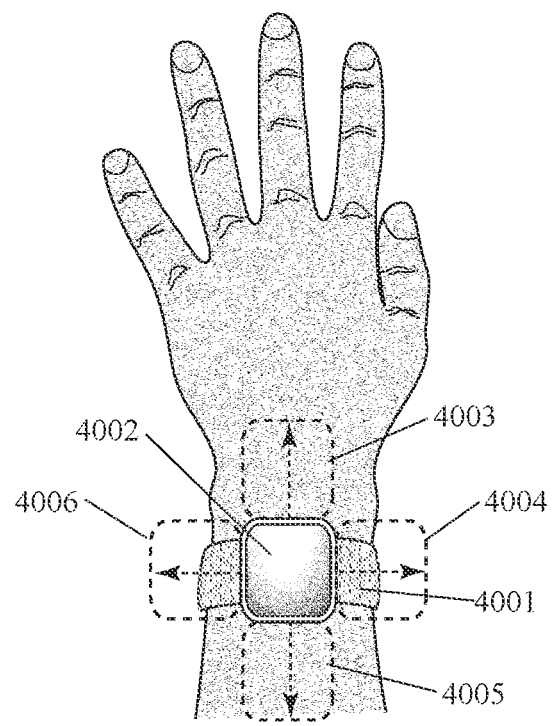

FIG. 4 shows an example of four ways in which one or more secondary displays (screens) can slide (laterally) outward from a central location which is aligned with (e.g. above or under) a primary display (screen) or a housing which holds a primary display. The upper half of FIG. 4 provides conceptual insight into this example, with written explanations instead of component numbers. The lower half of FIG. 4 shows this same example in conventional patent diagram format with component numbers. These two different perspectives of the same example (in the upper and lower halves of FIG. 4, respectively) combine to provide the reader with a better conceptual understanding of the invention than either perspective alone.

In an example, a secondary display (screen) can slide (laterally) out from under a primary display (and/or can slide out from inside a housing which holds a primary display) to a proximal location (e.g. closer to the person's elbow) relative to the primary display. In an example, a secondary display (screen) can slide out from under a primary display (and/or can slide out from inside a housing which holds a primary display) to a distal location (e.g. farther from the person's elbow) relative to the primary display. In an example, a secondary display (screen) can slide out from under a primary display (and/or can slide out from inside a housing which holds a primary display) to a location to the left of the primary display. In an example, a secondary display (screen) can slide out from under a primary display (and/or can slide out from inside a housing which holds a primary display) to a location to the right of the primary display.

The lower half of FIG. 4 shows wrist-worn computing device comprising: a wrist band 4001 worn on a person's wrist; a primary display (screen) 4002 on the dorsal side of the person's wrist; a first possible location 4005 to which a secondary display (screen) can slide out, wherein this first location is proximal (e.g. closer to a person's elbow) relative to the primary display; a second possible location 4003 to which a secondary display (screen) can slide out, wherein this second location is distal (e.g. farther from the person's elbow) relative to the primary display; a third possible location 4006 to which a secondary display (screen) can slide out, wherein this third location is to the left of the primary display; and a fourth possible location 4004 to which a secondary display (screen) can slide out, wherein this fourth location is to the right of the primary display. In an example, a wrist-worn computing device can comprise a primary display (screen) and one or more secondary displays (screens) which slide (laterally) out to one or more of these four secondary display locations. Relevant variations described elsewhere in this disclosure or priority-linked disclosures can also be applied to these examples.

Figure 5:
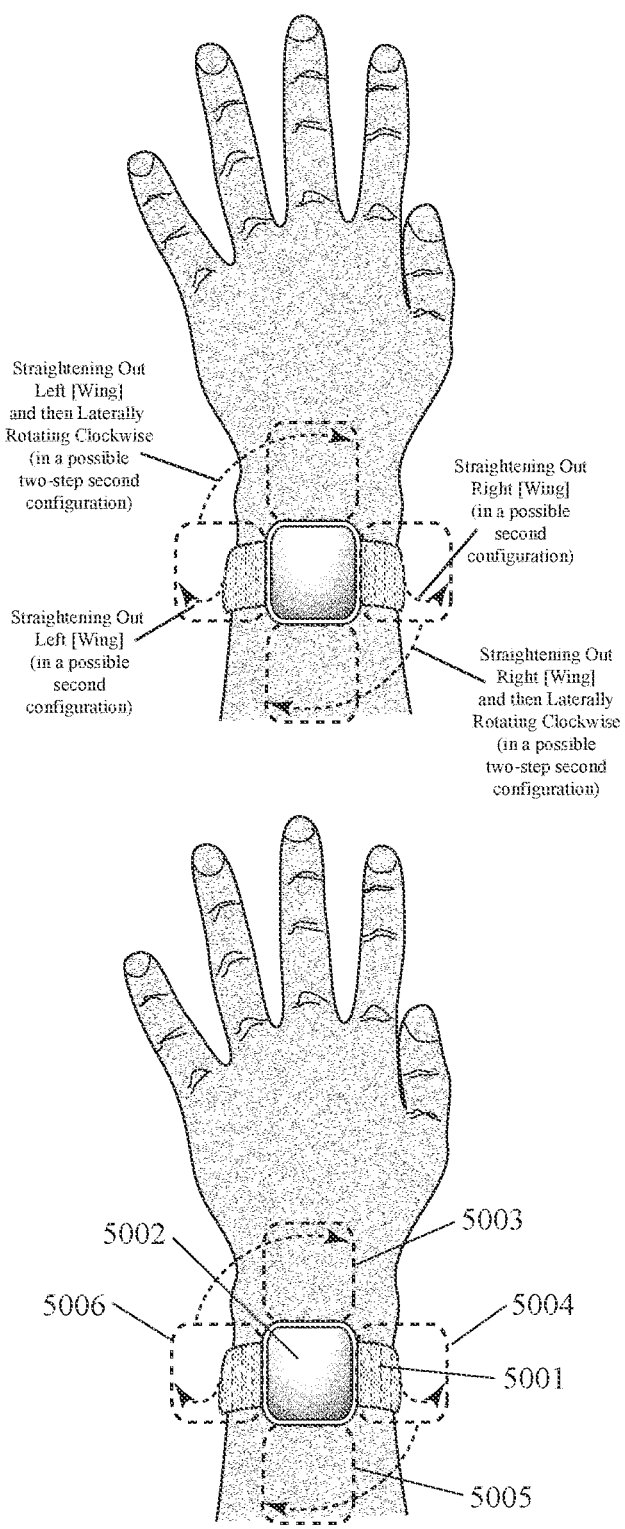
FIGS. 5 and 6 shows how secondary displays can move from a first configuration in which they curve around lateral sides of a wrist band to a second configuration in which they extend straight out from the wrist band in proximal and distal directions.

FIG. 5 shows an example of ways in which a secondary display (screen) can be moved from a first configuration in which it spans (e.g. curves around) a lateral (e.g. right or left) portion of the circumference of a wrist band to a second configuration in which it extends straight outward from the wrist band in proximal or distal direction. The upper half of FIG. 5 provides conceptual insight into this example, with written explanations instead of component numbers. The lower half of FIG. 5 shows this same example in conventional patent diagram format with component numbers. These two different perspectives of the same example (in the upper and lower halves of FIG. 5, respectively) combine to provide the reader with a better conceptual understanding of the invention than either perspective alone.

In an example, a secondary display (screen) can be moved from a first configuration to a second configuration by: pivoting, lifting, and/or straightening a ventral portion of the secondary display away from the circumference of a wrist band; and then rotating the ventral portion of the secondary display (90 degrees) around a primary display (screen) to a location which is proximal or distal location relative to a primary display. In an example, a secondary display (screen) can be a flexible or bendable display which is arcuate in its first configuration and substantially planar (e.g. flat) in its secondary configuration. This concept can also be applied to a connected series of displays (screens) which can be moved from a first configuration curving around a lateral portion of a band to a second configuration extending straight out from the dorsal side of the band in a proximal or distal direction. In an example, a secondary display or connected series of displays can be attached to a rotating housing or to a rotating ring or bezel around a housing.

The lower half of FIG. 5 shows wrist-worn computing device comprising: a wrist band 5001 worn on a person's wrist; a primary display (screen) 5002 on the dorsal side of the person's wrist; a first secondary display (screen), wherein a ventral portion of the first secondary display is—pivoted, lifted, and/or straightened away from the circumference of the wrist band to a first location 5006 to the left of the primary display; and then rotated around the primary display (screen) to a second location 5003 which is distal relative to the primary display; and a second secondary display (screen), wherein a ventral portion of the second secondary display is—pivoted, lifted, and/or straightened away from the circumference of the wrist band to a third location 5004 to the right of the primary display; and then rotated around the primary display (screen) to a fourth location 5005 which is proximal relative to the primary display.

In another example, a wrist-worn computing device comprising: a wrist band worn on a person's wrist; a primary display (screen) on the dorsal side of the person's wrist; a first secondary display (screen), wherein a ventral portion of the first secondary display is—pivoted, lifted, and/or straightened away from the circumference of the wrist band to a first location to the right of the primary display; and then rotated around the primary display (screen) to a second location which is distal relative to the primary display; and a second secondary display (screen), wherein a ventral portion of the second secondary display is—pivoted, lifted, and/or straightened away from the circumference of the wrist band to a third location to the left of the primary display; and then rotated around the primary display (screen) to a fourth location which is proximal relative to the primary display.

In another example, a wrist-worn computing device comprising: a wrist band worn on a person's wrist; a primary display (screen) on the dorsal side of the person's wrist; a secondary display (screen), wherein a ventral portion of the secondary display is—pivoted, lifted, and/or straightened away from the circumference of the wrist band to a first location to the right of the primary display; and then rotated around the primary display (screen) to a second location which is distal relative to the primary display. In another example, a wrist-worn computing device comprising: a wrist band worn on a person's wrist; a primary display (screen) on the dorsal side of the person's wrist; a secondary display (screen), wherein a ventral portion of the secondary display is—pivoted, lifted, and/or straightened away from the circumference of the wrist band to a first location to the left of the primary display; and then rotated around the primary display (screen) to a second location which is distal relative to the primary display.

In another example, a wrist-worn computing device comprising: a wrist band worn on a person's wrist; a primary display (screen) on the dorsal side of the person's wrist; a secondary display (screen), wherein a ventral portion of the secondary display is—pivoted, lifted, and/or straightened away from the circumference of the wrist band to a first location to the right of the primary display; and then rotated around the primary display (screen) to a second location which is proximal relative to the primary display. In another example, a wrist-worn computing device comprising: a wrist band worn on a person's wrist; a primary display (screen) on the dorsal side of the person's wrist; a secondary display (screen), wherein a ventral portion of the secondary display is—pivoted, lifted, and/or straightened away from the circumference of the wrist band to a first location to the left of the primary display; and then rotated around the primary display (screen) to a second location which is proximal relative to the primary display. Relevant variations described elsewhere in this disclosure or priority-linked disclosures can also be applied to these examples.

Figure 6:
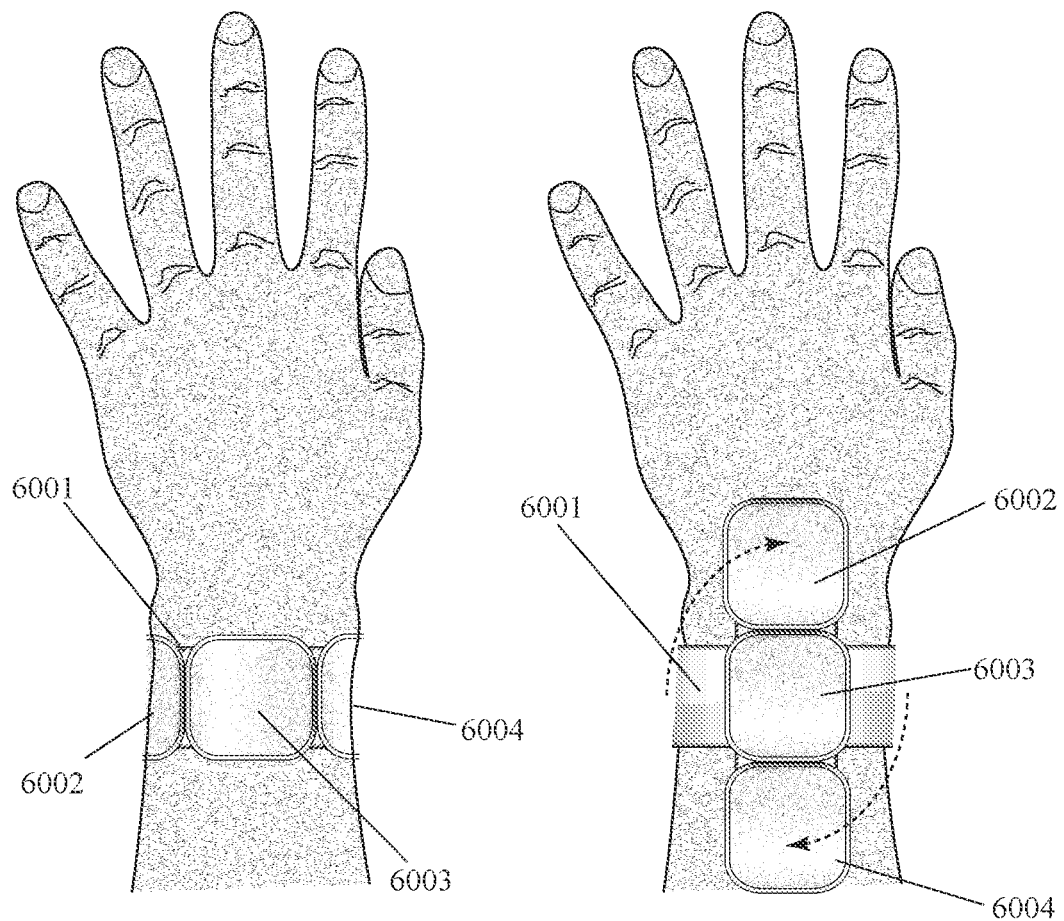

FIG. 6 shows two sequential views of an example of a wrist-worn computing device with a multi-configuration display comprising: (a) an arcuate attachment member (e.g. wrist band) 6001 which is configured to span at least 50% of the circumference of the person's wrist and/or forearm, wherein a central longitudinal axis is defined as a line along the upper (ventral) surface of the person's forearm, from the elbow to the hand, which is equidistant from the lateral sides of the person's forearm; (b) a first display 6002, wherein this first display has a first configuration in which its centroid is a first distance from the central longitudinal axis, wherein this first display has a second configuration in which its centroid is a second distance from the central longitudinal axis, and wherein the second distance is less than the first distance; (c) a second display 6003; and (d) a third display 6004, wherein this third display has a third configuration in which its centroid is a third distance from the central longitudinal axis, wherein this third display has a fourth configuration in which its centroid is a fourth distance from the central longitudinal axis, wherein the fourth distance is less than the third distance, and wherein the third display is moved from the third configuration to the fourth configuration when the first display is moved from the first configuration to the second configuration.

The left portion of FIG. 6 shows this device at a first point in time when the first and third displays are in their first and third configurations, respectively. In the left portion of FIG. 6, the arcuate attachment member and the three displays are all aligned around the circumference of the person's wrist and/or forearm in a minimally-obtrusive manner. However, only the second display is located on the flat portion of the upper surface of the person's wrist and/or forearm. The right portion of FIG. 6 shows this device at a second point in time after the first and third displays have been moved into their second and fourth configurations, respectively. In an example, this movement can be done manually by the person. In an example, this movement can be done automatically by an actuator which is included in the device. In the right portion of FIG. 6, the arcuate attachment member is still aligned around the circumference of the person's wrist and/or forearm, but the three displays have been rotated into alignment with the central longitudinal axis to create more visible display area on the flat portion of the upper surface of the person's wrist and/or forearm. This design enables the device to transition, when needed, from a less-obtrusive configuration with less display screen area on the upper surface of the forearm to a more-intrusive configuration with more display screen area on the upper surface of the forearm.

In this example, this device has multiple displays which are oriented in a partially-circumferential manner around a person's wrist and/or forearm in one configuration and are oriented along a central longitudinal axis of the upper surface of the person's forearm in another configuration. In this example, the multiple displays are moved from one configuration to another by being rotated around a central point on an arcuate attachment member. In this example, the left and right side members of a three member sequence of displays are attached to a primary display that rotates. In an example, the displays can be connected by joints or hinges so that they are not coplanar when they are oriented circumferentially around the person's wrist and/or forearm, but are coplanar when they are rotated onto the upper surface of the person's wrist and/or forearm. In an example, these joints or hinges can be spring loaded to bias the displays against the surface of the wrist and/or forearm in either configuration. In this example, there are three displays in a sequence of displays which is rotated from a circumferential orientation to a central longitudinal orientation when greater display area is needed. In another example, a device may have two displays which are rotated from a circumferential orientation to a central longitudinal orientation when greater display area is needed.

In an example, a wearable computing device can comprise: a wrist band which is configured to be worn around a person's wrist; a primary display which is configured to be worn on the dorsal side of the person's wrist; a first secondary display, wherein a ventral portion of the first secondary display is (a) pivoted, lifted, and/or straightened away from the circumference of the wrist band to a first location to the left or right of the primary display and then (b) rotated around the primary display to a second location which is distal or proximal relative to the primary display; and a second secondary display, wherein a ventral portion of the second secondary display is (a) pivoted, lifted, and/or straightened away from the circumference of the wrist band to a third location to the right or left of the primary display and then (b) rotated around the primary display (screen) to a fourth location which is proximal or distal relative to the primary display.

In an example, a wearable computing device can comprise: a flexible and/or multi-segmented display which is configured to be worn around at least 50% of the circumference of a person's wrist and/or forearm; a dorsal portion of the flexible and/or multi-segmented display which is configured to be worn on the dorsal side of the person's wrist and/or forearm; a left portion of the flexible and/or multi-segmented display which has: (a) a first configuration in which the left portion is around the left side of the person's wrist, (b) a second configuration in which the left portion pivots, lifts, and/or straightens to extend out to the left of the dorsal portion away from the left side of the person's wrist, and (c) a third configuration in which the left portion rotates around the dorsal portion to extend in a distal or proximal direction relative to the dorsal portion; and a right portion of the flexible and/or multi-segmented display which has: (a) a first configuration in which the right portion is around the right side of the person's wrist, (b) a second configuration in which the right portion pivots, lifts, and/or straightens to extend out to the right of the dorsal portion away from the right side of the person's wrist, and (c) a third configuration in which the right portion rotates around the dorsal portion to extend in a distal or proximal direction relative to the dorsal portion.

In an example, a wearable computing device can comprise: a band which is configured to be worn around at least 50% of the circumference of a person's wrist and/or forearm; a dorsal display which is configured to be worn on the dorsal side of the person's wrist and/or forearm; a left display which has: (a) a first configuration in which the left display is worn on the left side of the person's wrist, (b) a second configuration in which the left display pivots, lifts, and/or straightens to extend out to the left of the dorsal display away from the left side of the person's wrist, and (c) a third configuration in which the left display rotates around the dorsal display to extend in a distal or proximal direction relative to the dorsal display; and a right display which has: (a) a first configuration in which the right display is worn on the right side of the person's wrist, (b) a second configuration in which the right display pivots, lifts, and/or straightens to extend out to the right of the dorsal display away from the right side of the person's wrist, and (c) a third configuration in which the right display rotates around the dorsal display to extend in a distal or proximal direction relative to the dorsal display. Relevant variations described elsewhere in this disclosure or priority-linked disclosures can also be applied to these examples.

In an example, a display can be a computer display screen. In an example, a display can have a cross-sectional shape which is selected from the group consisting of: rectangular with rounded vertexes, hexagonal with rounded vertexes, square, rectangular, hexagonal, circular, elliptical, and oblong. In an example, multiple displays can be centrally aligned along the same proximal-to-distal axis of the person's wrist and/or forearm. In an example, a display can have a flat display surface. In an example, a display can be a touch screen which responds to finger movements. In an example, different displays can display different sections of the same text content. In an example, different displays can display different sections of the same image content. In an example, the different displays can display text and image, respectively, from the same multi-media content.

In an example, an arcuate attachment member can be a band, bracelet, armlet, bangle, coil, band, strap, chain, or cuff. In an example, the lower ends of an attachment member can be attached around a person/s wrist and/or forearm by a buckle, clasp, clip, hook, hook-and-eye material, pin, latch, button, and/or zipper. In an example, an attachment member can be slipped over a person's hand to fit around a person/s wrist and/or forearm. Relevant variations described elsewhere in this disclosure or priority-linked disclosures can also be applied to these examples.

Figure 7:
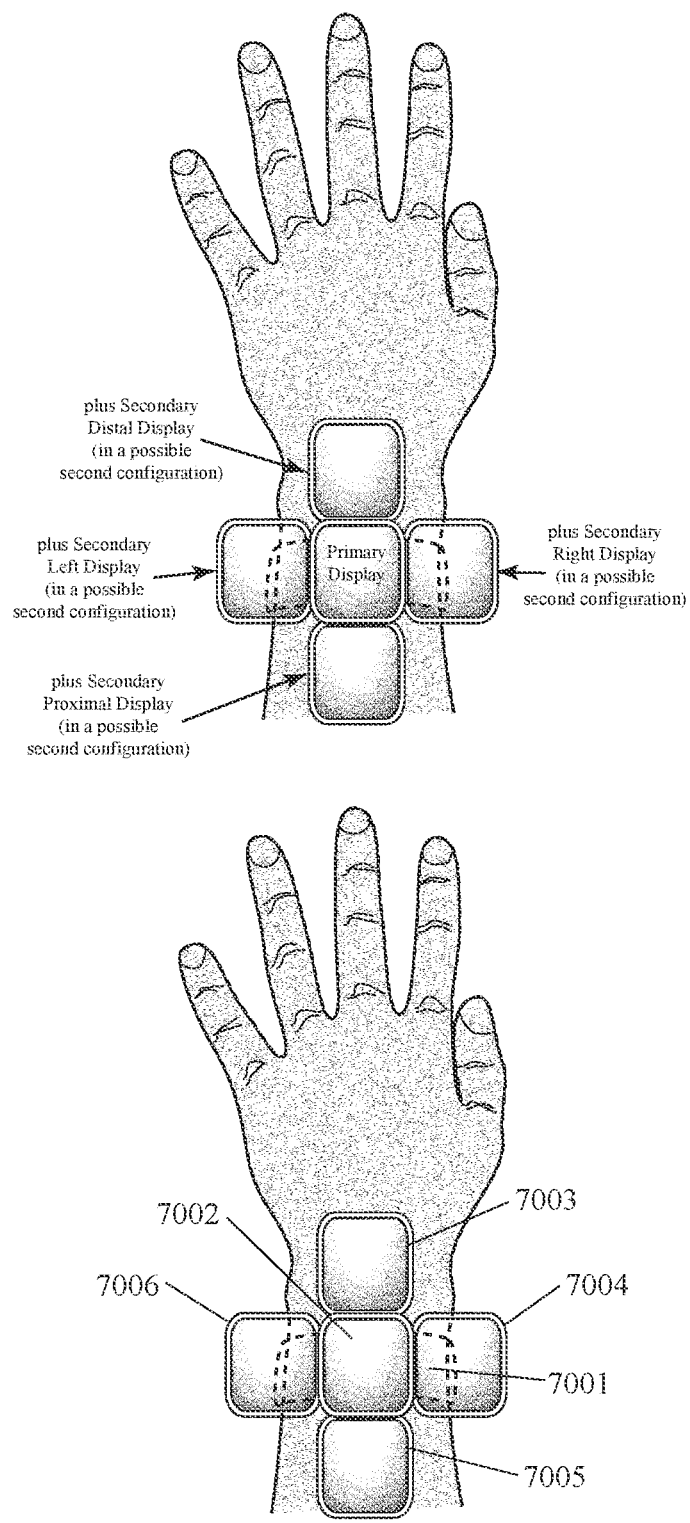
FIG. 7 shows four locations for secondary displays around a primary display.

FIG. 7 shows an example of ways in which a wrist-worn computing device with multiple displays and/or a multi-configuration display can comprise: a primary display (screen) located on the dorsal side of a person's wrist; and one or more secondary displays (screens) in one or more different locations relative to the primary display. The upper half of FIG. 7 provides conceptual insight into this example, with written explanations instead of component numbers. The lower half of FIG. 7 shows this same example in conventional patent diagram format with component numbers. These two different perspectives of the same example (in the upper and lower halves of FIG. 7, respectively) combine to provide the reader with a better conceptual understanding of the invention than either perspective alone.

In an example, a secondary display (screen) can be located in a proximal location (e.g. closer to a person's elbow) relative to the primary display. In an example, a secondary display (screen) can be located in a distal location (e.g. farther from the person's elbow) relative to the primary display. In an example, a secondary display (screen) can be located to the left of the primary display. In an example, a secondary display (screen) can be located to the right of the primary display.

The lower half of FIG. 7 shows wrist-worn computing device comprising: a wrist band 7001 worn on a person's wrist; a primary display (screen) 7002 on the dorsal side of the person's wrist; a first secondary display (screen) 7005 which is proximal (e.g. closer to a person's elbow) relative to the primary display; a second secondary display (screen) 7003 which is distal (e.g. farther from the person's elbow) relative to the primary display; a third secondary display (screen) 7006 which is to the left of the primary display; and a fourth secondary display (screen) 7004 which is to the right of the primary display.

In an example, a wrist-worn computing device can comprise: a wrist band worn on a person's wrist; a primary display (screen) on the dorsal side of the person's wrist; and a secondary display (screen) which is proximal (e.g. closer to a person's elbow) relative to the primary display. In an example, a wrist-worn computing device can comprise: a wrist band worn on a person's wrist; a primary display (screen) on the dorsal side of the person's wrist; and a secondary display (screen) which is distal (e.g. farther from the person's elbow) relative to the primary display. In an example, a wrist-worn computing device can comprise: a wrist band worn on a person's wrist; a primary display (screen) on the dorsal side of the person's wrist; and a secondary display (screen) which is to the left of the primary display. In an example, a wrist-worn computing device can comprise: a wrist band worn on a person's wrist; a primary display (screen) on the dorsal side of the person's wrist; and a secondary display (screen) which is to the right of the primary display. Relevant variations described elsewhere in this disclosure or priority-linked disclosures can also be applied to these examples.

Figure 8:
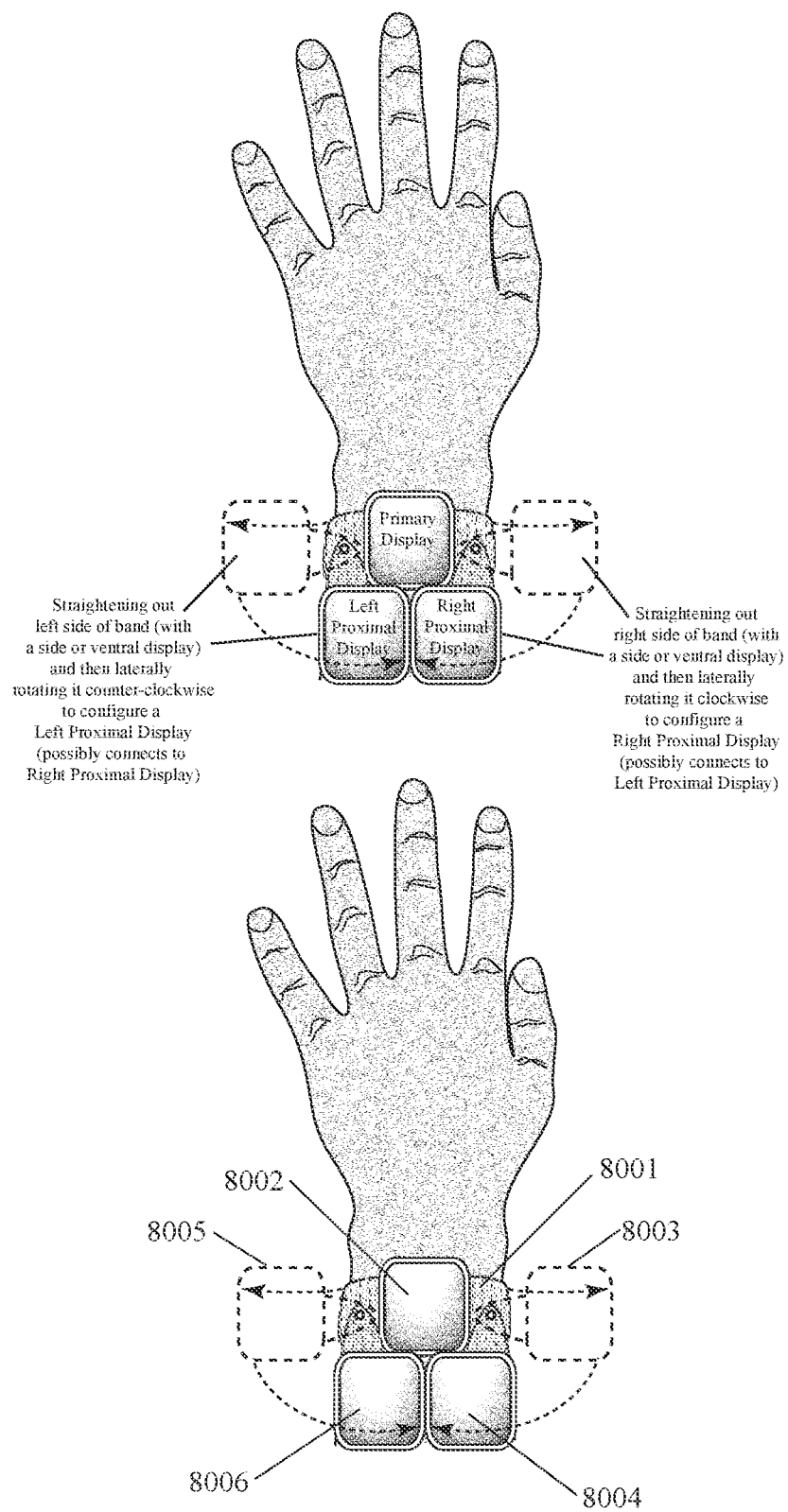
FIG. 8 shows a right display which is attached by a first rotational joint to the right-dorsal quadrant of a band circumference and a left display which is attached by a second rotational joint to the left-dorsal quadrant of the band circumference.

FIG. 8 shows an example of a wrist-worn computing device with a multi-configuration display comprising: a band which is worn on a person's wrist and/or lower arm; a right display (screen) which is attached by a first rotational joint to the right-dorsal quadrant of the band circumference; a left display (screen) which is attached by a second rotational joint to the left-dorsal quadrant of the band circumference; wherein the device has a first configuration in which the right and left displays lie along the circumference of the band; wherein the device has a second configuration in which the right and left displays extend out (like "wings") from the band in lateral (right and left) directions, respectively; wherein the device has a third configuration in which the right and left displays both extend out from the band in a proximal direction; wherein the right and left displays are changed from the first configuration to the second configuration by pivoting, bending, or straightening their ventral portions away from the circumference of the band; wherein the right and left displays are changed from the second configuration to the third configuration by rotating them (90 degrees) around the first and second rotational joints, respectively. The upper half of FIG. 8 provides conceptual insight into this example, with written explanations instead of component numbers. The lower half of FIG. 8 shows this same example in conventional patent diagram format with component numbers. These two different perspectives of the same example (in the upper and lower halves of FIG. 8, respectively) combine to provide the reader with a better conceptual understanding of the invention than either perspective alone.

The lower half of FIG. 8 shows a wrist-worn computing device with a multi-configuration display comprising: a band 8001 which is worn on a person's wrist and/or lower arm; a primary display (screen) 8002 on the dorsal side of the person's wrist; a right display (screen) 8004 which is attached by a first rotational joint to the right-dorsal quadrant of the band circumference; a left display (screen) 8006 which is attached by a second rotational joint to the left-dorsal quadrant of the band circumference; wherein the device has a first configuration in which the right and left displays lie along the circumference of the band; wherein the device has a second configuration in which the right and left displays extend out (like "wings") from the band in lateral (right and left) directions, at locations 8003 and 8005, respectively; wherein the device has a third configuration in which the right and left displays both extend out from the band in a proximal direction; wherein the right and left displays are changed from the first configuration to the second configuration by pivoting, bending, or straightening their ventral portions away from the circumference of the band; wherein the right and left displays are changed from the second configuration to the third configuration by rotating them (90 degrees) around the first and second rotational joints, respectively.

In an example, a wrist-worn computing device with a multi-configuration display can comprise: a band which is worn on a person's wrist and/or lower arm; a primary display (screen) on the dorsal side of the person's wrist; a left display (screen) which is attached by a first rotational joint to the left-dorsal quadrant of the band circumference; a right display (screen) which is attached by a second rotational joint to the right-dorsal quadrant of the band circumference; wherein the device has a first configuration in which the left and right displays lie along the circumference of the band; wherein the device has a second configuration in which the left and right displays extend out (like "wings") from the band in lateral (left and right) directions, respectively; wherein the device has a third configuration in which the left and right displays both extend out from the band in a proximal direction; wherein the left and right displays are changed from the first configuration to the second configuration by pivoting, bending, or straightening their ventral portions away from the circumference of the band; wherein the left and right displays are changed from the second configuration to the third configuration by rotating them (90 degrees) around the first and second rotational joints, respectively.

In an example, a wrist-worn computing device with a multi-configuration display can comprise: a band which is worn on a person's wrist and/or lower arm; a primary display (screen) on the dorsal side of the person's wrist; a left display (screen) which is attached by a first rotational joint to the left-dorsal quadrant of the band circumference; a right display (screen) which is attached by a second rotational joint to the right-dorsal quadrant of the band circumference; wherein the device has a first configuration in which the left and right displays lie along the circumference of the band; wherein the device has a second configuration in which the left and right displays extend out (like "wings") from the band in lateral (left and right) directions, respectively; wherein the device has a third configuration in which the left and right displays both extend out from the band in a distal direction; wherein the left and right displays are changed from the first configuration to the second configuration by pivoting, bending, or straightening their ventral portions away from the circumference of the band; wherein the left and right displays are changed from the second configuration to the third configuration by rotating them (90 degrees) around the first and second rotational joints, respectively. Relevant variations described elsewhere in this disclosure or priority-linked disclosures can also be applied to these examples.

Figure 9:
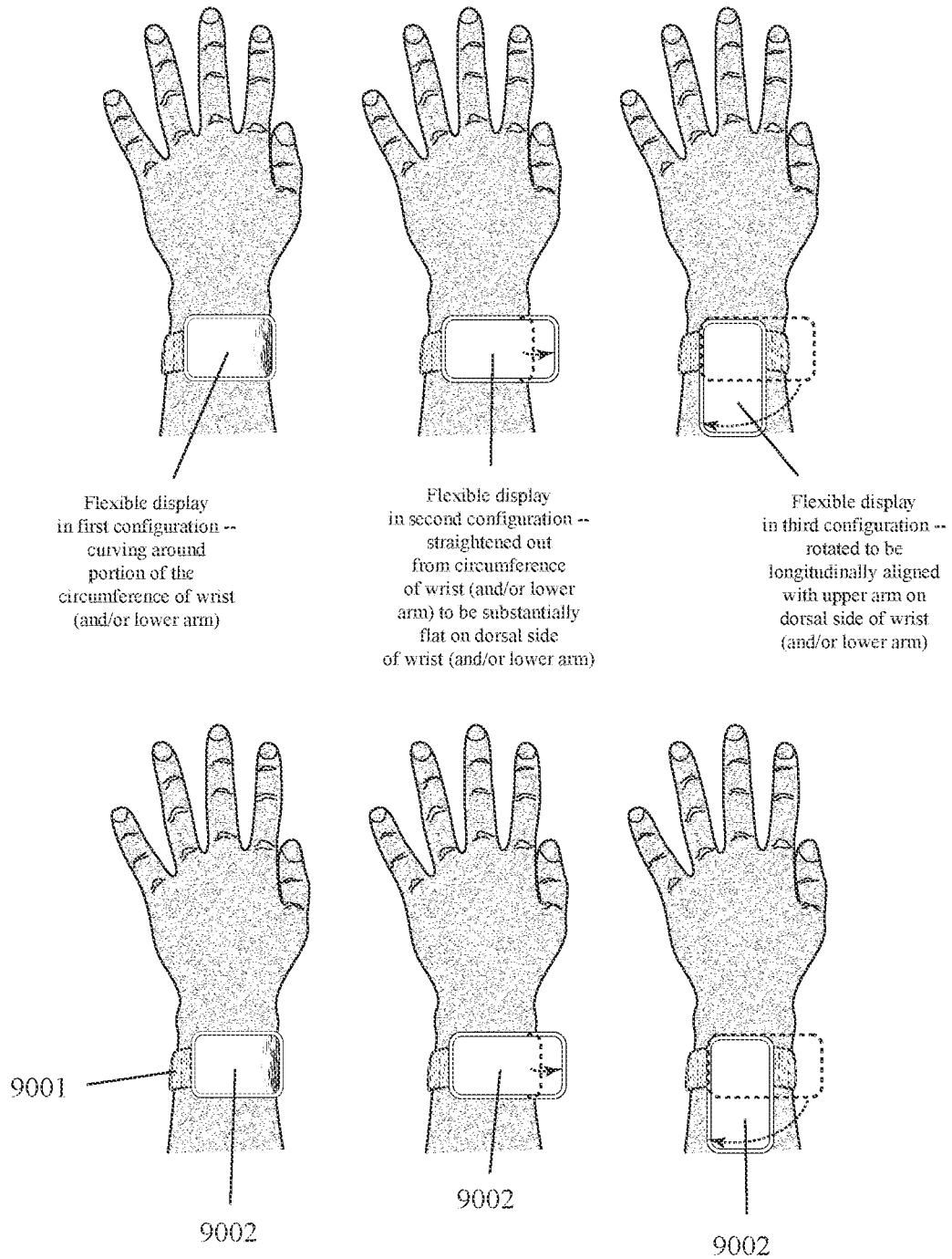
FIG. 9 shows how a flexible secondary display can be moved from a first configuration in which it curves around a lateral side of a wrist band to a second configuration in which it extends straight out from the wrist band in a proximal or distal direction.

FIG. 9 shows three sequential views of a wrist-worn computing device with a multi-configuration display comprising: a band which is worn on a person's wrist and/or lower arm; and a flexible/bendable display which is attached to the band by a rotational joint on the dorsal side of the band; wherein the device has a first configuration in which the flexible/bendable display is arcuate and curves around the circumference of the band from the dorsal side of the band to a lateral (right or left) side of the band; wherein the device has a second configuration in which the flexible/bendable display is substantially planar and extends out from the band in a proximal (or distal) direction; wherein the flexible/bendable display is changed from the first configuration to the second configuration by pivoting, bending, or straightening a ventral portion of the flexible/bendable display away from the circumference of the band and then rotating the flexible/bendable display (90 degrees) around the rotational joint. The upper half of FIG. 9 provides conceptual insight into this example, with written explanations instead of component numbers. The lower half of FIG. 9 shows this same example in conventional patent diagram format with component numbers. These two different perspectives of the same example (in the upper and lower halves of FIG. 9, respectively) combine to provide the reader with a better conceptual understanding of the invention than either perspective alone.

The lower half of FIG. 9 shows three sequential views of a wrist-worn computing device comprising: a band 9001 which is worn on a person's wrist and/or lower arm; and a flexible/bendable display 9002 which is attached to band 9001 by a rotational joint on the dorsal side of the band; wherein the device has a first configuration in which flexible/bendable display 9002 is arcuate and curves around the circumference of band 9001 from the dorsal side of band 9001 to a lateral (right or left) side of band 9001; wherein the device has a second configuration in which flexible/bendable display 9002 is substantially planar and extends out from band 9001 in a proximal (or distal) direction; wherein flexible/bendable display 9002 is changed from the first configuration to the second configuration by pivoting, bending, or straightening a ventral portion of flexible/bendable display 9002 away from the circumference of band 9001 and then rotating flexible/bendable display 9002 around the rotational joint.

In an example, a wearable computing device can comprise: a band which is configured to be worn around at least 50% of the circumference of a person's wrist and/or forearm; a dorsal display which is configured to be worn on the dorsal side of the person's wrist and/or forearm; and a left or right side display which has: (a) a first configuration in which the left or right side display is worn on the left or right side of the person's wrist, (b) a second configuration in which the left or right side display pivots, lifts, and/or straightens to extend out to the left or right of the dorsal display away from the left or right side of the person's wrist, and (c) a third configuration in which the left or right side display rotates around the dorsal display to extend in a distal or proximal direction relative to the dorsal display. Relevant variations described elsewhere in this disclosure or priority-linked disclosures can also be applied to these examples.

Figure 10:
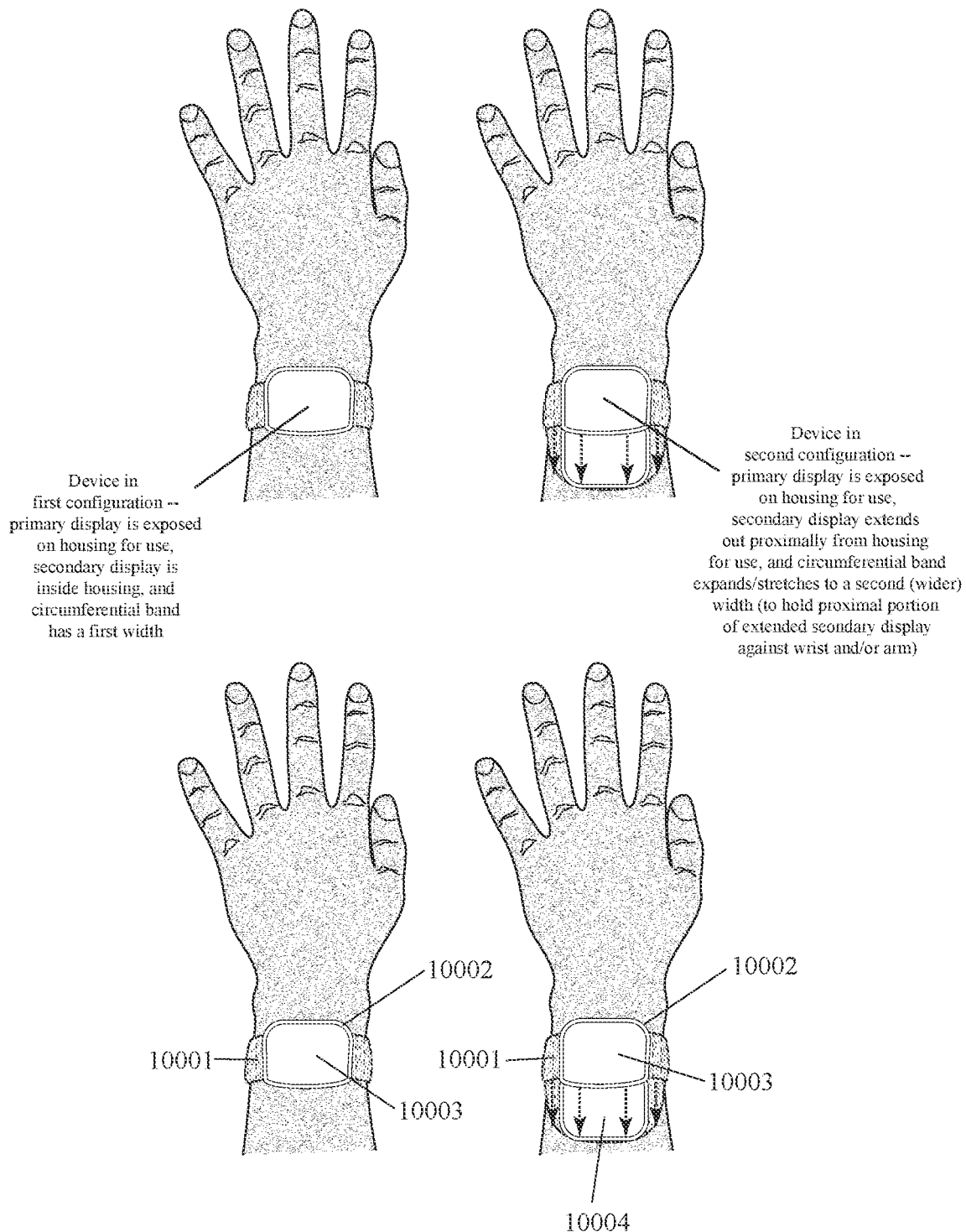
FIG. 10 shows a first example in which a secondary display slides out from alignment with a primary display.

FIG. 10 shows two sequential views of a wrist-worn computing device with a multi-configuration display comprising: a band which is worn on a person's wrist and/or lower arm; a housing which is attached by the band to the dorsal side of the person's wrist and/or lower arm; a first display; and a second display; wherein the device has a first configuration in which the first display is on the upper surface of the housing, the second display is in a first virtual plane, at least three-quarters of the second display is inside the housing, and the dorsal side of the band has a first width; wherein the device has a second configuration in which the first display is on the upper surface of the housing, the second display is in the first virtual plane, at least three-quarters of the second display extends out from the housing in a proximal (or distal) direction, and the dorsal side of the band has a second width, wherein the second width is greater than the first width; and wherein the second display slides out from the housing in a proximal (or distal) direction and the width of the dorsal side of the band expands as the device changes from the first configuration to the second configuration. The upper half of FIG. 10 provides conceptual insight into this example, with written explanations instead of component numbers. The lower half of FIG. 10 shows this same example in conventional patent diagram format with component numbers. These two different perspectives of the same example (in the upper and lower halves of FIG. 10, respectively) combine to provide the reader with a better conceptual understanding of the invention than either perspective alone.

The lower half of FIG. 10 shows two sequential views of a wrist-worn computing device comprising: a band 10001 which is worn on a person's wrist and/or lower arm; a housing 10002 which is attached by the band to the dorsal side of the person's wrist and/or lower arm; a first display 10003; and a second display 10004; wherein the device has a first configuration in which the first display is on the upper surface of the housing, the second display is in a first virtual plane, at least three-quarters of the second display is inside the housing, and the dorsal side of the band has a first width; wherein the device has a second configuration in which the first display is on the upper surface of the housing, the second display is in the first virtual plane, at least three-quarters of the second display extends out from the housing in a proximal (or distal) direction, and the dorsal side of the band has a second width, wherein the second width is greater than the first width; and wherein the second display slides out from the housing in a proximal (or distal) direction and the width of the dorsal side of the band expands as the device changes from the first configuration to the second configuration. Relevant variations described elsewhere in this disclosure or priority-linked disclosures can also be applied to these examples.

Figure 11:
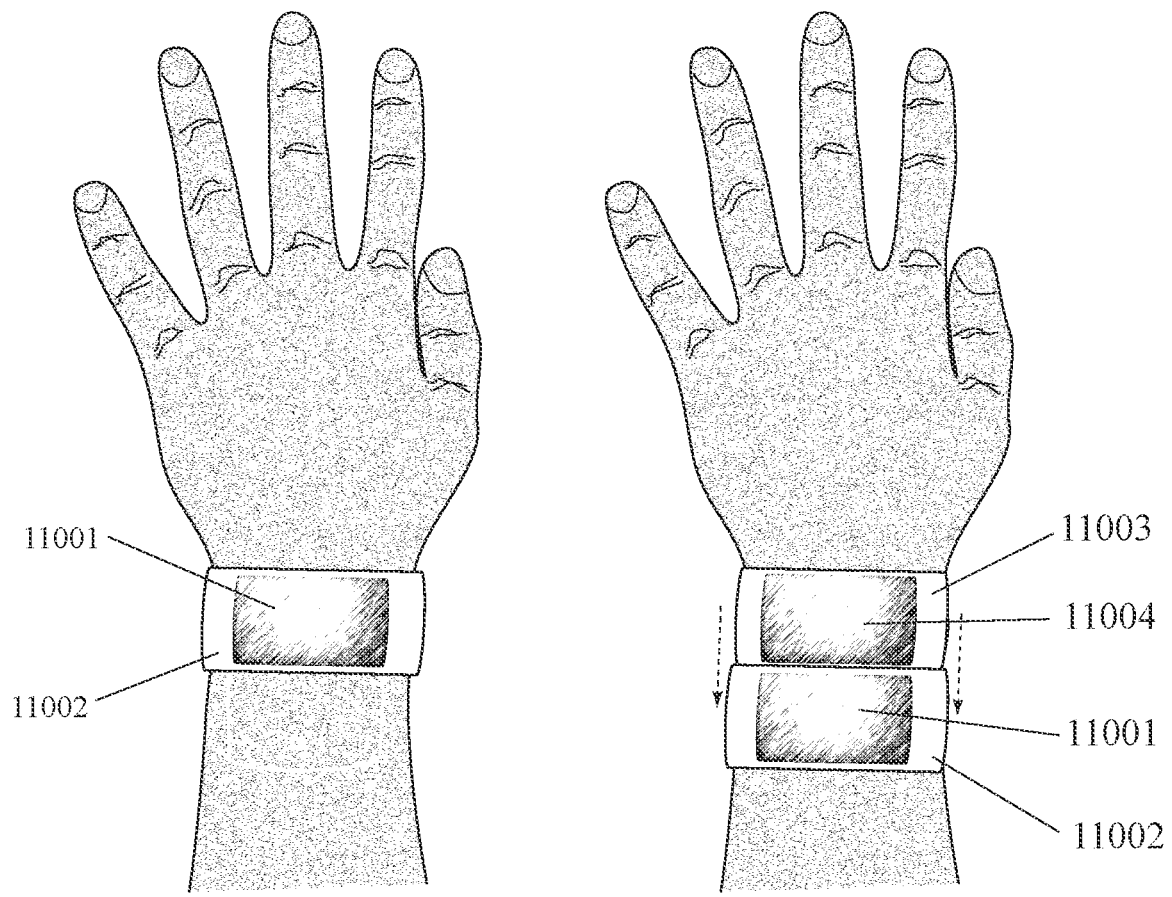
FIG. 11 shows a second example in which a secondary display slides out from alignment with a primary display.

FIG. 11 shows two sequential views of an example of a wrist-worn computing device with a multi-configuration display comprising: a first display 11001, a second display 11004, a first attachment member (e.g. wrist band) 11003, and a second attachment member (e.g. wrist band) 11002. This device has a first configuration in which only first display 11001 is substantially visible to the user and a second configuration in which both first display 11001 and second display 11004 are substantially visible to the user. The left portion of FIG. 11 shows this device in the first configuration and the right portion of FIG. 11 shows this device in the second configuration.

In an example, this device transitions from the first configuration to the second configuration by: movement of first display 11001; movement of second display 11004; or movement of both displays. In an example, movement of one or both displays is done manually by the person wearing the device. In an example, movement of one or both displays is done automatically by an actuator in the device. In various examples, automatic movement can be triggered by one or more events selected from the group consisting of: body motion detected by a sensor in the device; an incoming communication; a touch detected by a sensor in the device; and a voice command.

In an example, one or both displays (11001 and 11004) can move by sliding in a direction which is substantially parallel to the longitudinal axis of the person's forearm and/or perpendicular to the circumference of attachment member 11002. In an example, one or both displays (11001 and 11004) can move by sliding in a direction which is substantially perpendicular to the longitudinal axis of the person's forearm and/or along a segment of the circumference of attachment member 11002. In an example, one or both displays (11001 and 11004) can move by rotating around an axis. In an example, one or both displays (11001 and 11004) can move by flipping them open around a rotational axis.

In an example, first display 11001, second display 11004, or both displays (11001 and 11004) can: comprise a flat or curved computer display screen; be worn on the dorsal, ventral, and/or lateral surface of the person's forearm; and have a shape selected from the group consisting of square, rectangle, conic section, hexagon, polygon with rounded vertexes, oval, and oblong. In an example, first display 11001 and second display 11004 can display different content. In an example, first display 11001 and second display 11004 can display different portions of the same content, together comprising a larger display area that either display by itself. In an example, this allows a user to transition the device from a first configuration with a smaller display area to a second configuration with a larger display area.

In an example, first attachment member 11003, second attachment member 11002, or both attachment members can be worn on a person's body or attached to clothing. In an example, both first attachment member 11003 and second attachment member 11002 can be worn around the person's forearm. In an example, first attachment member 11003, second attachment member 11002, or both attachment members: can have buckles, snaps, adhesive, hook-and-eye mechanisms or other connecting elements so as to be fastened around the circumference of the forearm; can be stretched or expanded around the hand to slip onto the forearm; or can span between 50% and 95% of the circumference of the forearm and be flexible enough to bend around the forearm. In an example, only first attachment member 11003 is worn around the person's forearm and second attachment member 11002 slides out from first attachment member 11003.

In various examples, this device can further comprise one or more components selected from the group consisting of: data processing member, data transmitting member, data receiving member, power source, and energy harvester. In various examples, this device can communicate with a handheld electronic device, a different wearable technology device, an array of wearable sensors, a communication network tower, a satellite, a home control system, and/or an implantable medical device.

In an example, this device can further comprise one or more sensors which are selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can further comprise one or more components selected from the group consisting of: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface. Relevant variations described elsewhere in this disclosure or priority-linked disclosures can also be applied to these examples.

Figure 12:
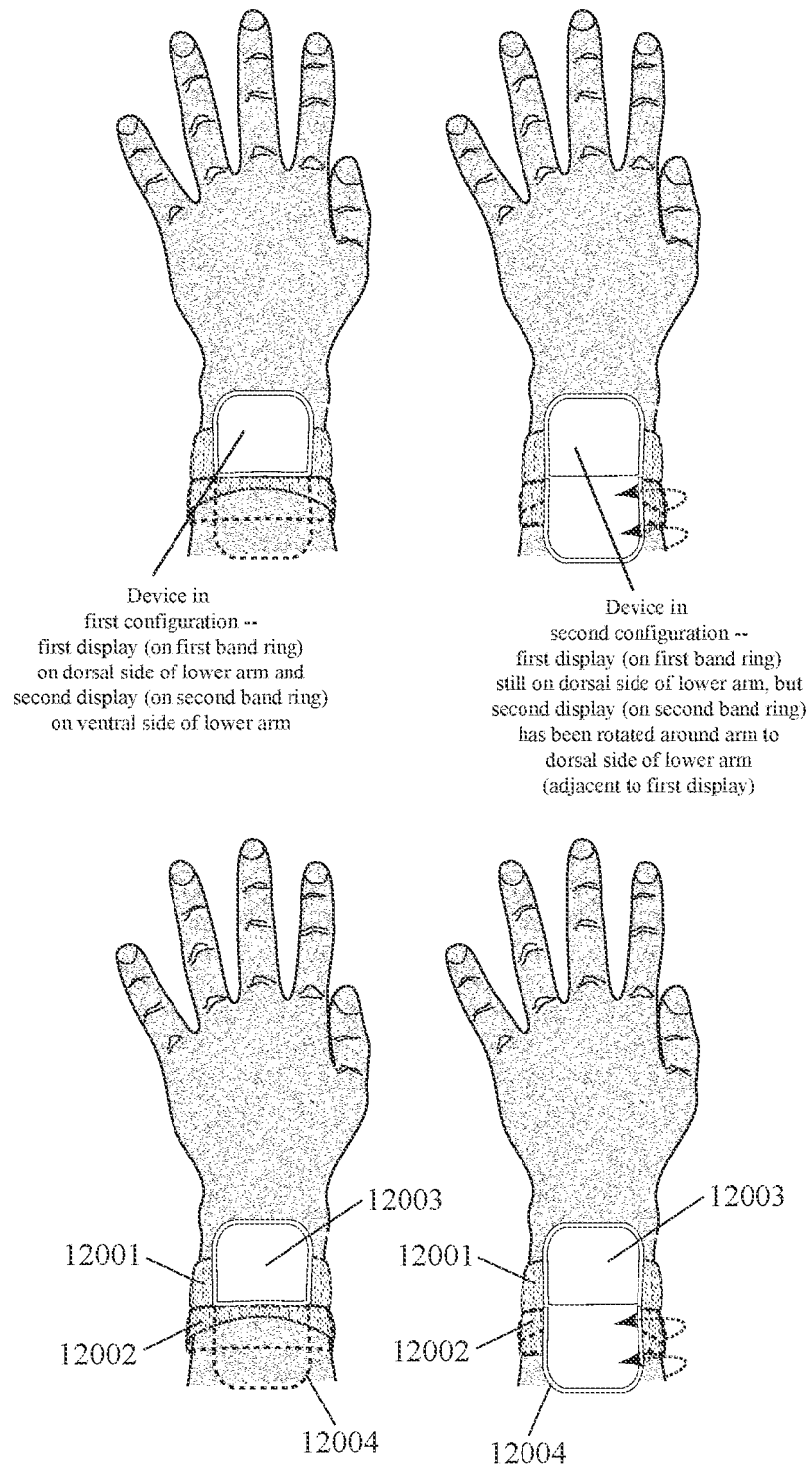
FIG. 12 shows a proximal band with wide and narrow portions around its circumference and a distal band with wide and narrow portions around its circumference, wherein one band is rotated relative to the other to increase combined display size.

FIG. 12 shows two sequential views of a wrist-worn computing device with a multi-configuration display comprising: a proximal band with wide and narrow portions around its circumference which is worn around a person's wrist and/or lower arm; a distal band with wide and narrow portions around its circumference which is worn around the person's wrist and/or lower arm; wherein the proximal band and the distal band are attached to each other in a manner which allows one band to rotate relative to the other band; a first display which is attached to the wide portion of the proximal band; a second display which is attached to the wide portion of the distal band; wherein the device has a first configuration in which the first display and the second display are on different sides of the person's wrist and/or lower arm; wherein the device has a second configuration in which the first display and the second display are aligned on the same side of the person's wrist in order to form a (large) combined display; and wherein the device is changed from its first configuration to its second configuration by rotating one of the bands relative to the other band. The upper half of FIG. 12 provides conceptual insight into this example, with written explanations instead of component numbers. The lower half of FIG. 12 shows this same example in conventional patent diagram format with component numbers. These two different perspectives of the same example (in the upper and lower halves of FIG. 12, respectively) combine to provide the reader with a better conceptual understanding of the invention than either perspective alone.

The lower half of FIG. 12 shows two sequential views of a wrist-worn computing device comprising: a proximal band 12002 with wide and narrow portions around its circumference which is worn around a person's wrist and/or lower arm; a distal band 12001 with wide and narrow portions around its circumference which is worn around the person's wrist and/or lower arm; wherein the proximal band and the distal band are attached to each other in a manner which allows one band to rotate relative to the other band; a first display 12004 which is attached to the wide portion of the proximal band; a second display 12003 which is attached to the wide portion of the distal band; wherein the device has a first configuration in which the first display and the second display are on different sides of the person's wrist and/or lower arm; wherein the device has a second configuration in which the first display and the second display are aligned on the same side of the person's wrist in order to form a (large) combined display; and wherein the device is changed from its first configuration to its second configuration by rotating one of the bands relative to the other band. Relevant variations described elsewhere in this disclosure or priority-linked disclosures can also be applied to these examples.

Figure 13:
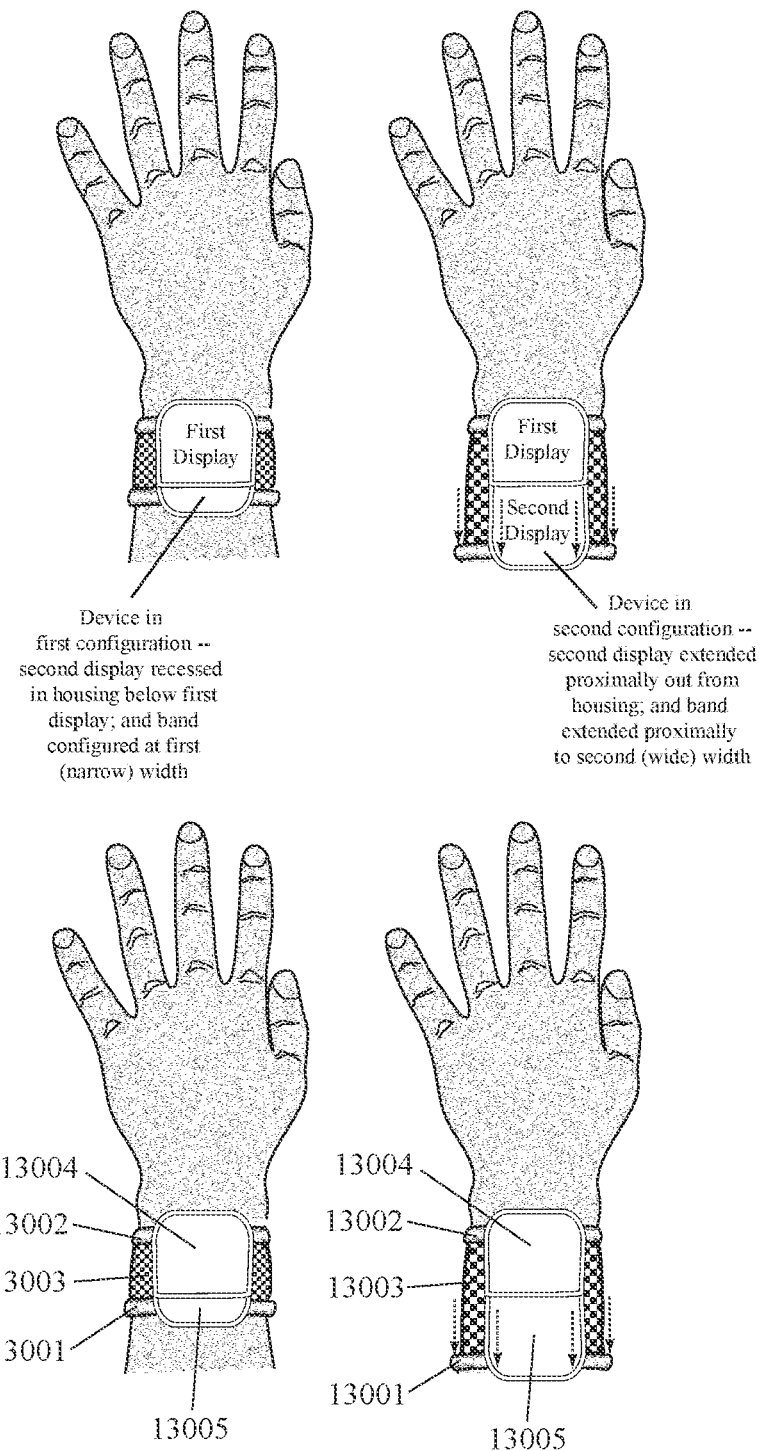
FIG. 13 shows a device with a proximally-stretchable band in which a secondary display slides out from alignment with a primary display.

FIG. 13 shows two sequential views of a wrist-worn computing device with a multi-configuration display comprising: a band which is worn on a person's wrist and/or lower arm; wherein the band further comprises a proximal ring; wherein the band further comprises a distal ring; wherein the band further comprises an expandable mesh (or fabric) between the proximal ring and the distal ring; a first display which is attached to the distal ring; and a second display which is attached to the proximal ring, wherein one of the displays slides under (and out from under) the other display. The upper half of FIG. 13 provides conceptual insight into this example, with written explanations instead of component numbers. The lower half of FIG. 13 shows this same example in conventional patent diagram format with component numbers. These two different perspectives of the same example (in the upper and lower halves of FIG. 13, respectively) combine to provide the reader with a better conceptual understanding of the invention than either perspective alone.

The lower half of FIG. 13 shows two sequential views of a wrist-worn computing device comprising: a band which is worn on a person's wrist and/or lower arm; wherein the band further comprises a proximal ring 13001; wherein the band further comprises a distal ring 13002; wherein the band further comprises an expandable mesh (or fabric) 1303 between the proximal ring and the distal ring; a first display 13004 which is attached to the distal ring; and a second display 13005 which is attached to the proximal ring, wherein one of the displays slides under (and out from under) the other display. Relevant variations described elsewhere in this disclosure or priority-linked disclosures can also be applied to these examples.

Figure 14:
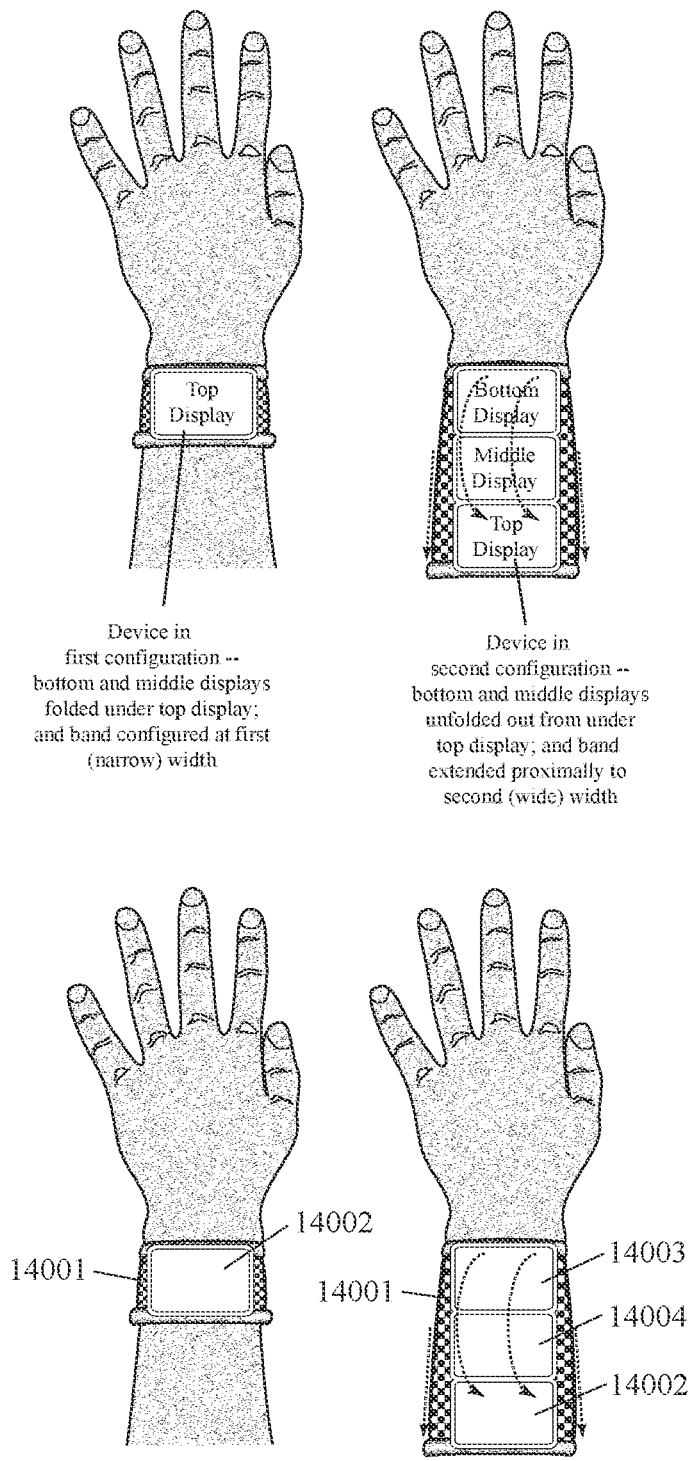
FIG. 14 shows a device with a proximally-stretchable band in which secondary displays unfold out from alignment with a primary display.

FIG. 14 shows two sequential views of a wrist-worn computing device with a multi-configuration display comprising: a variable-width band which is worn around a person's wrist and/or lower arm; a plurality of displays (three in this case) which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by unfolding one or more displays in a proximal direction relative to the other displays and by expanding and/or stretching the width of the band in a proximal direction. The upper half of FIG. 14 provides conceptual insight into this example, with written explanations instead of component numbers. The lower half of FIG. 14 shows this same example in conventional patent diagram format with component numbers. These two different perspectives of the same example (in the upper and lower halves of FIG. 14, respectively) combine to provide the reader with a better conceptual understanding of the invention than either perspective alone.

The lower half of FIG. 14 shows two sequential views of a wrist-worn computing device comprising: a variable-width band 14001 which is worn around a person's wrist and/or lower arm; a plurality of displays (three in this case) 14002, 14003, and 14004, which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by unfolding (or "flipping") one or more displays in a proximal direction relative to the other displays and by expanding and/or stretching the width of the band in a proximal direction. Relevant variations described elsewhere in this disclosure or priority-linked disclosures can also be applied to these examples.

Figure 15:
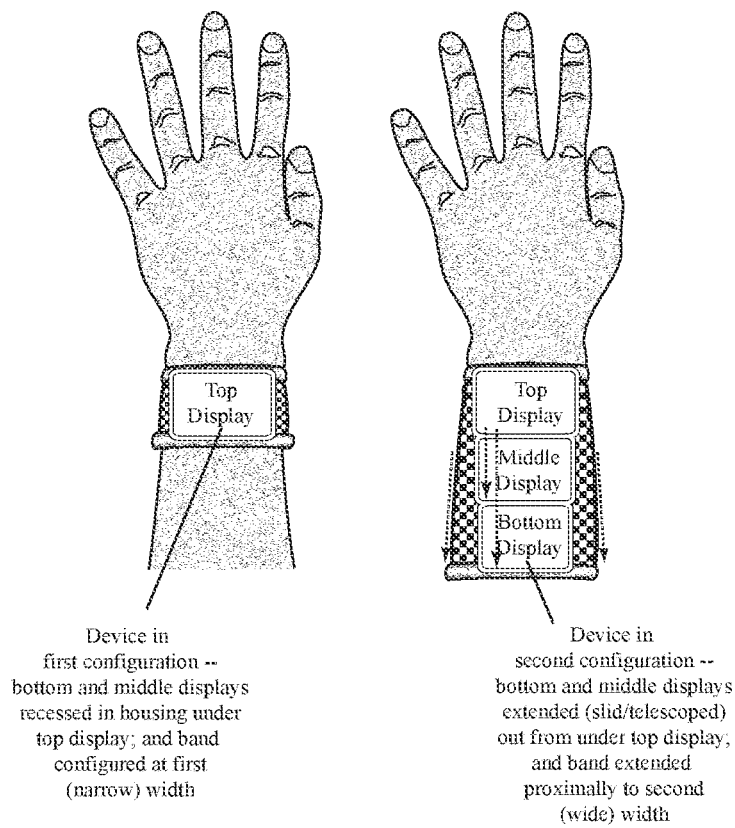
FIG. 15 shows a device with a proximally-stretchable band in which secondary displays telescope out from alignment with a primary display.
Figure 15:
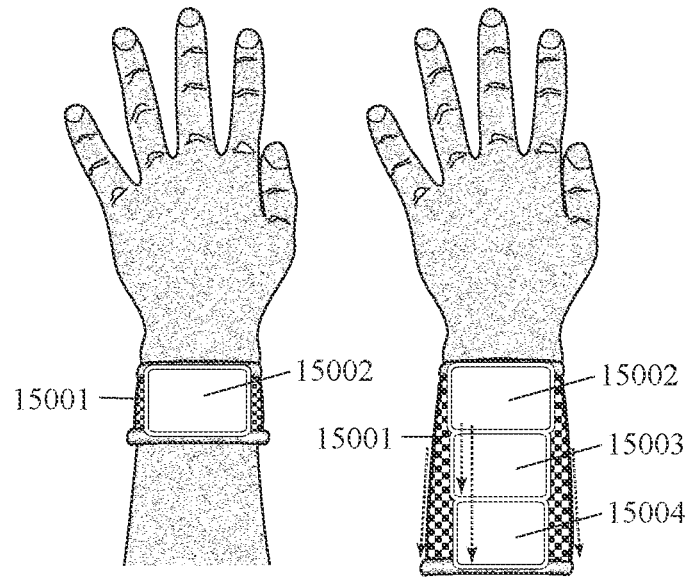

FIG. 15 shows two sequential views of a wrist-worn computing device with a multi-configuration display comprising: a variable-width band which is worn around a person's wrist and/or lower arm; a telescoping series of displays which are attached to the variable-width band; wherein the device has a first configuration in which displays in the telescoping series of displays are inside each other to a first extent and the variable-width band has a first width; wherein the device has a second configuration in which displays in the telescoping series of displays are inside each other to a second extent and the variable-width band has a second width, wherein the second extent is less than the first extent, and wherein the second width is greater than the first width; wherein the device is changed from the first configuration to the second configuration by un-telescoping (e.g. sliding out) displays in a proximal direction and by expanding and/or stretching the width of the band in a proximal direction. The upper half of FIG. 15 provides conceptual insight into this example, with written explanations instead of component numbers. The lower half of FIG. 15 shows this same example in conventional patent diagram format with component numbers. These two different perspectives of the same example (in the upper and lower halves of FIG. 15, respectively) combine to provide the reader with a better conceptual understanding of the invention than either perspective alone.

The lower half of FIG. 15 shows two sequential views of a wrist-worn computing device comprising: a variable-width band 15001 which is worn around a person's wrist and/or lower arm; a telescoping series of displays, 15002, 15003, and 15004, which are attached to the variable-width band; wherein the device has a first configuration in which displays in the telescoping series of displays are inside each other to a first extent and the variable-width band has a first width; wherein the device has a second configuration in which displays in the telescoping series of displays are inside each other to a second extent and the variable-width band has a second width, wherein the second extent is less than the first extent, and wherein the second width is greater than the first width; wherein the device is changed from the first configuration to the second configuration by un-telescoping (e.g. sliding out) displays in a proximal direction and by expanding and/or stretching the width of the band in a proximal direction. Relevant variations described elsewhere in this disclosure or priority-linked disclosures can also be applied to these examples.

The following are some additional examples of how this invention can be embodied in a wrist-worn computing device with a multi-configuration display. In an example, a wrist-worn computing device with a multi-configuration display can comprise: a band which is worn on a person's wrist and/or lower arm; a housing which is attached by the band to the dorsal side of the wrist and/or lower arm; a chain of displays; wherein the chain of displays has a first configuration in which the chain of displays is arcuate and at least partially curves around a portion of the circumference of the band; wherein the chain of displays has a second configuration in which the chain of displays is substantially planar and extends straight outward from the band and/or the housing in a lateral (e.g. right or left) direction in a plane which is substantially coplanar with the housing and/or substantially tangential to the circumference of the band; wherein the chain of displays is moved from its first configuration to its second configuration by moving an end (e.g. the ventral end) of the chain of displays away from the band; wherein the chain of displays has a third configuration in which the chain of displays is substantially planar and extends straight outward from the band and/or the housing in a distal or proximal direction in a plane which is substantially coplanar with the housing and/or substantially tangential to the circumference of the band; and wherein the chain of displays is moved from its second configuration to its third configuration by being rotated (approximately 90 degrees) around the housing and/or around a rotating joint on the band.

In an example, a wrist-worn computing device with a multi-configuration display can comprise: a band which is worn on a person's wrist and/or lower arm; a housing which is attached by the band to the dorsal side of the wrist and/or lower arm; a chain of displays which is attached to the housing and/or the band; wherein the chain of displays has a first configuration in which the chain of displays is arcuate and at least partially curves around a lateral (e.g. right or left) portion of the circumference of the band; wherein the chain of displays has a second configuration in which the chain of displays is substantially straight and extends outward from the band and/or the housing in a lateral (e.g. right or left) direction in a plane which is substantially coplanar with the housing and/or substantially tangential to the circumference of the band; wherein the chain of displays is moved from its first configuration to its second configuration by pivoting, tilting, and/or straightening a ventral portion of the chain of displays away from the band; wherein the chain of displays has a third configuration in which the chain of displays is substantially straight and extends outward from the band and/or the housing in a distal or proximal direction in a plane which is substantially coplanar with the housing and/or substantially tangential to the circumference of the band; and wherein the chain of displays is moved from its second configuration to its third configuration by being rotated (approximately 90 degrees) around the housing and/or around a rotating joint on the band.

In an example, a wrist-worn computing device with a multi-configuration display can comprise: a band which is worn on a person's wrist and/or lower arm; a housing which is attached by the band to the dorsal side of the wrist and/or lower arm; a connected array of displays; wherein the connected array of displays has a first configuration in which the connected array of displays is arcuate and at least partially curves around a lateral (e.g. right or left) portion of the circumference of the band; wherein the connected array of displays has a second configuration in which the connected array of displays is substantially planar and extends straight outward from the band and/or the housing in a lateral (e.g. right or left) direction in a plane which is substantially coplanar with the housing and/or substantially tangential to the circumference of the band; wherein the connected array of displays is moved from its first configuration to its second configuration by pivoting, tilting, and/or straightening a ventral portion of the connected array of displays away from the band; wherein the connected array of displays has a third configuration in which the connected array of displays is substantially planar and extends straight outward from the band and/or the housing in a distal or proximal direction in a plane which is substantially coplanar with the housing and/or substantially tangential to the circumference of the band; and wherein the connected array of displays is moved from its second configuration to its third configuration by being rotated (approximately 90 degrees) around the housing and/or around a rotating joint on the band.

In an example, a wrist-worn computing device with a multi-configuration display can comprise: a band which is worn on a person's wrist and/or lower arm; a housing which is attached by the band to the dorsal side of the wrist and/or lower arm; a display which is attached to a rotating ring and/or bezel on the housing; wherein the display has a first configuration in which the display is arcuate and at least partially curves around a lateral (e.g. right or left) portion of the circumference of the band; wherein the display has a second configuration in which the display is substantially flat and extends outward from the band and/or the housing in a lateral (e.g. right or left) direction in a plane which is substantially coplanar with the housing and/or substantially tangential to the circumference of the band; wherein the display is moved from its first configuration to its second configuration by pivoting, tilting, and/or straightening out a ventral portion of the display away from the band; wherein the display has a third configuration in which the display is substantially flat and extends outward from the band and/or the housing in a distal or proximal direction in a plane which is substantially coplanar with the housing and/or substantially tangential to the circumference of the band; and wherein the display is moved from its second configuration to its third configuration by rotating the ring and/or bezel on the housing. Alternatively, a wrist-worn computing device (such as a smart watch) with a multi-configuration display can comprise: a band which is worn on a person's wrist and/or lower arm; a housing which is attached by the band to the dorsal side of the wrist and/or lower arm; a display which is attached to the housing and/or the band; wherein the display has a first configuration in which the display is arcuate and at least partially curves around a lateral (e.g. right or left) portion of the circumference of the band; wherein the display has a second configuration in which the display is substantially flat and extends outward from the band and/or the housing in a lateral (e.g. right or left) direction in a plane which is substantially coplanar with the housing and/or substantially tangential to the circumference of the band; wherein the display is moved from its first configuration to its second configuration by pivoting, tilting, and/or straightening out a ventral portion of the display away from the band; wherein the display has a third configuration in which the display is substantially flat and extends outward from the band and/or the housing in a distal or proximal direction in a plane which is substantially coplanar with the housing and/or substantially tangential to the circumference of the band; and wherein the display is moved from its second configuration to its third configuration by being rotated (approximately 90 degrees) around a ring and/or bezel on the housing.

In another embodiment, a wrist-worn computing device with a multi-configuration display can comprise: a band which is worn on a person's wrist and/or lower arm; a housing which is attached by the band to the dorsal side of the person's wrist and/or lower arm; a first display; and a second display; wherein the device has a first configuration in which the first display is on the housing, the second display is in a first virtual plane, at least three-quarters of the second display is inside the housing, and the dorsal side of the band has a first width; wherein the device has a second configuration in which the first display is on the housing, the second display is in the first virtual plane, at least three-quarters of the second display extends out from the housing in a proximal (closer to the person's elbow) direction, and the dorsal side of the band has a second width, wherein the second width is greater than the first width; and wherein the second display slides out from the housing in a proximal direction and the width of the dorsal side of the band expands as the device changes from the first configuration to the second configuration. In another example, a wrist-worn computing device with a multi-configuration display can comprise: a band which is worn on a person's wrist and/or lower arm; a housing which is attached to the band; a first display; and a second display; wherein the device has a first configuration in which the first display is on the housing, the second display is in a first virtual plane, the second display is inside the housing, and the dorsal side of the band has a first width; wherein the device has a second configuration in which the first display is (still) on the housing, the second display is (still) in the first virtual plane, the second display extends out from the housing in a proximal (closer to the person's elbow) direction, and the dorsal side of the band has a second width, wherein the second width is greater than the first width; and wherein the second display slides out from the housing in a proximal direction and the width of the dorsal side of the band expands as the device changes from the first configuration to the second configuration.

In an example, a wrist-worn computing device with a multi-configuration display can comprise: a distal band which is worn around a person's wrist and/or lower arm; a proximal band which is worn around the person's wrist and/or lower arm, wherein the proximal band is closer to the person's elbow than the distal band, and wherein the proximal band can be rotated relative to the distal band (around the person's wrist and/or lower arm); a first display which is attached to the distal band; a second display which is attached to the proximal band; wherein the device has a first configuration in which the first display is on a first (e.g. dorsal) side of the person's wrist and/or lower arm and the second display is on a second (e.g. ventral) side of the person's wrist and/or arm; wherein the device has a second configuration in which the first display is on the first (e.g. dorsal) side of the person's wrist and/or lower arm and the second display is also on the first (e.g. dorsal) side of the person's wrist and/or arm; and wherein the device is changed from its first configuration to its second configuration by rotating the proximal band (180 degrees) relative to the distal band. In another example, a wrist-worn computing device (such as a smart watch) with a multi-configuration display can comprise: a distal band which is worn around a person's wrist and/or lower arm; a proximal band which is worn around the person's wrist and/or lower arm, wherein the proximal band is closer to the person's elbow than the distal band, and wherein the distal band can be rotated relative to the proximal band (around the person's wrist and/or lower arm); a first display which is attached to the proximal band; a second display which is attached to the distal band; wherein the device has a first configuration in which the first display is on a first (e.g. dorsal) side of the person's wrist and/or lower arm and the second display is on a second (e.g. ventral) side of the person's wrist and/or arm; wherein the device has a second configuration in which the first display is on the first (e.g. dorsal) side of the person's wrist and/or lower arm and the second display is also on the first (e.g. dorsal) side of the person's wrist and/or arm; and wherein the device is changed from its first configuration to its second configuration by rotating the proximal band relative to the distal band.

For example, a wrist-worn computing device with a multi-configuration flexible/bendable display can comprise: a band which is worn on a person's wrist and/or lower arm; a housing which is attached by the band to the dorsal side of the wrist and/or lower arm; a flexible/bendable display which is attached to rotating ring around the housing and/or a rotating joint on the band; wherein the flexible/bendable display has a first configuration in which the flexible/bendable display at least partially spans a lateral (e.g. right or left) side of the band; wherein the flexible/bendable display has a second configuration in which the flexible/bendable display extends outward from the band and/or the housing in a lateral (e.g. right or left) direction in a plane which is substantially coplanar with the housing and/or substantially tangential to the circumference of the band; wherein the flexible/bendable display is moved from its first configuration to its second configuration by pivoting, tilting, and/or straightening out a ventral portion of the flexible/bendable display away from the band; wherein the flexible/bendable display has a third configuration in which the flexible/bendable display extends outward from the band and/or the housing in a distal or proximal direction in a plane which is substantially coplanar with the housing and/or substantially tangential to the circumference of the band; and wherein the flexible/bendable display is moved from its second configuration to its third configuration by being rotated (approximately 90 degrees) on the ring around the housing and/or around the rotating joint on the band. Alternatively, a wrist-worn computing device with a multi-configuration display can comprise: a band which is worn on a person's wrist and/or lower arm; a right display which is attached by a first rotational joint to the right-dorsal quadrant of the band circumference; a left display which is attached by a second rotational joint to the left-dorsal quadrant of the band circumference; wherein the device has a first configuration in which the right and left displays lie along the circumference of the band; wherein the device has a second configuration in which the right and left displays extend out from the band in lateral (right and left) directions, respectively; wherein the device has a third configuration in which the right and left displays extend out from the band in proximal and distal directions, respectively; wherein the right and left displays are changed from the first configuration to the second configuration by pivoting, bending, or straightening their ventral portions away from the circumference of the band; wherein the right and left displays are changed from the second configuration to the third configuration by rotating them (90 degrees) around the first and second rotational joints, respectively.

In an example, a wrist-worn computing device with a multi-configuration display can comprise: a band which is worn on a person's wrist and/or lower arm; a housing which is attached by the band to the dorsal side of the person's wrist and/or lower arm; a right display which is attached to the right side of the housing; a left display which is attached to the left side of the housing; wherein the device has a first configuration in which the right and left displays lie along the circumference of the band; wherein the device has a second configuration in which the right and left displays extend out from the band in lateral (right and left) directions, respectively; wherein the device has a third configuration in which the right and left displays extend out from the band in proximal and distal directions, respectively; wherein the right and left displays are changed from the first configuration to the second configuration by pivoting, bending, or straightening their ventral portions away from the circumference of the band; wherein the right and left displays are changed from the second configuration to the third configuration by rotating them (90 degrees) around the housing, respectively. In another example, a wrist-worn computing device (such as a smart watch) with a multi-configuration rigid display can comprise: a band which is worn on a person's wrist and/or lower arm; a housing which is attached by the band to the dorsal side of the wrist and/or lower arm; a rigid display which is attached to the housing and/or the band; wherein the rigid display has a first configuration in which the rigid display spans at least part of a lateral (e.g. right or left) side of the band; wherein the rigid display has a second configuration in which the rigid display extends outward from the band and/or the housing in a lateral (e.g. right or left) direction in a plane which is substantially coplanar with the housing and/or substantially tangential to the circumference of the band; wherein the rigid display is moved from its first configuration to its second configuration by pivoting, tilting, and/or straightening out a ventral portion of the rigid display away from the band; wherein the rigid display has a third configuration in which the rigid display extends outward from the band and/or the housing in a distal or proximal direction in a plane which is substantially coplanar with the housing and/or substantially tangential to the circumference of the band; and wherein the rigid display is moved from its second configuration to its third configuration by being rotated (approximately 90 degrees) around the housing and/or around a rotating joint on the band.

In another embodiment, a wrist-worn computing device with a multi-configuration display can comprise: a band which is worn on a person's wrist and/or lower arm; a housing which is attached by the band to the dorsal side of the person's wrist and/or lower arm; a rotating ring or bezel around the housing; a right display which is attached to the right side of the ring or bezel; a left display which is attached to the left side of the ring or bezel; wherein the device has a first configuration in which the right and left displays lie along the circumference of the band; wherein the device has a second configuration in which the right and left displays extend out from the band in lateral (right and left) directions, respectively; wherein the device has a third configuration in which the right and left displays both extend out from the band in a proximal direction; wherein the right and left displays are changed from the first configuration to the second configuration by pivoting, bending, or straightening their ventral portions away from the circumference of the band; wherein the right and left displays are changed from the second configuration to the third configuration by rotating the ring or bezel (by 90 degrees).

For example, a wrist-worn computing device with a multi-configuration display can comprise: a band which is worn on a person's wrist and/or lower arm; a housing which is attached by the band to the dorsal side of the wrist and/or lower arm; a rotating ring or bezel on the housing; a first display which is attached to a first lateral (e.g. right or left) side of the ring or bezel; a second display which is attached to a second lateral (e.g. left or right) side of the ring or bezel, wherein the second side of the ring or bezel is opposite the first side of the ring or bezel; wherein the first display has a first configuration in which it spans at least part of a first lateral (right or left) portion of the circumference of the band; wherein the first display has a second configuration in which it extends straight outward from the housing in a lateral (right or left) manner in a plane which is substantially coplanar with the housing and/or substantially tangential to the circumference of the band; wherein the first display has a third configuration in which it extends straight outward from the housing in a proximal (closer to the person's elbow) or distal (farther from the person's elbow) manner in a plane which is substantially coplanar with the housing and/or substantially tangential to the circumference of the band; wherein the first display is changed from its first configuration to its second configuration by pivoting, bending, or straightening a ventral portion of the first display away from the circumference of the band; wherein the first display is changed from its second configuration to its third configuration by rotating the ring or bezel (by approximately 90 degrees); wherein the second display has a first configuration in which it spans at least part of a second lateral (left or right) portion of the circumference of the band, wherein the second lateral side is opposite the first lateral side; wherein the second display has a second configuration in which it extends straight outward from the housing in a lateral (right or left) manner in a plane which is substantially coplanar with the housing and/or substantially tangential to the circumference of the band; wherein the second display has a third configuration in which it extends straight outward from the housing in a proximal (closer to the person's elbow) or distal (farther from the person's elbow) manner in a plane which is substantially coplanar with the housing and/or substantially tangential to the circumference of the band; wherein the second display is changed from its first configuration to its second configuration by pivoting, bending, or straightening a ventral portion of the second display away from the circumference of the band; and wherein the second display is changed from its second configuration to its third configuration by rotating the ring or bezel (by approximately 90 degrees).

In an example, a wrist-worn computing device with a multi-configuration display can comprise: a band which is worn around a person's wrist and/or lower arm, wherein the band further comprises a proximal ring with a circumferentially-variable width and a distal ring with a circumferentially-variable width, wherein one of the rings can be rotated relative to the other ring around the person's wrist and/or lower arm; a first display which is attached to the proximal ring on a wide portion of the proximal ring; and a second display which is attached to the distal ring on a wide portion of the distal ring, wherein the distal perimeter of the second display extends out from the distal ring in a distal manner; wherein the device has a first configuration in which the first and second displays are on opposite sides of the person's wrist and/or lower arm; wherein the device has a second configuration in which the first and second displays are aligned on the same side of the person's wrist and/or lower arm to form a (large) combined display; and wherein the device is changed from its first configuration to its second configuration by rotating one of the rings relative to the other ring. In another example, a wrist-worn computing device (such as a smart watch) with a multi-configuration display can comprise: a band which is worn on a person's wrist and/or lower arm; a housing which is attached by the band to the dorsal side of the wrist and/or lower arm; one or more displays; wherein the one or more displays have a first configuration in which the one or more displays at least partially span a lateral (e.g. right or left) portion of the circumference of the band; wherein the one or more displays have a second configuration in which the one or more displays extend outward from the band and/or the housing in a lateral (e.g. right or left) direction in a plane which is substantially coplanar with the housing and/or substantially tangential to the circumference of the band; wherein the one or more displays are moved from their first configuration to their second configuration by pivoting, tilting, and/or straightening a ventral portion of the one or more displays away from the band; wherein the one or more displays have a third configuration in which the one or more displays extend outward from the band and/or the housing in a distal or proximal direction in a plane which is substantially coplanar with the housing and/or substantially tangential to the circumference of the band; and wherein the one or more displays are moved from their second configuration to their third configuration by being rotated (approximately 90 degrees) around the housing and/or around a rotating joint on the band.

In an example, a wrist-worn computing device with a multi-configuration display can comprise: a housing which is worn on a person's wrist and/or lower arm; wherein the housing further comprises a base portion which is a first distance from the surface of the person's wrist and/or lower arm and a movable portion which is a second distance from the surface of the person's wrist and/or lower arm, wherein the second distance is greater than the first distance; wherein a first edge of the moveable portion is movably attached to the base portion by a hinge, joint, strap, band, cord, or membrane; wherein the device has a first configuration in which the movable portion is folded over the base portion, being substantially parallel to and above the base portion; wherein the device has a second configuration in which the movable portion is unfolded from the base portion, being substantially coplanar with and adjacent to the base portion, by moving a second edge of the movable portion away from the base, wherein the second edge is opposite the first edge; wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion. Alternatively, a wrist-worn computing device with a multi-configuration display can comprise: a housing which is worn on the dorsal surface of a person's wrist and/or lower arm; wherein the housing further comprises a base portion and a movable portion; wherein a first edge of the moveable portion is moveably attached to the base portion; wherein the device has a first configuration in which the movable portion is folded over the base portion; wherein the device has a second configuration in which the movable portion is unfolded from the base portion by moving a second edge of the movable portion away from the base portion in a lateral direction (substantially perpendicular to the longitudinal axis of the person's lower arm); wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a band which is worn on a person's wrist and/or lower arm; wherein the band further comprises a first ring around the person's wrist and/or lower arm; wherein the band further comprises a second ring around the person's wrist and/or lower arm; wherein the band further comprises a expandable mesh (or fabric) between the first ring and the second ring; a housing which is attached to the first ring; a first display on the housing; and a second display which is attached to the second ring, wherein the second display slides into (and out of) the housing. In another example, a wrist-worn computing device with a multi-configuration display can comprise: a band which is worn on a person's wrist and/or lower arm; wherein the band further comprises a first ring around the person's wrist and/or lower arm; wherein the band further comprises a second ring around the person's wrist and/or lower arm; wherein the band further comprises an elastic mesh (or fabric) between the first ring and the second ring; a housing which is attached to the first ring; a first display on the housing; and a second display which is attached to the second ring, wherein the second display slides into (and out of) the housing.

In another embodiment, a wrist-worn computing device with a multi-configuration display can comprise: a housing (such as a smart watch) which is worn on a person's wrist and/or lower arm; wherein the housing further comprises a base portion and a sliding extension; wherein the device has a first configuration in which at least 90% of the sliding extension is on top of the base portion; wherein the device has a second configuration in which at least 90% of the sliding extension is extended outward from the base portion in a proximal, distal, right-lateral, or left-lateral direction; a first display on the housing; and a second display on the sliding extension. In another example, a wrist-worn computing device (such as a smart watch) with a multi-configuration display can comprise: a housing (such as a smart watch) which is worn on a person's wrist and/or lower arm; wherein the housing further comprises a base portion and a sliding extension; wherein the device has a first configuration in which at least half of the sliding extension is on top of the base portion; wherein the device has a second configuration in which at least half of the sliding extension is extended outward from the base portion in a proximal, distal, right-lateral, or left-lateral direction; a first display on the housing; and a second display on the sliding extension.

For example, a wrist-worn computing device with a multi-configuration display can comprise: a housing (such as a smart watch) which is worn on a person's wrist and/or lower arm; wherein the housing further comprises a base portion and a sliding extension; wherein the device has a first configuration in which at least three-quarters of the sliding extension is on top of the base portion; wherein the device has a second configuration in which at least three-quarters of the sliding extension is laterally adjacent to the base portion in a proximal, distal, right-lateral, or left-lateral direction; a first display on the housing; and a second display on the sliding extension. Alternatively, a wrist-worn computing device (such as a smart watch) with a multi-configuration display can comprise: a housing (such as a smart watch) which is worn on a person's wrist and/or lower arm; wherein the housing further comprises a sliding extension; wherein the device has a first configuration in which at least three-quarters of the sliding extension is on top of the rest of the housing; wherein the device has a second configuration in which at least three-quarters of the sliding extension extends laterally outward from the rest of the housing; wherein the sliding extension remains in substantially the same virtual plane in both the first configuration and the second configuration as well as in the transition from the first configuration to the second configuration; a first quadrilateral display with rounded corners on the housing; and a second quadrilateral display with rounded corners on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which at least three-quarters of the sliding extension is inside the rest of the housing; wherein the device has a second configuration in which at least three-quarters of the sliding extension extends laterally outward from the rest of the housing; wherein the sliding extension remains in substantially the same virtual plane in both the first configuration and the second configuration as well as in the transition from the first configuration to the second configuration; wherein the sliding extension is moved from the first configuration to the second configuration by an electromagnetic actuator or by a mechanical spring; a first quadrilateral display with rounded corners on the housing; and a second quadrilateral display with rounded corners on the sliding extension. In another example, a wrist-worn computing device with a multi-configuration display can comprise: a band with a stretchable and/or expandable mesh (or fabric), wherein the band is worn around a person's wrist and/or lower arm; a plurality of displays which are attached to the band; wherein the device has a first configuration in which displays in the plurality of displays collectively span a first lateral width and the band has a second lateral width; wherein the device has a second configuration in which displays in the plurality of displays collectively span a third lateral width and the band has a fourth lateral width; and wherein the third lateral width is at least 50% greater than the first lateral width and the fourth lateral width is at least 50% greater than the second lateral width.

In an example, a wrist-worn computing device with a multi-configuration display can comprise: a band with a stretchable and/or expandable mesh (or fabric), wherein the band is worn around a person's wrist and/or lower arm; a plurality of displays which are attached to the band; wherein the device has a first configuration in which displays in the plurality of displays collectively span a first lateral width and the band has a second lateral width; wherein the device has a second configuration in which displays in the plurality of displays collectively span a third lateral width and the band has a fourth lateral width; wherein the third lateral width is at least 50% greater than the first lateral width and the fourth lateral width is at least 50% greater than the second lateral width; and where the device is changed from its first configuration to its second configuration by unfolding one or more displays in proximal and/or distal direction(s) and expanding the width of the band in proximal and/or distal direction(s). In another example, a wrist-worn computing device with a multi-configuration display can comprise: a variable-width band which is worn around a person's wrist and/or lower arm; a plurality of displays which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by sliding one or more displays in a proximal direction relative to the other displays and by expanding and/or stretching the band in a proximal direction.

For example, a wrist-worn computing device (such as a smart watch) with a multi-configuration display can comprise: a variable-width band which is worn around a person's wrist and/or lower arm; a plurality of displays which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the first amount is at least 50% greater than the first amount, and wherein the second width at least 50% greater than the first width. Alternatively, a wrist-worn computing device with a multi-configuration display can comprise: a variable-width band which is worn around a person's wrist and/or lower arm; a telescoping series of displays which are attached to the variable-width band; wherein the device has a first configuration in which displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by un-telescoping (e.g. sliding out) one or more displays in a distal direction relative to the other displays and by expanding and/or stretching the band in a distal direction.

In an example, a wrist-worn computing device (such as a smart watch) with a multi-configuration display can comprise: a band with an elastic mesh which is worn around a person's wrist and/or lower arm; a plurality of telescoping displays which are attached to the band; wherein the device has a first configuration in which one or more displays in the plurality of telescoping displays are retracted into each other and the band has a first width; and wherein the device has a second configuration in which one or more displays in the plurality of telescoping displays are extended out from each other and the band has a second width, wherein the second width is greater than the first width. In another example, a wrist-worn computing device with a multi-configuration display can comprise: a housing which is worn on a person's wrist and/or lower arm; wherein the housing further comprises a base portion and a movable portion whose proximal edge is attached to the base portion; wherein the device has a first configuration in which the movable portion is folded over the base portion; wherein the device has a second configuration in which the distal edge of the movable portion is pivoted, tilted, and/or rotated away from the base portion in an outward and proximal manner; wherein the device has a third configuration in which is the movable portion is unfolded from the base portion; wherein the movable portion has a first side and a second side which is opposite the first side; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a housing which is worn on the dorsal surface of a person's wrist and/or lower arm; wherein the housing further comprises a base portion and a movable portion, wherein one edge of the moveable portion is moveably attached to the base portion; wherein the device has a first configuration in which the movable portion is folded over the base portion; wherein the device has a second configuration in which the movable portion is unfolded from the base portion; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is worn on the dorsal surface of a person's wrist and/or lower arm; wherein the housing further comprises a base portion and a movable portion, wherein one edge of the moveable portion is moveably attached to the base portion; wherein the device has a first configuration in which the movable portion is folded over the base portion; wherein the device has a second configuration in which the movable portion is unfolded from the base portion; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion and a movable portion whose distal edge is attached to the base portion; wherein the device has a first configuration in which the movable portion is folded over the base portion; wherein the device has a second configuration in which the proximal edge of the movable portion is pivoted, tilted, and/or rotated away from the base portion in an outward and distal manner; wherein the device has a third configuration in which is the movable portion is unfolded from the base portion; wherein the movable portion has a first side and a second side which is opposite the first side; a first display (or portion of a display) on the first side of the movable portion; a second display (or portion of a display) on the second side of the movable portion; and a third display (or portion of a display) on the base portion. Alternatively, a wrist-worn computing device (such as a smart watch) with a multi-configuration display can comprise: a housing (such as a smart watch) which is worn on a person's wrist and/or lower arm; wherein the housing further comprises a base portion and a sliding extension; wherein the device has a first configuration in which the sliding extension is on top of the base portion; wherein the device has a second configuration in which the sliding extension is extended outward from the base portion in a proximal direction; a first display on the housing; and a second display on the sliding extension.

In another embodiment, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is on top of the rest of the housing; wherein the device has a second configuration in which the sliding extension extends out from the rest of the housing; a first quadrilateral display with rounded corners on the housing; and a second quadrilateral display with rounded corners on the sliding extension. In another example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is inside the rest of the housing; wherein the device has a second configuration in which the sliding extension extends out from the rest of the housing; a first display on the housing; and a second display on the sliding extension.

For example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is inside the rest of the housing; wherein the device has a second configuration in which the sliding extension extends out from the rest of the housing in a proximal, distal, right-lateral, or left-lateral direction; a first display on the housing; and a second display on the sliding extension. In another example, a wrist-worn computing device (such as a smart watch) with a multi-configuration display can comprise: a housing (such as a smart watch) which is worn on a person's wrist and/or lower arm; wherein the housing further comprises a sliding extension; wherein the device has a first configuration in which the sliding extension is substantially inside the rest of the housing; wherein the device has a second configuration in which the sliding extension extends in a coplanar manner outward from the rest of the housing; a first display on the housing; and a second display on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is recessed within the housing; wherein the device has a second configuration in which the sliding extension extends outward from the rest of the housing; a first display on the housing; and a second display on sliding extension. In another example, a wrist-worn computing device (such as a smart watch) with a multi-configuration display can comprise: a housing (such as a smart watch) which is worn on a person's wrist and/or lower arm; wherein the housing further comprises a sliding extension; wherein the device has a first configuration in which the sliding extension is substantially on top of (or inside) the housing; wherein the device has a second configuration in which the sliding extension extends outward from the rest of the housing, wherein the sliding extension remains in substantially the same virtual plane as it moves from the first configuration to the second configuration; a first display on the housing; and a second display on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially on top of (or inside) the housing; wherein the device has a second configuration in which the sliding extension extends outward from the rest of the housing, wherein the centroid of the sliding extension is moved in a distal direction (e.g. farther from the person's elbow) as the sliding extension is moved from the first configuration to the second configuration; a first display on the housing; and a second display on the sliding extension. Alternatively, a wrist-worn computing device with a multi-configuration display can comprise: a housing (such as a smart watch) which is worn on a person's wrist and/or lower arm; wherein the housing further comprises a base portion and an upper sliding portion; wherein the device has a first configuration in which the upper sliding portion is substantially on top of the base portion; wherein the device has a second configuration in which the upper sliding portion is substantially adjacent (in a proximal, distal, or lateral manner) to the base portion; a first display on the housing; and a second display on the sliding extension.

For example, a wrist-worn computing device with a multi-configuration display can comprise: a band which is worn on a person's wrist and/or lower arm; a flexible/bendable array of displays which is attached to the band; wherein the flexible/bendable array of displays has a first configuration which at least partially curves around a lateral (e.g. right or left) portion of the circumference of the band; wherein the flexible/bendable array of displays has a second configuration which extends outward from the band in a lateral (e.g. right or left) direction in a plane which is substantially tangential to the circumference of the band; wherein the flexible/bendable array of displays is moved from its first configuration to its second configuration by pivoting, tilting, and/or straightening an end of the flexible/bendable array of displays away from the band; wherein the flexible/bendable array of displays has a third configuration in which the flexible/bendable array of displays extends outward from the band in a distal or proximal direction in a plane which is substantially tangential to the circumference of the band; and wherein the flexible/bendable array of displays is moved from its second configuration to its third configuration by being rotated (approximately 90 degrees) around a joint and/or axle on the band.

In an example, a wrist-worn computing device with a multi-configuration display can comprise: a band which is worn on a person's wrist and/or lower arm; a flexible/bendable display whose dorsal portion is attached to a rotating joint or axle on the band; wherein the flexible/bendable display has a first configuration in which the flexible/bendable display is arcuate and curves around a lateral (e.g. right or left) portion of the circumference of the band; wherein the flexible/bendable display has a second configuration in which the flexible/bendable display is substantially planar and extends outward from the band in a lateral (e.g. right and/or left) direction in a plane which is substantially tangential to the circumference of the band; wherein the flexible/bendable display has a third configuration in which the flexible/bendable display is substantially planar and extends outward from the band in a distal and/or proximal direction in a plane which is substantially tangential to the circumference of the band; wherein the flexible/bendable display is moved from its first configuration to its second configuration by pivoting, tilting, and/or straightening a ventral portion of the flexible/bendable display away from the band; and wherein the flexible/bendable display is moved from its second configuration to its third configuration by being rotated (approximately 90 degrees) around the rotating joint or axle on the band.

For example, a wrist-worn computing device with a multi-configuration display can comprise: a band which is worn on a person's wrist and/or lower arm; a housing attached to the band; wherein the housing further comprises a base portion and a movable portion, wherein the moveable portion is moveably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a band which is worn on a person's wrist and/or lower arm; a housing which is attached to the band; wherein the housing further comprises a base portion and a movable portion, wherein one edge of the moveable portion is moveably attached to the base portion by a hinge, joint, strap, band, cord, or membrane; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In another embodiment, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first (single-display) configuration in which the movable portion is folded over (being parallel to and on top of) the base portion; wherein the device has a second (multi-display) configuration in which the movable portion is unfolded (e.g. pivoted, tilted, flipped, and/or rotated) outward from around a hinge, joint, strap, band, cord, or membrane not being parallel to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which at least part of the movable portion is folded over at least part of the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces substantially away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device (such as a smart watch) with a multi-configuration display can comprise: a housing which is attached (by a band) to the surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and distal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a housing which is worn on a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over the base portion; wherein the device has a second configuration in which the movable portion is unfolded in a distal direction (away from the person's elbow) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is attached by a band to the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) to a location which is distal (farther from the person's elbow) relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a housing which is attached to the surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and proximal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded (e.g. pivoted, tilted, flipped, and/or rotated) in an outward and proximal direction (toward the person's elbow) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. Alternatively, a wrist-worn computing device (such as a smart watch) with a multi-configuration display can comprise: a housing which is attached by a band to a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward in a lateral direction (substantially perpendicular to the longitudinal axis of the person's lower arm) around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In another embodiment, a wrist-worn computing device with a multi-configuration display can comprise: a housing which is attached by a band to the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward in a lateral direction (substantially perpendicular to the longitudinal axis of the person's lower arm) around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device (such as a smart watch) with a multi-configuration display can comprise: a housing which is attached by a band to the dorsal surface of a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration (along a radial vector outward from the center of the wrist and/or lower arm) and faces generally toward the wrist and/or lower arm in the second configuration; wherein the movable portion has a second side which faces generally toward the wrist and/or lower arm in the first configuration and faces away from the wrist and/or lower arm in the second configuration (along a radial vector outward from the center of the wrist and/or lower arm); a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over (being parallel to and on top of) the base portion; wherein the device has a second configuration in which the movable portion is unfolded from (being coplanar with, but not on top of) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded (around a hinge, joint, strap, band, cord, or membrane) relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces substantially away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over (being parallel to and on top of) the base portion; wherein the device has a second configuration in which the movable portion is unfolded from (not being parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist (and is seen) in the first configuration and faces (substantially) toward the wrist and/or lower arm (and is hidden) in the second configuration; wherein the movable portion has a second side which faces (substantially) toward the wrist and/or lower arm (and is hidden) in the first configuration and faces away from the wrist (and is seen) in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a housing which is worn on the dorsal surface of a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. Alternatively, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side and a second side, wherein the second side is opposite the first side; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a single-part-display configuration in which the movable portion is folded over the base portion; wherein the device has a multi-part-display configuration in which the movable portion is unfolded from the base portion; wherein the movable portion has a first side which faces away from the wrist and/or lower arm in the single-part-display configuration and faces (substantially) toward the wrist and/or lower arm in the second configuration; wherein the movable portion has a second side which faces (substantially) toward the wrist and/or lower arm in the first configuration and faces away from the wrist and/or lower arm in the multi-part-display configuration; a first display on the first side of the movable portion which functions as the display in the single-part-display configuration; a first portion of a second display on the second side of the movable portion which functions as one of a plurality of displays in the multi-part-display configuration; and a second portion of the second display on the base portion which functions as one of the plurality of displays in the multi-part-display configuration.

In another example, a wrist-worn computing device with a multi-configuration display can comprise: a housing which is worn on a person's wrist and/or lower arm; wherein the housing further comprises a lower base portion; wherein the housing further comprises a upper movable portion which is movably attached to the base portion (e.g. by a hinge, joint, strap, band, cord, or membrane); wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In another embodiment, a wrist-worn computing device with a multi-configuration display can comprise: a smart watch which is worn on the dorsal surface of a person's wrist and/or lower arm; wherein the smart watch further comprises a lower base portion; wherein the housing further comprises a upper movable portion, wherein the distal (e.g. farther from the person's elbow) edge of the upper moveable portion is movably and/or flexibly attached to the lower base portion by a hinge, joint, strap, band, cord, or membrane; wherein the device has a single-display configuration in which the movable portion is folded over the base portion; wherein the device has a multi-display configuration in which the movable portion is unfolded from the base portion by pivoting, tilting, and/or rotating the proximal (e.g. closer to the person's elbow) edge of the movable portion away from the base portion; wherein the movable portion has a first side which faces generally away from the wrist in the single-display configuration and faces generally toward the wrist and/or lower arm in the multi-display configuration; wherein the movable portion has a second side which faces generally toward the wrist and/or lower arm in the single-display configuration and faces generally away from the wrist in the multi-display configuration; a first display on the first side of the movable portion; a second display (or portion of a multi-part display) on the second side of the movable portion; and a third display (or portion of a multi-part display) on the base portion.

For example, a wrist-worn computing device (such as a smart watch) with a multi-configuration display can comprise: a housing which is worn on a person's wrist and/or lower arm; wherein the housing further comprises a base portion (which is a first distance from the surface of the person's wrist and/or lower arm) and a movable portion (which is a second distance from the surface of the person's wrist and/or lower arm, wherein the second distance is greater than the first distance); wherein the moveable portion is movably attached to the base portion; wherein the device has a first configuration in which the movable portion is folded over the base portion; wherein the device has a second configuration in which the movable portion is unfolded from the base portion; wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display)

on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over the base portion; wherein the device has a second configuration in which an edge of the movable portion is unfolded in an outward and proximal direction relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration. Alternatively, a wrist-worn computing device (such as a smart watch) with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over the base portion; wherein the device has a second configuration in which the movable portion is unfolded from the base portion; wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward in a lateral direction (substantially perpendicular to the longitudinal axis of the person's lower arm) around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a band which is worn on a person's wrist and/or lower arm; one or more displays which are attached to a rotating joint or axle on the band; wherein the one or more displays have a first configuration in which the one or more displays at least partially curve around a portion of the circumference of the band; wherein the one or more displays have a second configuration in which the one or more displays extend straight outward from the band and/or the housing in a lateral (e.g. right or left) direction in a plane which is substantially coplanar with the housing and/or substantially tangential to the circumference of the band; wherein the one or more displays are moved from their first configuration to their second configuration by moving an end portion (e.g. the ventral end) of the one or more displays away from the band; wherein the one or more displays have a third configuration in which the one or more displays extend straight outward from the band and/or the housing in a distal or proximal direction in a plane which is substantially coplanar with the housing and/or substantially tangential to the circumference of the band; and wherein the one or more displays are moved from their second configuration to their third configuration by being rotated approximately 90 degrees around the rotating joint or axle on the band.

In an example, a wrist-worn computing device with a multi-configuration display can comprise: a band which is worn on a person's wrist and/or lower arm; one or more displays which are attached to the dorsal side of the band and/or to a housing on the dorsal side of the band; wherein the one or more displays have a first configuration in which the one or more displays are arcuate and curve around a lateral (right or left) portion of the circumference of the band; wherein the one or more displays have a second configuration in which the one or more displays are substantially planar and stick straight out (like one or more wings) in a lateral (right and/or left) manner from the dorsal side of the band and/or the housing on the dorsal side of the band; wherein the one or more displays have a third configuration in which the one or more displays are substantially planar and stick straight out in a proximal (closer to the person's elbow) and/or distal (farther from the person's elbow) manner from the dorsal side of the band and/or the housing on the dorsal side of the band; wherein the one or more displays are changed from their first configuration to their second configuration by detaching an end and moving (e.g. pivoting, bending, unfolding, or lifting) the one or more displays away from the circumference of the band; wherein the one or more displays are changed from their second configuration to their third configuration by rotating (the end of) the one or more displays around the dorsal side of the band and/or around the housing on the dorsal side of the band. In another example, a wrist-worn computing device with a multi-configuration display can comprise: a proximal band which is worn around a person's wrist and/or lower arm; a distal band with wide and narrow portions around its circumference which is worn around the person's wrist and/or lower arm; wherein the proximal band and the distal band are attached to each other in a manner which allows one band to rotate relative to the other band; a first display which is attached to the proximal band; a second display which is attached to the wide portion of the distal band; wherein the device has a first configuration in which the first display and the second display are on different sides of the person's wrist and/or lower arm; wherein the device has a second configuration in which the first display and the second display are (aligned) on the same side of the person's wrist in order to form a (large) combined display; and wherein the device is changed from its first configuration to its second configuration by rotating one of the bands relative to the other band.

In another embodiment, a wrist-worn computing device (such as a smart watch) with a multi-configuration display can comprise: a housing which is worn on a person's wrist and/or lower arm; wherein the housing further comprises a base portion and a movable portion; wherein the right-lateral edge of the moveable portion is movably attached to the base portion (by a hinge, joint, strap, band, cord, or membrane), wherein lateral means perpendicular to the longitudinal axis of a person's lower arm; wherein the device has a first configuration in which the movable portion is folded over the base portion; wherein the device has a second configuration in which the movable portion is unfolded from the base portion; wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a band which is worn on a person's wrist and/or lower arm; a housing which is attached by the band to the dorsal side of the wrist and/or lower arm; a chain of displays; wherein the chain of displays has a first configuration in which the chain of displays at least partially spans a lateral (e.g. right or left) side of the band; wherein the chain of displays has a second configuration in which the chain of displays extends straight outward from the band and/or the housing in a lateral (e.g. right or left) direction in a plane which is substantially coplanar with the housing and/or substantially tangential to the circumference of the band; wherein the chain of displays is moved from its first configuration to its second configuration by pivoting, tilting, and/or straightening a ventral portion of the chain of displays away from the band; wherein the chain of displays has a third configuration in which the chain of displays extends straight outward from the band and/or the housing in a distal or proximal direction in a plane which is substantially coplanar with the housing and/or substantially tangential to the circumference of the band; and wherein the chain of displays is moved from its second configuration to its third configuration by being rotated (approximately 90 degrees) around the housing and/or around a rotating joint on the band.

In an example, a wrist-worn computing device (such as a smart watch) with a multi-configuration display can comprise: a band which is worn on a person's wrist and/or lower arm; a housing which is attached by the band to the dorsal side of the wrist and/or lower arm; a chain of displays which is moveable connected to the housing and/or the band; wherein the chain of displays has a first configuration in which the chain of displays is arcuate and at least partially curves around a portion of the circumference of the band; wherein the chain of displays has a second configuration in which the chain of displays is substantially planar and extends straight outward from the band and/or the housing in a lateral (e.g. right or left) direction in a plane which is substantially coplanar with the housing and/or substantially tangential to the circumference of the band; wherein the chain of displays is moved from its first configuration to its second configuration by moving an end (e.g. the ventral end) of the chain of displays away from the band; wherein the chain of displays has a third configuration in which the chain of displays is substantially planar and extends straight outward from the band and/or the housing in a distal or proximal direction in a plane which is substantially coplanar with the housing and/or substantially tangential to the circumference of the band; and wherein the chain of displays is moved from its second configuration to its third configuration by being rotated (approximately 90 degrees) around the housing and/or around a rotating joint on the band.

In an example, a wrist-worn computing device with a multi-configuration display can comprise: a band which is worn on a person's wrist and/or lower arm; a housing which is attached by the band to the dorsal side of the wrist and/or lower arm; a connected series of displays; wherein the connected series of displays has a first configuration in which the connected series of displays is arcuate and at least partially curves around a lateral (e.g. right or left) portion of the circumference of the band; wherein the connected series of displays has a second configuration in which the connected series of displays extends straight outward from the band and/or the housing in a lateral (e.g. right or left) direction in a plane which is substantially coplanar with the housing and/or substantially tangential to the circumference of the band; wherein the connected series of displays is moved from its first configuration to its second configuration by pivoting, tilting, and/or straightening out a ventral portion of the connected series of displays away from the band; wherein the connected series of displays has a third configuration in which the connected series of displays extends straight outward from the band and/or the housing in a distal or proximal direction in a plane which is substantially coplanar with the housing and/or substantially tangential to the circumference of the band; and wherein the connected series of displays is moved from its second configuration to its third configuration by being rotated (approximately 90 degrees) around the housing and/or around a rotating joint on the band.

For example, a wrist-worn computing device with a multi-configuration display can comprise: a band which is worn on a person's wrist and/or lower arm; a housing which is attached by the band to the dorsal side of the wrist and/or lower arm; a display which is attached to rotating ring around the housing and/or a rotating joint on the band; wherein the display has a first configuration in which the display at least partially spans a lateral (e.g. right or left) side of the band; wherein the display has a second configuration in which the display extends outward from the band and/or the housing in a lateral (e.g. right or left) direction in a plane which is substantially coplanar with the housing and/or substantially tangential to the circumference of the band; wherein the display is moved from its first configuration to its second configuration by pivoting, tilting, and/or straightening out a ventral portion of the display away from the band; wherein the display has a third configuration in which the display extends outward from the band and/or the housing in a distal or proximal direction in a plane which is substantially coplanar with the housing and/or substantially tangential to the circumference of the band; and wherein the display is moved from its second configuration to its third configuration by being rotated (approximately 90 degrees) on the ring around the housing and/or around the rotating joint on the band. In another example, a wrist-worn computing device with a multi-configuration display can comprise: a band which is worn on a person's wrist and/or lower arm; a housing which is attached by the band to the dorsal side of the wrist and/or lower arm; a display which is attached to the housing and/or the band; wherein the display has a first configuration in which the display spans at least a portion of a lateral (e.g. right or left) side of the band; wherein the display has a second configuration in which the display extends outward from the band and/or the housing in a lateral (e.g. right or left) direction in a plane which is substantially coplanar with the housing and/or substantially tangential to the circumference of the band; wherein the display is moved from its first configuration to its second configuration by detaching a ventral portion of the display from the band and pivoting, tilting, and/or straightening the ventral portion away from the band; wherein the display has a third configuration in which the display extends outward from the band and/or the housing in a distal or proximal direction in a plane which is substantially coplanar with the housing and/or substantially tangential to the circumference of the band; and wherein the display is moved from its second configuration to its third configuration by being rotated (approximately 90 degrees) around the housing and/or around a rotating joint on the band.

In an example, a wrist-worn computing device with a multi-configuration display can comprise: a band which is worn on a person's wrist and/or lower arm; a housing which is attached by the band to the dorsal side of the person's wrist and/or lower arm; a first display; and a second display; wherein the device has a first configuration in which the first display is on the housing, the second display is in a first virtual plane, at least three-quarters of the second display is inside the housing, and the dorsal side of the band has a first width; wherein the device has a second configuration in which the first display is on the housing, the second display is in the first virtual plane, at least three-quarters of the second display extends out from the housing in a distal (farther from the person's elbow) direction, and the dorsal side of the band has a second width, wherein the second width is greater than the first width; and wherein the second display slides out from the housing in a proximal direction and the width of the dorsal side of the band expands as the device changes from the first configuration to the second configuration. In another example, a wrist-worn computing device (such as a smart watch) with a multi-configuration display can comprise: a band which is worn on a person's wrist and/or lower arm; a housing which is attached to the band to the dorsal side of the person's wrist and/or arm; a first display; and a second display; wherein the device has a first configuration in which the first display is on the housing, the second display is inside the housing, and the dorsal side of the band has a first width; wherein the device has a second configuration in which the first display is on the housing, the second display extends out from the housing in a proximal (closer to the person's elbow) direction, and the dorsal side of the band has a second width, wherein the second width is greater than the first width; and wherein the second display slides out from the housing in a proximal direction and the width of the dorsal side of the band expands as the device changes from the first configuration to the second configuration.

For example, a wrist-worn computing device with a multi-configuration display can comprise: a distal band which is worn around a person's wrist and/or lower arm; a proximal band which is worn around the person's wrist and/or lower arm, wherein the proximal band is closer to the person's elbow than the distal band, and wherein the proximal band can be rotated relative to the distal band (around the person's wrist and/or lower arm); a first display which is attached to the distal band; a second display which is attached to the proximal band; wherein the device has a first configuration in which the first display is on a first (e.g. dorsal) side of the person's wrist and/or lower arm and the second display is on a second (e.g. lateral) side of the person's wrist and/or arm; wherein the device has a second configuration in which the first display is on the first (e.g. dorsal) side of the person's wrist and/or lower arm and the second display is also on the first (e.g. dorsal) side of the person's wrist and/or arm; and wherein the device is changed from its first configuration to its second configuration by rotating the proximal band (90 degrees) relative to the distal band.

In another embodiment, a wrist-worn computing device (such as a smart watch) with a multi-configuration flexible/bendable display can comprise: a band which is worn on a person's wrist and/or lower arm; a housing which is attached by the band to the dorsal side of the wrist and/or lower arm; a first flexible/bendable display which is attached to a first lateral (e.g. right or left) side of the housing; a second flexible/bendable display which is attached to a second lateral (e.g. left or right) side of the housing, wherein the second side of the housing is opposite the first side of the housing; wherein the first flexible/bendable display has a first configuration in which it spans at least part of a first lateral (right or left) portion of the circumference of the band; wherein the first flexible/bendable display has a second configuration in which it extends straight outward from the housing in a lateral (right or left) manner in a plane which is substantially coplanar with the housing and/or substantially tangential to the circumference of the band; wherein the first flexible/bendable display has a third configuration in which it extends straight outward from the housing in a proximal (closer to the person's elbow) or distal (farther from the person's elbow) manner in a plane which is substantially coplanar with the housing and/or substantially tangential to the circumference of the band; wherein the first flexible/bendable display is changed from its first configuration to its second configuration by pivoting, bending, or straightening a ventral portion of the first flexible/bendable display away from the circumference of the band; wherein the first flexible/bendable display is changed from its second configuration to its third configuration by being rotated around the housing or on a rotating housing (by approximately 90 degrees); wherein the second flexible/bendable display has a first configuration in which it spans at least part of a second lateral (left or right) portion of the circumference of the band, wherein the second lateral side is opposite the first lateral side; wherein the second flexible/bendable display has a second configuration in which it extends straight outward from the housing in a lateral (right or left) manner in a plane which is substantially coplanar with the housing and/or substantially tangential to the circumference of the band; wherein the second flexible/bendable display has a third configuration in which it extends straight outward from the housing in a proximal (closer to the person's elbow) or distal (farther from the person's elbow) manner in a plane which is substantially coplanar with the housing and/or substantially tangential to the circumference of the band; wherein the second flexible/bendable display is changed from its first configuration to its second configuration by pivoting, bending, or straightening a ventral portion of the second flexible/bendable display away from the circumference of the band; and wherein the second flexible/bendable display is changed from its second configuration to its third configuration by being rotated around the housing or on a rotating housing (by approximately 90 degrees).

For example, a wrist-worn computing device with a multi-configuration display can comprise: a band which is worn on a person's wrist and/or lower arm; a housing which is attached by the band to the dorsal side of the wrist and/or lower arm; a flexible/bendable display which is attached to the housing and/or the band; wherein the flexible/bendable display has a first configuration in which the flexible/bendable display is arcuate and at least partially curves around a lateral (e.g. right or left) portion of the circumference of the band; wherein the flexible/bendable display has a second configuration in which the flexible/bendable display is substantially planar and extends straight outward from the band and/or the housing in a lateral (e.g. right or left) direction in a plane which is substantially coplanar with the housing and/or substantially tangential to the circumference of the band; wherein the flexible/bendable display is moved from its first configuration to its second configuration by pivoting, tilting, and/or straightening a ventral portion of the flexible/bendable display away from the band; wherein the flexible/bendable display has a third configuration in which the flexible/bendable display is substantially planar and extends straight outward from the band and/or the housing in a distal or proximal direction in a plane which is substantially coplanar with the housing and/or substantially tangential to the circumference of the band; and wherein the flexible/bendable display is moved from its second configuration to its third configuration by being rotated (approximately 90 degrees) around the housing and/or around a rotating joint on the band. Alternatively, a wrist-worn computing device with a multi-configuration display can comprise: a band which is worn on a person's wrist and/or lower arm; a right display which is attached by a first rotational joint to the right-dorsal quadrant of the band circumference; a left display which is attached by a second rotational joint to the left-dorsal quadrant of the band circumference; wherein the device has a first configuration in which the right and left displays lie along the circumference of the band; wherein the device has a second configuration in which the right and left displays extend out from the band in lateral (right and left) directions, respectively; wherein the device has a third configuration in which the right and left displays extend out from the band in proximal and distal directions, respectively; wherein the right and left displays are changed from the first configuration to the second configuration by pivoting, bending, or straightening their ventral portions away from the circumference of the band; wherein the right and left displays are changed from the second configuration to the third configuration by rotating them clockwise and counterclockwise, respectively, around the first and second rotational joints, respectively.

In an example, a wrist-worn computing device with a multi-configuration display can comprise: a band which is worn on a person's wrist and/or lower arm; a housing which is attached by the band to the dorsal side of the person's wrist and/or lower arm; a right display which is attached to the right side of the housing; a left display which is attached to the left side of the housing; wherein the device has a first configuration in which the right and left displays lie along the circumference of the band; wherein the device has a second configuration in which the right and left displays extend out from the band in lateral (right and left) directions, respectively; wherein the device has a third configuration in which the right and left displays both extend out from the band in a proximal direction; wherein the right and left displays are changed from the first configuration to the second configuration by pivoting, bending, or straightening their ventral portions away from the circumference of the band; wherein the right and left displays are changed from the second configuration to the third configuration by rotating them (90 degrees) around the housing, respectively.

In an example, a wrist-worn computing device with a multi-configuration display can comprise: a band which is worn on a person's wrist and/or lower arm; a housing which is attached by the band to the dorsal side of the wrist and/or lower arm; a rotating portion (such as a ring or bezel) of the housing, wherein the rotating portion of the housing rotates in a virtual plane which is substantially parallel to the virtual plane which best fits the rest of the housing and/or is substantially parallel to a virtual plane which is tangential to the circumference of the band; one or more displays which are attached to the rotating portion of the housing; wherein the one or more displays have a first configuration in which the one or more displays curve around a lateral (e.g. right or left) portion of the circumference of the band; wherein the one or more displays have a second configuration in which the one or more displays extend outward from the rotating portion in a lateral (e.g. right and/or left) direction; wherein the one or more displays have a second configuration in which the one or more displays extend outward from the rotating portion in a proximal (closer to the person's elbow) and/or distal (farther from the person's elbow) direction; wherein the one or more displays are moved from their first configuration to their second configuration by pivoting, tilting, and/or straightening a ventral portion of the one or more displays away from the circumference of the band; and wherein the one or more displays are moved from their second configuration to their third configuration by rotating the rotating portion of the housing.

For example, a wrist-worn computing device (such as a smart watch) with a multi-configuration display can comprise: a band which is worn on a person's wrist and/or lower arm; a housing which is attached by the band to the dorsal side of the wrist and/or lower arm; a rotating ring or bezel around the housing; one or more displays which are attached to the rotating ring or bezel; wherein the one or more displays have a first configuration in which the one or more displays at least partially span a lateral (e.g. right or left) portion of the band; wherein the one or more displays have a second configuration in which the one or more displays extend outward from the ring or bezel in a lateral (e.g. right or left) direction in a plane which is substantially coplanar with the housing and/or substantially tangential to the circumference of the band; wherein the one or more displays are moved from their first configuration to their second configuration by pivoting, tilting, and/or straightening a ventral portion of the one or more displays away from the band; wherein the one or more displays have a third configuration in which the one or more displays extend outward from the ring or bezel in a distal or proximal direction in a plane which is substantially coplanar with the housing and/or substantially tangential to the circumference of the band; and wherein the one or more displays are moved from their second configuration to their third configuration by rotating the ring or bezel around the housing.

In an example, a wrist-worn computing device with a multi-configuration display can comprise: a band which is worn on a person's wrist and/or lower arm; a first display which is attached to a first lateral (e.g. right or left) side of the band by a rotating joint or axle; a second display which is attached to a second lateral (e.g. left or right) side of the band by a rotating joint or axle, wherein the second lateral side is opposite the first lateral side; wherein the first display has a first configuration in which it spans at least part of a first lateral (right or left) portion of the circumference of the band; wherein the first display has a second configuration in which it extends straight outward from the housing in a lateral (right or left) manner in a plane which is substantially coplanar with the housing and/or substantially tangential to the circumference of the band; wherein the first display has a third configuration in which it extends straight outward from the housing in a proximal (closer to the person's elbow) or distal (farther from the person's elbow) manner in a plane which is substantially coplanar with the housing and/or substantially tangential to the circumference of the band; wherein the first display is changed from its first configuration to its second configuration by pivoting, bending, or straightening a ventral portion of the first display away from the circumference of the band; wherein the first display is changed from its second configuration to its third configuration by being rotated around a joint or axle on the band (by approximately 90 degrees); wherein the second display has a first configuration in which it spans at least part of a second lateral (left or right) portion of the circumference of the band, wherein the second lateral side is opposite the first lateral side; wherein the second display has a second configuration in which it extends straight outward from the housing in a lateral (right or left) manner in a plane which is substantially coplanar with the housing and/or substantially tangential to the circumference of the band; wherein the second display has a third configuration in which it extends straight outward from the housing in a proximal (closer to the person's elbow) or distal (farther from the person's elbow) manner in a plane which is substantially coplanar with the housing and/or substantially tangential to the circumference of the band; wherein the second display is changed from its first configuration to its second configuration by pivoting, bending, or straightening a ventral portion of the second display away from the circumference of the band; and wherein the second display is changed from its second configuration is changed from its second configuration to its third configuration by being rotated around a joint or axle on the band (by approximately 90 degrees).

In another embodiment, a wrist-worn computing device (such as a smart watch) with a multi-configuration display can comprise: a band which is worn around a person's wrist and/or lower arm, wherein the band further comprises a proximal ring with a circumferentially-variable width and a distal ring with a circumferentially-variable width, wherein one of the rings can be rotated relative to the other ring around the person's wrist and/or lower arm; a first display which is attached to the proximal ring on a wide portion of the proximal ring; and a second display which is attached to the distal ring, wherein the distal perimeter of the second display extends out from the distal ring in a distal manner; wherein the device has a first configuration in which the first and second displays are on opposite sides of the person's wrist and/or lower arm; wherein the device has a second configuration in which the first and second displays are aligned on the same side of the person's wrist and/or lower arm to form a (large) combined display; and wherein the device is changed from its first configuration to its second configuration by rotating one of the rings relative to the other ring. In another example, a wrist-worn computing device with a multi-configuration display can comprise: a band which is worn on a person's wrist and/or lower arm; a housing which is attached by the band to the dorsal side of the wrist and/or lower arm; one or more displays; wherein the one or more displays have a first configuration in which the one or more displays at least partially span a lateral (e.g. right or left) portion of the band; wherein the one or more displays have a second configuration in which the one or more displays extend outward from the band and/or the housing in a lateral (e.g. right or left) direction in a plane which is substantially coplanar with the housing and/or substantially tangential to the circumference of the band; wherein the one or more displays are moved from their first configuration to their second configuration by pivoting, tilting, and/or straightening a ventral portion of the one or more displays away from the band; wherein the one or more displays have a third configuration in which the one or more displays extend outward from the band and/or the housing in a distal or proximal direction in a plane which is substantially coplanar with the housing and/or substantially tangential to the circumference of the band; and wherein the one or more displays are moved from their second configuration to their third configuration by being rotated around the housing and/or around a rotating joint on the band.

In an example, a wrist-worn computing device with a multi-configuration display can comprise: a housing which is worn on the dorsal surface of a person's wrist and/or lower arm; wherein the housing further comprises a base portion and a movable portion; wherein a first edge of the moveable portion is moveably attached to the base portion; wherein the device has a first configuration in which the movable portion is folded over the base portion; wherein the device has a second configuration in which the movable portion is unfolded from the base portion by moving a second edge of the movable portion away from the base portion in a proximal direction (closer to the person's elbow); wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is worn on a person's wrist and/or lower arm; wherein the housing further comprises a base portion and a movable portion; wherein a first edge of the moveable portion is moveably attached to the base portion; wherein the device has a first configuration in which the movable portion is folded over the base portion; wherein the device has a second configuration in which the movable portion is unfolded from the base portion by moving a second edge of the movable portion away from the base portion, and wherein the second edge is opposite the first edge; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a band which is worn on a person's wrist and/or lower arm; wherein the band further comprises a first ring around the person's wrist and/or lower arm; wherein the band further comprises a second ring around the person's wrist and/or lower arm; wherein the band further comprises a stretchable mesh (or fabric) between the first ring and the second ring; a housing which is attached to the first ring; a first display on the housing; and a second display which is attached to the second ring; wherein the device has a first configuration in which the second display is substantially inside the housing and the stretchable mesh (or fabric) has a first width; wherein the device has a second configuration in which the second display is substantially outside the housing and the stretchable mesh (or fabric) has a second width, wherein the second width is greater than the first width. Alternatively, a wrist-worn computing device (such as a smart watch) with a multi-configuration display can comprise: a band which is worn on a person's wrist and/or lower arm; a connected series of displays which is attached to the dorsal side of the band and/or to a housing on the dorsal side of the band; wherein the connected series of displays has a first configuration in which the connected series of displays curve around a lateral (right or left) portion of the circumference of the band; wherein the connected series of displays has a second configuration in which the connected series of displays stick out in a lateral (right and/or left) manner from the dorsal side of the band and/or the housing on the dorsal side of the band; wherein the connected series of displays has a third configuration in which the connected series of displays stick out in a proximal (closer to the person's elbow) and/or distal (farther from the person's elbow) manner from the dorsal side of the band and/or the housing on the dorsal side of the band; wherein the connected series of displays is changed from its first configuration to its second configuration by moving (e.g. pivoting, bending, unfolding, or lifting) an end of the connected series of displays away from the circumference of the band; wherein the connected series of displays is changed from its second configuration to its third configuration by rotating (the end of) the connected series of displays around the dorsal side of the band and/or around the housing on the dorsal side of the band.

In an example, a wrist-worn computing device with a multi-configuration display can comprise: a housing (such as a smart watch) which is worn on a person's wrist and/or lower arm; wherein the housing further comprises a base portion and a sliding extension; wherein the device has a first configuration in which at least 90% of the sliding extension is on top of the base portion; wherein the device has a second configuration in which at least 90% of the sliding extension is laterally adjacent to the base portion in a proximal, distal, right-lateral, or left-lateral direction; a first display on the housing; and a second display on the sliding extension. In another example, a wrist-worn computing device (such as a smart watch) with a multi-configuration display can comprise: a housing (such as a smart watch) which is worn on a person's wrist and/or lower arm; wherein the housing further comprises a base portion and a sliding extension; wherein the device has a first configuration in which at least half of the sliding extension is on top of the base portion; wherein the device has a second configuration in which at least half of the sliding extension is laterally adjacent to the base portion in a proximal, distal, right-lateral, or left-lateral direction; a first display on the housing; and a second display on the sliding extension.

In an example, a wrist-worn computing device with a multi-configuration display can comprise: a housing (such as a smart watch) which is worn on the dorsal surface of a person's wrist and/or lower arm; wherein the housing further comprises a sliding extension; wherein the device has a first configuration in which at least three-quarters of the sliding extension is on top of the rest of the housing; wherein the device has a second configuration in which at least three-quarters of the sliding extension extends laterally outward in a distal, proximal, right-lateral, or left-lateral direction from the rest of the housing; wherein the sliding extension remains in substantially the same virtual plane in both the first configuration and the second configuration as well as in the transition from the first configuration to the second configuration; wherein the sliding extension is moved from the first configuration to the second configuration by an electromagnetic actuator or by a mechanical spring; a first quadrilateral display with rounded corners on the housing; and a second quadrilateral display with rounded corners on the sliding extension. Alternatively, a wrist-worn computing device with a multi-configuration display can comprise: a housing (such as a smart watch) which is worn on a person's wrist and/or lower arm; wherein the housing further comprises a sliding extension; wherein the device has a first configuration in which at least three-quarters of the sliding extension is on top of the rest of the housing; wherein the device has a second configuration in which at least three-quarters of the sliding extension extends laterally outward from the rest of the housing; a first quadrilateral display with rounded corners on the housing; and a second quadrilateral display with rounded corners on the sliding extension.

In another embodiment, a wrist-worn computing device with a multi-configuration display can comprise: a housing (such as a smart watch) which is worn on a person's wrist and/or lower arm; wherein the housing further comprises a sliding extension; wherein the device has a first configuration in which at least three-quarters of the sliding extension is inside the rest of the housing; wherein the device has a second configuration in which at least three-quarters of the sliding extension extends laterally outward from the rest of the housing; wherein the sliding extension remains in substantially the same virtual plane in both the first configuration and the second configuration as well as in the transition from the first configuration to the second configuration; a first quadrilateral display with rounded corners on the housing; and a second quadrilateral display with rounded corners on the sliding extension. In another example, a wrist-worn computing device with a multi-configuration display can comprise: a band with a stretchable and/or expandable mesh (or fabric), wherein the band is worn around a person's wrist and/or lower arm; a plurality of displays which are attached to the band; wherein the device has a first configuration in which displays in the plurality of displays collectively span a first lateral width and the band has a second lateral width; wherein the device has a second configuration in which displays in the plurality of displays collectively span a third lateral width and the band has a fourth lateral width; wherein the third lateral width is at least 50% greater than the first lateral width and the fourth lateral width is at least 50% greater than the second lateral width; and where the device is changed from its first configuration to its second configuration by sliding one or more displays in a proximal direction (e.g. closer to the person's elbow) and expanding the width of the band in the proximal direction.

For example, a wrist-worn computing device (such as a smart watch) with a multi-configuration display can comprise: a band with a stretchable and/or expandable mesh (or fabric), wherein the band is worn around a person's wrist and/or lower arm; a plurality of displays which are attached to the band; wherein the device has a first configuration in which displays in the plurality of displays collectively span a first lateral width and the band has a second lateral width; wherein the device has a second configuration in which displays in the plurality of displays collectively span a third lateral width and the band has a fourth lateral width; wherein the third lateral width is at least 50% greater than the first lateral width and the fourth lateral width is at least 50% greater than the second lateral width; and where the device is changed from its first configuration to its second configuration by un-telescoping one or more displays in proximal and/or distal direction(s) and expanding the width of the band in proximal and/or distal direction(s). In another example, a wrist-worn computing device with a multi-configuration display can comprise: a variable-width band which is worn around a person's wrist and/or lower arm; a plurality of displays which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by sliding one or more displays in a distal direction relative to the other displays and by expanding and/or stretching the band in a distal direction.

In an example, a wrist-worn computing device (such as a smart watch) with a multi-configuration display can comprise: a variable-width band which is worn around a person's wrist and/or lower arm; a plurality of displays which are attached to the variable-width band; wherein the device has a first configuration in which displays in the plurality of displays are substantially on top of each other and the variable-width band has a first width; wherein the device has a second configuration in which displays in the plurality of displays are substantially laterally-adjacent to each other and the variable-width band has a second width. In another example, a wrist-worn computing device with a multi-configuration display can comprise: a variable-width band which is worn around a person's wrist and/or lower arm; a plurality of foldable displays which are attached to the band; wherein the device has a first configuration in which one or more displays in the plurality of foldable displays are folded over each other and the band has a first width; and wherein the device has a second configuration in which one or more displays in the plurality of foldable displays are unfolded and the band has a second width, wherein the second width is greater than the first width.

In an example, a wrist-worn computing device with a multi-configuration display can comprise: a band which is worn on a person's wrist and/or lower arm; and a connected series of displays which is attached to the band by a rotational joint on the dorsal side of the band; wherein the device has a first configuration in which the connected series of displays is arcuate and curves around the circumference of the band from the dorsal side of the band to a lateral (right or left) side of the band; wherein the device has a second configuration in which the connected series of displays is substantially planar and extends out from the band in a proximal direction; wherein the connected series of displays is changed from the first configuration to the second configuration by pivoting, bending, or straightening a ventral portion of the connected series of displays away from the circumference of the band; and wherein the connected series of displays is changed from the second configuration to the third configuration by rotating the connected series of displays (by 90 degrees) around the rotational joint. Alternatively, a wrist-worn computing device with a multi-configuration display can comprise: a housing which is worn on a person's wrist and/or lower arm; wherein the housing further comprises a base portion and a movable portion whose proximal edge is attached to the base portion; wherein the device has a first configuration in which the movable portion is parallel to and above the base portion; wherein the device has a second configuration in which the distal edge of the movable portion is pivoted, tilted, and/or rotated away from the base portion in an outward and proximal manner; wherein the device has a third configuration in which is the movable portion is coplanar with and adjacent to the base portion; wherein the movable portion has a first side and a second side which is opposite the first side; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on the dorsal surface of a person's wrist and/or lower arm; wherein the housing further comprises a base portion and a movable portion, wherein the moveable portion is moveably attached to the base portion; wherein the device has a first configuration in which the movable portion is folded over the base portion; wherein the device has a second configuration in which the movable portion is unfolded from the base portion; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces radially away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device (such as a smart watch) with a multi-configuration display can comprise: a housing which is worn on the dorsal surface of a person's wrist and/or lower arm; wherein the housing further comprises a base portion and a movable portion, wherein the moveable portion is moveably attached to the base portion; wherein the device has a first configuration in which the movable portion is folded over the base portion; wherein the device has a second configuration in which the movable portion is unfolded from the base portion; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces radially away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a housing which is worn on a person's wrist and/or lower arm; wherein the housing further comprises a base portion and a movable portion whose distal edge is attached to the base portion; wherein the device has a first configuration in which the movable portion is parallel to and above the base portion; wherein the device has a second configuration in which the proximal edge of the movable portion is pivoted, tilted, and/or rotated away from the base portion in an outward and distal manner; wherein the device has a third configuration in which is the movable portion is coplanar with and adjacent to the base portion; wherein the movable portion has a first side and a second side which is opposite the first side; a first display (or portion of a display) on the first side of the movable portion; a second display (or portion of a display) on the second side of the movable portion; and a third display (or portion of a display) on the base portion. In another example, a wrist-worn computing device (such as a smart watch) with a multi-configuration display can comprise: a housing (such as a smart watch) which is worn on a person's wrist and/or lower arm; wherein the housing further comprises a base portion and a sliding extension; wherein the device has a first configuration in which the sliding extension is on top of the base portion; wherein the device has a second configuration in which the sliding extension is extended outward from the base portion in a distal direction; a first display on the housing; and a second display on the sliding extension.

In another embodiment, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is on top of the rest of the housing; wherein the device has a second configuration in which the sliding extension extends out from the rest of the housing; a first display on the housing; and a second display on the sliding extension. In another example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially inside the rest of the housing; wherein the device has a second configuration in which the sliding extension extends in a coplanar manner outward from the rest of the housing; a first display on the housing; and a second display on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially inside the rest of the housing; wherein the device has a second configuration in which the sliding extension extends in a parallel manner outward from the rest of the housing; a first display on the housing; and a second display on the sliding extension. Alternatively, a wrist-worn computing device (such as a smart watch) with a multi-configuration display can comprise: a housing (such as a smart watch) which is worn on a person's wrist and/or lower arm; wherein the housing further comprises a sliding extension; wherein the device has a first configuration in which the sliding extension is inside the housing; wherein the device has a second configuration in which the sliding extension extends outward from the rest of the housing; a first display on the housing; and a second display on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially on top of (or inside) the housing; wherein the device has a second configuration in which the sliding extension extends outward from the rest of the housing, wherein the virtual plane which best fits the sliding extension is substantially parallel to the virtual plane which best fits the housing in both the first configuration and the second configuration; a first display on the housing; and a second display on the sliding extension. In another example, a wrist-worn computing device (such as a smart watch) with a multi-configuration display can comprise: a housing (such as a smart watch) which is worn on a person's wrist and/or lower arm; wherein the housing further comprises a sliding extension; wherein the device has a first configuration in which the sliding extension is substantially on top of (or inside) the housing; wherein the device has a second configuration in which the sliding extension extends outward from the rest of the housing, wherein the sliding extension is moved from the first configuration to the second configuration by an electromagnetic actuator; a first display on the housing; and a second display on the sliding extension.

For example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially on top of (or inside) the housing; wherein the device has a second configuration in which the sliding extension extends outward from the rest of the housing, wherein the centroid of the sliding extension is moved in a right-lateral or left-lateral direction (e.g. perpendicular to the longitudinal axis of the person's lower arm) as the sliding extension is moved from the first configuration to the second configuration; a first display on the housing; and a second display on the sliding extension. In another example, a wrist-worn computing device with a multi-configuration display can comprise: a band which is worn on a person's wrist and/or lower arm; a display which is attached to the dorsal side of the band and/or to a housing on the dorsal side of the band; wherein the display has a first configuration in which the display at least partially spans a lateral (right or left) portion of the circumference of the band; wherein the display has a second configuration in which the display sticks out in a lateral (right and/or left) manner from the dorsal side of the band and/or the housing on the dorsal side of the band; wherein the display has a third configuration in which the display sticks out in a proximal (closer to the person's elbow) and/or distal (farther from the person's elbow) manner from the dorsal side of the band and/or the housing on the dorsal side of the band; wherein the display is changed from its first configuration to its second configuration by moving (e.g. pivoting, unfolding, or lifting) an end of the display away from the circumference of the band; wherein the display is changed from its second configuration to its third configuration by rotating (the end of) the display around the dorsal side of the band and/or around the housing on the dorsal side of the band.

In an example, a wrist-worn computing device with a multi-configuration display can comprise: a band which is worn on a person's wrist and/or lower arm; a flexible/bendable display which is attached to rotating joint or axle on the band; wherein the flexible/bendable display has a first configuration in which the flexible/bendable display is arcuate and at least partially curves around a lateral (e.g. right or left) portion of the circumference of the band; wherein the flexible/bendable display has a second configuration in which the flexible/bendable display is substantially planar and extends outward from the band in a lateral (e.g. right and/or left) direction in a plane which is substantially tangential to the circumference of the band; wherein the flexible/bendable display is moved from its first configuration to its second configuration by pivoting, tilting, and/or straightening a ventral portion of the flexible/bendable display away from the band; wherein the flexible/bendable display has a third configuration in which the flexible/bendable display is substantially planar and extends outward from the band in a distal and/or proximal direction in a plane which is substantially tangential to the circumference of the band; and wherein the flexible/bendable display are moved from its second configuration to its third configuration by being rotated (approximately 90 degrees) around the rotating joint or axle on the band. In another example, a wrist-worn computing device with a multi-configuration display can comprise: a band which is worn on a person's wrist and/or lower arm; a flexible/bendable display which is attached to a rotating joint or axle on the band; wherein the flexible/bendable display has a first configuration which at least partially curves around a lateral (e.g. right or left) portion of the circumference of the band; wherein the flexible/bendable display has a second configuration which extends outward from the band in a lateral (e.g. right or left) direction in a plane which is substantially tangential to the circumference of the band; wherein the flexible/bendable display is moved from its first configuration to its second configuration by pivoting, tilting, and/or straightening an end (e.g. the ventral end) of the flexible/bendable display away from the band; wherein the flexible/bendable display has a third configuration in which the flexible/bendable display extends outward from the band in a distal or proximal direction in a plane which is substantially tangential to the circumference of the band; and wherein the flexible/bendable display is moved from its second configuration to its third configuration by being rotated (approximately 90 degrees) around the joint or axle on the band.

For example, a wrist-worn computing device (such as a smart watch) with a multi-configuration display can comprise: a band which is worn around at least a portion of the circumference of a person's wrist and/or lower arm; a housing attached to the band; wherein the housing further comprises a base portion and a movable portion which is attached to the base portion; wherein the device has a first configuration in which the movable portion is folded over the base portion and a second configuration in which the movable portion is unfolded away from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces substantially away from the wrist and/or lower arm in the second configuration, wherein the second side is opposite the first side; a first display (or portion of a display) on the first side of the movable portion; a second display (or portion of a display) on the second side of the movable portion; and a third display (or portion of a display) on the base portion. Alternatively, a wrist-worn computing device with a multi-configuration display can comprise: a band which is worn on a person's wrist and/or lower arm; a housing which is attached to the band; wherein the housing further comprises a base portion and a movable portion, wherein one edge of the moveable portion is moveably attached to the base portion by a hinge, joint, strap, band, cord, or membrane; wherein the device has a first configuration in which the movable portion is folded over the base portion; wherein the device has a second configuration in which the movable portion is unfolded from the base portion; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In another embodiment, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first (single-display) configuration in which the movable portion is folded over the base portion; wherein the device has a second (multi-display) configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is attached by a band to a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and distal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In another embodiment, a wrist-worn computing device (such as a smart watch) with a multi-configuration display can comprise: a housing which is worn on the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and distal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration. In another example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded in an outward and distal direction (away from the person's elbow) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a housing which is attached by a band to a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and proximal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is worn on the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and proximal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded in a proximal direction (toward the person's elbow) away from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device (such as a smart watch) with a multi-configuration display can comprise: a housing which is attached by a band to a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is attached by a band to the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward around the hinge, joint, strap, band, cord, or membrane to a location which is lateral relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device (such as a smart watch) with a multi-configuration display can comprise: a housing which is attached by a band to the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which the movable portion is unfolded (e.g. pivoted, tilted, flipped, and/or rotated) outward around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display on the first side of the movable portion; a first portion of a second display on the second side of the movable portion; and a second portion of the second display on the base portion. In another example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded away from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In another embodiment, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded in a lateral direction (perpendicular to the longitudinal axis of the person's lower arm) away from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over the base portion; wherein the device has a second configuration in which the movable portion is unfolded (e.g. pivoted, tilted, flipped, and/or rotated) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. Alternatively, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In another embodiment, a wrist-worn computing device with a multi-configuration display can comprise: a housing which is worn on the dorsal surface of a person's wrist and/or lower arm; wherein the housing further comprises a base portion; wherein the housing further comprises a movable portion which is movably attached to the base portion; wherein the device has a first configuration in which the movable portion is folded over the base portion and substantially parallel to the base portion; wherein the device has a second configuration in which the movable portion is unfolded from the base portion, substantially coplanar with the base portion, and adjacent to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a housing which is worn on a person's wrist and/or lower arm; wherein the housing further comprises a base portion which is a first distance from the surface of the person's wrist and/or lower arm; wherein the housing further comprises a movable portion which is movably attached to the base portion and is a second distance from the surface of the person's wrist and/or lower arm, wherein the second distance is greater than the first distance; wherein the device has a first configuration in which the movable portion is folded over the base portion; wherein the device has a second configuration in which the movable portion is unfolded from the base portion; wherein the movable portion has a first side which faces generally away from the wrist and/or lower arm in the first configuration and faces generally toward the wrist and/or lower arm in the second configuration; wherein the movable portion has a second side which faces generally toward the wrist and/or lower arm in the first configuration and faces generally away from the wrist and/or lower arm in the second configuration; a first quadrilateral display (with rounded corners) on the first side of the movable portion; a second quadrilateral display (with rounded corners) on the second side of the movable portion; and a third (round corner) quadrilateral display on the base portion.

In an example, a wrist-worn computing device with a multi-configuration display can comprise: a housing which is worn on a person's wrist and/or lower arm; wherein the housing further comprises a base portion which is a first distance from the surface of the person's wrist and/or lower arm; wherein the housing further comprises a movable portion which is movably attached to the base portion and is a second distance from the surface of the person's wrist and/or lower arm, wherein the second distance is greater than the first distance; wherein the device has a single-part-display configuration in which the movable portion is folded over the base portion; wherein the device has a multi-part-display configuration in which the movable portion is unfolded from the base portion; wherein the movable portion has a first side which faces generally away from the wrist and/or lower arm in the single-part-display configuration and faces generally toward the wrist and/or lower arm in the multi-part-display configuration; wherein the movable portion has a second side which faces generally toward the wrist and/or lower arm in the single-part-display configuration and faces generally away from the wrist and/or lower arm in the multi-part-display configuration; a first quadrilateral display (with rounded corners) on the first side of the movable portion; a first portion of a quadrilateral display (with rounded corners) on the second side of the movable portion; and a second portion of a (round corner) quadrilateral display on the base portion. In another example, a wrist-worn computing device with a multi-configuration display can comprise: a housing which is worn on the dorsal surface of a person's wrist and/or lower arm; wherein the housing further comprises a lower base portion; wherein the housing further comprises a upper movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device (such as a smart watch) with a multi-configuration display can comprise: a smart watch which is worn on the dorsal surface of a person's wrist and/or lower arm; wherein the smart watch further comprises a lower base portion; wherein the housing further comprises a upper movable portion, wherein the proximal (e.g. closer to the person's elbow) edge of the upper moveable portion is movably and/or flexibly attached to the lower base portion by a hinge, joint, strap, band, cord, or membrane; wherein the device has a single-display configuration in which the movable portion is folded over the base portion; wherein the device has a multi-display configuration in which the movable portion is unfolded from the base portion by pivoting, tilting, and/or rotating the distal (e.g. farther from the person's elbow) edge of the movable portion away from the base portion; wherein the movable portion has a first side which faces generally away from the wrist in the single-display configuration and faces generally toward the wrist and/or lower arm in the multi-display configuration; wherein the movable portion has a second side which faces generally toward the wrist and/or lower arm in the single-display configuration and faces generally away from the wrist in the multi-display configuration; a first display on the first side of the movable portion; a second display (or portion of a multi-part display) on the second side of the movable portion; and a third display (or portion of a multi-part display) on the base portion. In another example, a wrist-worn computing device with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over the base portion; wherein the device has a second configuration in which an edge of the movable portion is unfolded in an outward and distal direction relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device (such as a smart watch) with a multi-configuration display can comprise: a housing which is worn on a person's wrist and/or lower arm; wherein the housing further comprises a base portion and a movable portion; wherein the moveable portion is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and proximal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration. In another example, a wrist-worn computing device with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over the base portion; wherein the device has a second configuration in which the movable portion is unfolded from the base portion; wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a first portion of a second display (or portion of a display) on the second side of the movable portion; and a second portion of the second display (or portion of a display) on the base portion.

In an example, a wrist-worn computing device (such as a smart watch) with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over the base portion; wherein the device has a second configuration in which the movable portion is unfolded outward relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a band which is worn on a person's wrist and/or lower arm; one or more displays which are attached to a rotating joint or axle on the band; wherein the one or more displays have a first configuration in which the one or more displays are arcuate and at least partially curve around a portion of the circumference of the band; wherein the one or more displays have a second configuration in which the one or more displays are substantially planar and extend straight outward from the band and/or the housing in a lateral (e.g. right or left) direction in a plane which is substantially coplanar with the housing and/or substantially tangential to the circumference of the band; wherein the one or more displays are moved from their first configuration to their second configuration by moving an end portion of the one or more displays away from the band; wherein the one or more displays have a third configuration in which the one or more displays are substantially planar and extend straight outward from the band and/or the housing in a distal or proximal direction in a plane which is substantially coplanar with the housing and/or substantially tangential to the circumference of the band; and wherein the one or more displays are moved from their second configuration to their third configuration by being rotated (approximately 90 degrees) around the rotating joint or axle on the band.

In an example, a wrist-worn computing device with a multi-configuration display can comprise: a band which is worn on a person's wrist and/or lower arm; one or more displays which are attached to the dorsal side of the band and/or to a housing on the dorsal side of the band; wherein the one or more displays have a first configuration in which the one or more displays curve around a lateral (right or left) portion of the circumference of the band; wherein the one or more displays have a second configuration in which the one or more displays stick straight out (like one or more wings) in a lateral (right and/or left) manner from the dorsal side of the band and/or the housing on the dorsal side of the band; wherein the one or more displays have a third configuration in which the one or more displays stick straight out in a proximal (closer to the person's elbow) and/or distal (farther from the person's elbow) manner from the dorsal side of the band and/or the housing on the dorsal side of the band; wherein the one or more displays are changed from their first configuration to their second configuration by detaching an end and moving (e.g. pivoting, bending, unfolding, or lifting) the one or more displays away from the circumference of the band; wherein the one or more displays are changed from their second configuration to their third configuration by rotating (the end of) the one or more displays around the dorsal side of the band and/or around the housing on the dorsal side of the band. Alternatively, a wrist-worn computing device with a multi-configuration display can comprise: a proximal band with wide and narrow portions around its circumference which is worn around a person's wrist and/or lower arm; a distal band which is worn around the person's wrist and/or lower arm; wherein the proximal band and the distal band are attached to each other in a manner which allows one band to rotate relative to the other band; a first display which is attached to the wide portion of the proximal band; a second display which is attached to the distal band; wherein the device has a first configuration in which the first display and the second display are on different sides of the person's wrist and/or lower arm; wherein the device has a second configuration in which the first display and the second display are (aligned) on the same side of the person's wrist in order to form a (large) combined display; and wherein the device is changed from its first configuration to its second configuration by rotating one of the bands relative to the other band.

For example, a wrist-worn computing device with a multi-configuration display can comprise: a housing which is worn on a person's wrist and/or lower arm; wherein the housing further comprises a base portion which is a first distance from the surface of the person's wrist and/or lower arm and a movable portion which is a second distance from the surface of the person's wrist and/or lower arm, wherein the second distance is greater than the first distance; wherein the right-lateral edge of the moveable portion is movably attached to the base portion by a hinge, joint, strap, band, cord, or membrane, wherein lateral means perpendicular to the longitudinal axis of a person's lower arm; wherein the device has a first configuration in which the movable portion is folded over the base portion (being substantially parallel to and above the base portion); wherein the device has a second configuration in which the movable portion is unfolded from the base portion (being substantially coplanar with and adjacent to the base portion); wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion.

In another embodiment, a wrist-worn computing device (such as a smart watch) with a multi-configuration display can comprise: a band which is worn on a person's wrist and/or lower arm; a housing which is attached by the band to the dorsal side of the wrist and/or lower arm; a chain of displays which is attached to the housing and/or the band; wherein the chain of displays has a first configuration in which the chain of displays is arcuate and at least partially curves around a lateral (e.g. right or left) portion of the circumference of the band; wherein the chain of displays has a second configuration in which the chain of displays is substantially planar and extends straight outward from the band and/or the housing in a lateral (e.g. right or left) direction in a plane which is substantially coplanar with the housing and/or substantially tangential to the circumference of the band; wherein the chain of displays is moved from its first configuration to its second configuration by moving an end (e.g. the ventral end) of the chain of displays away from the band; wherein the chain of displays has a third configuration in which the chain of displays is substantially planar and extends straight outward from the band and/or the housing in a distal or proximal direction in a plane which is substantially coplanar with the housing and/or substantially tangential to the circumference of the band; and wherein the chain of displays is moved from its second configuration to its third configuration by being rotated (approximately 90 degrees) around the housing and/or around a rotating joint on the band.

In an example, a wrist-worn computing device with a multi-configuration display can comprise: a band which is worn on a person's wrist and/or lower arm; a housing which is attached by the band to the dorsal side of the wrist and/or lower arm; a connected array of displays; wherein the connected array of displays has a first configuration in which the connected array of displays is arcuate and at least partially curves around a lateral (e.g. right or left) portion of the circumference of the band; wherein the connected array of displays has a second configuration in which the connected array of displays extends straight outward from the band and/or the housing in a lateral (e.g. right or left) direction in a plane which is substantially coplanar with the housing and/or substantially tangential to the circumference of the band; wherein the connected array of displays is moved from its first configuration to its second configuration by pivoting, tilting, and/or straightening a ventral portion of the connected array of displays away from the band; wherein the connected array of displays has a third configuration in which the connected array of displays extends straight outward from the band and/or the housing in a distal or proximal direction in a plane which is substantially coplanar with the housing and/or substantially tangential to the circumference of the band; and wherein the connected array of displays is moved from its second configuration to its third configuration by being rotated (approximately 90 degrees) around the housing and/or around a rotating joint on the band.

For example, a wrist-worn computing device (such as a smart watch) with a multi-configuration display can comprise: a band which is worn on a person's wrist and/or lower arm; a housing which is attached by the band to the dorsal side of the wrist and/or lower arm; a connected series of displays; wherein the connected series of displays has a first configuration in which the connected series of displays at least partially spans a lateral (e.g. right or left) side of the band; wherein the connected series of displays has a second configuration in which the connected series of displays extends straight outward from the band and/or the housing in a lateral (e.g. right or left) direction in a plane which is substantially coplanar with the housing and/or substantially tangential to the circumference of the band; wherein the connected series of displays is moved from its first configuration to its second configuration by pivoting, tilting, and/or straightening out a ventral portion of the connected series of displays away from the band; wherein the connected series of displays has a third configuration in which the connected series of displays extends straight outward from the band and/or the housing in a distal or proximal direction in a plane which is substantially coplanar with the housing and/or substantially tangential to the circumference of the band; and wherein the connected series of displays is moved from its second configuration to its third configuration by being rotated (approximately 90 degrees) around the housing and/or around a rotating joint on the band.

In another embodiment, a wrist-worn computing device with a multi-configuration display can comprise: a band which is worn on a person's wrist and/or lower arm; a housing which is attached by the band to the dorsal side of the wrist and/or lower arm; a display which is attached to the housing and/or the band; wherein the display has a first configuration in which the display is arcuate and at least partially curves around a lateral (e.g. right or left) portion of the circumference of the band; wherein the display has a second configuration in which the display extends outward from the band and/or the housing in a lateral (e.g. right or left) direction in a plane which is substantially coplanar with the housing and/or substantially tangential to the circumference of the band; wherein the display is moved from its first configuration to its second configuration by pivoting, tilting, and/or straightening a ventral portion of the display away from the band; wherein the display has a third configuration in which the display extends outward from the band and/or the housing in a distal or proximal direction in a plane which is substantially coplanar with the housing and/or substantially tangential to the circumference of the band; and wherein the display is moved from its second configuration to its third configuration by being rotated (approximately 90 degrees) around the housing and/or around a rotating joint on the band. In another example, a wrist-worn computing device (such as a smart watch) with a multi-configuration display can comprise: a band which is worn on a person's wrist and/or lower arm; a housing which is attached by the band to the dorsal side of the wrist and/or lower arm; a display which is movably attached to the housing and/or the band; wherein the display has a first configuration in which the display at least partially spans a lateral (e.g. right or left) side of the band; wherein the display has a second configuration in which the display extends outward from the band and/or the housing in a lateral (e.g. right or left) direction in a plane which is substantially coplanar with the housing and/or substantially tangential to the circumference of the band; wherein the display is moved from its first configuration to its second configuration by pivoting, tilting, and/or straightening out a ventral portion of the display away from the band; wherein the display has a third configuration in which the display extends outward from the band and/or the housing in a distal or proximal direction in a plane which is substantially coplanar with the housing and/or substantially tangential to the circumference of the band; and wherein the display is moved from its second configuration to its third configuration by being rotated (approximately 90 degrees) around the housing and/or around a rotating joint on the band.

For example, a wrist-worn computing device with a multi-configuration display can comprise: a band which is worn on a person's wrist and/or lower arm; a housing which is attached by the band to the dorsal side of the person's wrist and/or arm; a first display; and a second display; wherein the device has a first configuration in which the first display is on top of the housing, the second display is on the housing under the first display, and the dorsal side of the band has a first width; wherein the device has a second configuration in which the first display extends out from the housing in a proximal (closer to the person's elbow) direction, the second display is on the housing, and the dorsal side of the band has a second width, wherein the second width is greater than the first width; and wherein the first display slides out from the housing in a proximal direction and the width of the dorsal side of the band expands as the device changes from the first configuration to the second configuration.

In an example, a wrist-worn computing device with a multi-configuration display can comprise: a band which is worn on a person's wrist and/or lower arm; a housing which is attached by the band to the dorsal side of the wrist and/or lower arm; a first display which is attached to a first lateral (e.g. right or left) side of the housing; a second display which is attached to a second lateral (e.g. left or right) side of the housing, wherein the second side of the housing is opposite the first side of the housing; wherein the first display has a first configuration in which it spans at least part of a first lateral (right or left) portion of the circumference of the band; wherein the first display has a second configuration in which it extends straight outward from the housing in a lateral (right or left) manner in a plane which is substantially coplanar with the housing and/or substantially tangential to the circumference of the band; wherein the first display has a third configuration in which it extends straight outward from the housing in a proximal (closer to the person's elbow) or distal (farther from the person's elbow) manner in a plane which is substantially coplanar with the housing and/or substantially tangential to the circumference of the band; wherein the first display is changed from its first configuration to its second configuration by pivoting, bending, or straightening a ventral portion of the first display away from the circumference of the band; wherein the first display is changed from its second configuration to its third configuration by rotating the housing (by approximately 90 degrees); wherein the second display has a first configuration in which it spans at least part of a second lateral (left or right) portion of the circumference of the band, wherein the second lateral side is opposite the first lateral side; wherein the second display has a second configuration in which it extends straight outward from the housing in a lateral (right or left) manner in a plane which is substantially coplanar with the housing and/or substantially tangential to the circumference of the band; wherein the second display has a third configuration in which it extends straight outward from the housing in a proximal (closer to the person's elbow) or distal (farther from the person's elbow) manner in a plane which is substantially coplanar with the housing and/or substantially tangential to the circumference of the band; wherein the second display is changed from its first configuration to its second configuration by pivoting, bending, or straightening a ventral portion of the second display away from the circumference of the band; and wherein the second display is changed from its second configuration to its third configuration by rotating the housing (by approximately 90 degrees).

In an example, a wrist-worn computing device with a multi-configuration display can comprise: a distal band which is worn around a person's wrist and/or lower arm; a proximal band which is worn around the person's wrist and/or lower arm, wherein the proximal band is closer to the person's elbow than the distal band, and wherein the proximal band can be rotated relative to the distal band (around the person's wrist and/or lower arm); a first display which is attached to the distal band; a second display which is attached to the proximal band; wherein the device has a first configuration in which the first display is on a first (e.g. dorsal) side of the person's wrist and/or lower arm and the second display is on a second (e.g. ventral) side of the person's wrist and/or arm, wherein the second side is opposite the first side; wherein the device has a second configuration in which the first display is on the first (e.g. dorsal) side of the person's wrist and/or lower arm and the second display is aligned with the first display on the first (e.g. dorsal) side of the person's wrist and/or arm; and wherein the device is changed from its first configuration to its second configuration by rotating the proximal band (180 degrees) relative to the distal band. In another example, a wrist-worn computing device (such as a smart watch) with a multi-configuration display can comprise: a band which is worn on a person's wrist and/or lower arm; a housing which is attached by the band to the dorsal side of the wrist and/or lower arm; a flexible/bendable display; wherein the flexible/bendable display has a first configuration in which the flexible/bendable display is arcuate and curves around a lateral (e.g. right or left) portion of the circumference of the band; wherein the flexible/bendable display has a second configuration in which the flexible/bendable display extends outward from the band and/or the housing in a lateral (e.g. right or left) direction in a plane which is substantially coplanar with the housing and/or substantially tangential to the circumference of the band; wherein the flexible/bendable display is moved from its first configuration to its second configuration by detaching a ventral portion of the flexible/bendable display from the band and pivoting, tilting, and/or straightening out the ventral portion away from the band; wherein the flexible/bendable display has a third configuration in which the flexible/bendable display extends outward from the band and/or the housing in a distal or proximal direction in a plane which is substantially coplanar with the housing and/or substantially tangential to the circumference of the band; and wherein the flexible/bendable display is moved from its second configuration to its third configuration by being rotated (approximately 90 degrees) around the housing and/or around a rotating joint on the band.

For example, a wrist-worn computing device with a multi-configuration display can comprise: a band which is worn on a person's wrist and/or lower arm; a housing which is attached by the band to the dorsal side of the wrist and/or lower arm; a flexible/bendable display which is attached to the housing and/or the band; wherein the flexible/bendable display has a first configuration in which the flexible/bendable display is arcuate and at least partially curves around a lateral (e.g. right or left) side of the band; wherein the flexible/bendable display has a second configuration in which the flexible/bendable display is substantially planar and extends straight outward from the band and/or the housing in a lateral (e.g. right or left) direction in a plane which is substantially coplanar with the housing and/or substantially tangential to the circumference of the band; wherein the flexible/bendable display is moved from its first configuration to its second configuration by pivoting, tilting, and/or straightening a ventral portion of the flexible/bendable display away from the band; wherein the flexible/bendable display has a third configuration in which the flexible/bendable display is substantially planar and extends straight outward from the band and/or the housing in a distal or proximal direction in a plane which is substantially coplanar with the housing and/or substantially tangential to the circumference of the band; and wherein the flexible/bendable display is moved from its second configuration to its third configuration by being rotated (approximately 90 degrees) around the housing and/or around a rotating joint on the band.

In an example, a wrist-worn computing device (such as a smart watch) with a multi-configuration display can comprise: a band which is worn on a person's wrist and/or lower arm; a right display which is attached by a first rotational joint to the right-dorsal quadrant of the band circumference; a left display which is attached by a second rotational joint to the left-dorsal quadrant of the band circumference; wherein the device has a first configuration in which the right and left displays are arcuate and curve around the circumference of the band; wherein the device has a second configuration in which the right and left displays are substantially planar and extend out from the band in lateral (right and left) directions, respectively; wherein the device has a third configuration in which the right and left displays are substantially planar and extend out from the band in proximal and distal directions, respectively; wherein the right and left displays are changed from the first configuration to the second configuration by pivoting, bending, or straightening their ventral portions away from the circumference of the band; wherein the right and left displays are changed from the second configuration to the third configuration by rotating them (90 degrees) around the first and second rotational joints, respectively.

For example, a wrist-worn computing device with a multi-configuration display can comprise: a band which is worn on a person's wrist and/or lower arm; a rotating housing which is attached by the band to the dorsal side of the person's wrist and/or lower arm; a right display which is attached to the right side of the housing; a left display which is attached to the left side of the housing; wherein the device has a first configuration in which the right and left displays lie along the circumference of the band; wherein the device has a second configuration in which the right and left displays extend out from the band in lateral (right and left) directions, respectively; wherein the device has a third configuration in which the right and left displays extend out from the band in proximal and distal directions, respectively; wherein the right and left displays are changed from the first configuration to the second configuration by pivoting, bending, or straightening their ventral portions away from the circumference of the band; wherein the right and left displays are changed from the second configuration to the third configuration by rotating the housing (90 degrees).

In another example, a wrist-worn computing device with a multi-configuration display can comprise: a band which is worn on a person's wrist and/or lower arm; a housing which is attached by the band to the dorsal side of the wrist and/or lower arm; a rotating portion (such as a ring or bezel) of the housing, wherein the rotating portion of the housing rotates in a virtual plane which is substantially parallel to the virtual plane which best fits the rest of the housing and/or is substantially parallel to a virtual plane which is tangential to the circumference of the band; one or more displays which are attached to the rotating portion of the housing; wherein the one or more displays have a first configuration in which the one or more displays are arcuate and curve around a lateral (e.g. right or left) portion of the circumference of the band; wherein the one or more displays have a second configuration in which the one or more displays are substantially planar and extend outward from the rotating portion in a lateral (e.g. right and/or left) direction; wherein the one or more displays have a second configuration in which the one or more displays are substantially planar and extend outward from the rotating portion in a proximal (closer to the person's elbow) and/or distal (farther from the person's elbow) direction; wherein the one or more displays are moved from their first configuration to their second configuration by pivoting, tilting, and/or straightening a ventral portion of the one or more displays away from the circumference of the band; and wherein the one or more displays are moved from their second configuration to their third configuration by rotating the rotating portion of the housing.

In an example, a wrist-worn computing device with a multi-configuration display can comprise: a band which is worn on a person's wrist and/or lower arm; a housing which is attached to the dorsal side of band; a rotating ring or bezel around the housing; one or more displays which are attached to the rotating ring or bezel; wherein the one or more displays have a first configuration in which the one or more displays are arcuate and curve around a lateral (e.g. right or left) portion of the circumference of the band; wherein the one or more displays have a second configuration in which the one or more displays are substantially planar and extend outward from the ring or bezel in a lateral (e.g. right and/or left) direction in a plane which is substantially coplanar with the housing and/or substantially tangential to the circumference of the band; wherein the one or more displays have a third configuration in which the one or more displays are substantially planar and extend outward from the ring or bezel in a proximal (e.g. farther from the person's elbow) and/or distal (closer to the person's elbow) direction in a plane which is substantially coplanar with the housing and/or substantially tangential to the circumference of the band; wherein the one or more displays are moved from their first configuration to their second configuration by pivoting, tilting, and/or straightening a ventral portion of the one or more displays away from the band; and wherein the one or more displays are moved from their second configuration to their third configuration by rotating the ring or bezel (by approximately 90 degrees) around the housing.

In another embodiment, a wrist-worn computing device with a multi-configuration display can comprise: a band which is worn on a person's wrist and/or lower arm; a housing which is attached by the band to the dorsal side of the wrist and/or lower arm; a segmented display which is attached to the housing and/or the band; wherein the segmented display has a first configuration in which the segmented display is arcuate and curves around a lateral (e.g. right or left) portion of the circumference of the band; wherein the segmented display has a second configuration in which the segmented display extends outward from the band and/or the housing in a lateral (e.g. right or left) direction in a plane which is substantially coplanar with the housing and/or substantially tangential to the circumference of the band; wherein the segmented display is moved from its first configuration to its second configuration by detaching a ventral portion of the segmented display from the band and pivoting, tilting, and/or straightening out the ventral portion away from the band; wherein the segmented display has a third configuration in which the segmented display extends outward from the band and/or the housing in a distal or proximal direction in a plane which is substantially coplanar with the housing and/or substantially tangential to the circumference of the band; and wherein the segmented display is moved from its second configuration to its third configuration by being rotated (approximately 90 degrees) around the housing and/or around a rotating joint on the band.

For example, a wrist-worn computing device with a multi-configuration display can comprise: a band which is worn around a person's wrist and/or lower arm, wherein the band further comprises a proximal ring and a distal ring, wherein one of the rings can be rotated relative to the other ring around the person's wrist and/or lower arm; a first display which is attached to the proximal ring, wherein the proximal perimeter of the first display extends out from the proximal ring in a proximal manner; and a second display which is attached to the distal ring, wherein the distal perimeter of the second display extends out from the distal ring in a distal manner; wherein the device has a first configuration in which the first and second displays are on opposite sides of the person's wrist and/or lower arm; wherein the device has a second configuration in which the first and second displays are aligned on the same side of the person's wrist and/or lower arm to form a (large) combined display; and wherein the device is changed from its first configuration to its second configuration by rotating one of the rings relative to the other ring. Alternatively, a wrist-worn computing device (such as a smart watch) with a multi-configuration display can comprise: a band which is worn on a person's wrist and/or lower arm; a housing which is attached by the band to the dorsal side of the wrist and/or lower arm; one or more displays which are attached to the housing and/or the band; wherein the one or more displays have a first configuration in which the one or more displays at least partially span a lateral (e.g. right or left) portion of the circumference of the band; wherein the one or more displays have a second configuration in which the one or more displays are substantially planar and extend outward from the band and/or the housing in a lateral (e.g. right or left) direction in a plane which is substantially coplanar with the housing and/or substantially tangential to the circumference of the band; wherein the one or more displays are moved from their first configuration to their second configuration by pivoting, tilting, and/or straightening a ventral portion of the one or more displays away from the band; wherein the one or more displays have a third configuration in which the one or more displays are substantially planar and extend outward from the band and/or the housing in a distal or proximal direction in a plane which is substantially coplanar with the housing and/or substantially tangential to the circumference of the band; and wherein the one or more displays are moved from their second configuration to their third configuration by being rotated (approximately 90 degrees) around the housing and/or around a rotating joint on the band.

In an example, a wrist-worn computing device with a multi-configuration display can comprise: a housing which is worn on the dorsal surface of a person's wrist and/or lower arm; wherein the housing further comprises a base portion and a movable portion; wherein a first edge of the moveable portion is moveably attached to the base portion; wherein the device has a first configuration in which the movable portion is folded over the base portion; wherein the device has a second configuration in which the movable portion is unfolded from the base portion by moving a second edge of the movable portion away from the base portion in a distal direction (farther from the person's elbow); wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a band which is worn on a person's wrist and/or lower arm; wherein the band further comprises a proximal ring; wherein the band further comprises a distal ring; wherein the band further comprises a stretchable (and/or extendable) mesh between the proximal ring and the distal ring; a housing which is attached to the distal ring; a first display on the housing; and a second display which is attached to the proximal ring, wherein the second display slides into (and out of) the housing.

For example, a wrist-worn computing device with a multi-configuration display can comprise: a band which is worn on a person's wrist and/or lower arm; wherein the band further comprises a first ring around the person's wrist and/or lower arm; wherein the band further comprises a second ring around the person's wrist and/or lower arm; wherein the band further comprises a stretchable mesh (or fabric) between the first ring and the second ring; a first display which is attached to the first ring; and a second display which is attached to the second ring; wherein the device has a first configuration in which the second display is under the first display and the stretchable mesh (or fabric) has a first width; wherein the device has a second configuration in which the second display is laterally adjacent to the first display and the stretchable mesh (or fabric) has a second width, wherein the second width is greater than the first width. Alternatively, a wrist-worn computing device with a multi-configuration display can comprise: a housing (such as a smart watch) which is worn on a person's wrist and/or lower arm; wherein the housing further comprises a sliding extension; wherein the device has a first configuration in which at least 50% of the upper surface of the sliding extension is inside the housing; wherein the device has a second configuration in which at least 50% of the upper surface of the sliding extension is outside the housing; a first display on the housing; and a second display on the sliding extension.

In another embodiment, a wrist-worn computing device (such as a smart watch) with a multi-configuration display can comprise: a housing (such as a smart watch) which is worn on a person's wrist and/or lower arm; wherein the housing further comprises a sliding extension; wherein the device has a first configuration in which at least 90% of the sliding extension is inside the rest of the housing; wherein the device has a second configuration in which at least 90% of the sliding extension extends out from the rest of the housing (in a proximal, distal, right-lateral, or left-lateral direction); a first display on the housing; and a second display on the sliding extension. In another example, a wrist-worn computing device with a multi-configuration display can comprise: a housing (such as a smart watch) which is worn on a person's wrist and/or lower arm; wherein the housing further comprises a sliding extension; wherein the device has a first configuration in which at least half of the sliding extension is inside the rest of the housing; wherein the device has a second configuration in which at least half of the sliding extension extends out from the rest of the housing in a proximal, distal, right-lateral, or left-lateral direction; a first display on the housing; and a second display on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which at least three-quarters of the sliding extension is on top of the rest of the housing; wherein the device has a second configuration in which at least three-quarters of the sliding extension extends laterally outward in a distal, proximal, right-lateral, or left-lateral direction from the rest of the housing; wherein the sliding extension remains in substantially the same virtual plane in both the first configuration and the second configuration as well as in the transition from the first configuration to the second configuration; wherein the sliding extension is moved from the first configuration to the second configuration by an electromagnetic actuator or by a mechanical spring; a first quadrilateral display with rounded corners on the housing; and a second quadrilateral display with rounded corners on the sliding extension. In another example, a wrist-worn computing device with a multi-configuration display can comprise: a housing (such as a smart watch) which is worn on the dorsal surface of a person's wrist and/or lower arm; wherein the housing further comprises a sliding extension; wherein the device has a first configuration in which at least three-quarters of the sliding extension is inside the rest of the housing; wherein the device has a second configuration in which at least three-quarters of the sliding extension extends laterally outward in a distal, proximal, right-lateral, or left-lateral direction from the rest of the housing; wherein the sliding extension remains in substantially the same virtual plane in both the first configuration and the second configuration as well as in the transition from the first configuration to the second configuration; wherein the sliding extension is moved from the first configuration to the second configuration by an electromagnetic actuator or by a mechanical spring; a first quadrilateral display with rounded corners on the housing; and a second quadrilateral display with rounded corners on the sliding extension.

For example, a wrist-worn computing device with a multi-configuration display can comprise: a housing (such as a smart watch) which is worn on a person's wrist and/or lower arm; wherein the housing further comprises a sliding extension; wherein the device has a first configuration in which at least three-quarters of the sliding extension is inside the rest of the housing; wherein the device has a second configuration in which at least three-quarters of the sliding extension extends laterally outward from the rest of the housing; a first quadrilateral display with rounded corners on the housing; and a second quadrilateral display with rounded corners on the sliding extension. In another example, a wrist-worn computing device (such as a smart watch) with a multi-configuration display can comprise: a band with a stretchable and/or expandable mesh (or fabric), wherein the band is worn around a person's wrist and/or lower arm; a plurality of displays which are attached to the band; wherein the device has a first configuration in which displays in the plurality of displays collectively span a first lateral width and the band has a second lateral width; wherein the device has a second configuration in which displays in the plurality of displays collectively span a third lateral width and the band has a fourth lateral width; wherein the third lateral width is at least 50% greater than the first lateral width and the fourth lateral width is at least 50% greater than the second lateral width; and where the device is changed from its first configuration to its second configuration by sliding one or more displays in a distal direction (e.g. closer to the person's elbow) and expanding the width of the band in the distal direction.

In an example, a wrist-worn computing device with a multi-configuration display can comprise: a stretchable band which is worn around a person's wrist and/or lower arm; a plurality of displays which are attached to the stretchable band; wherein the device has a first configuration in which displays in the plurality of displays collectively span a first lateral width and the stretchable band has a second lateral width; wherein the device has a second configuration in which displays in the plurality of displays collectively span a third lateral width and the stretchable band has a fourth lateral width, wherein the third lateral width is at least 50% greater than the first lateral width and the fourth lateral width is at least 50% greater than the second lateral width. Alternatively, a wrist-worn computing device with a multi-configuration display can comprise: a variable-width band which is worn around a person's wrist and/or lower arm; a plurality of displays which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by unfolding one or more displays in a proximal direction relative to the other displays and by expanding and/or stretching the band in a proximal direction.

For example, a wrist-worn computing device with a multi-configuration display can comprise: a variable-width band which is worn around a person's wrist and/or lower arm; a plurality of displays which are attached to the variable-width band; wherein the device has a first configuration in which displays in the plurality of displays collectively span a first lateral width and the variable-width band has a second lateral width; wherein the device has a second configuration in which displays in the plurality of displays collectively span a third lateral width and the variable-width band has a fourth lateral width, wherein the third lateral width is at least 50% greater than the first lateral width and the fourth lateral width is at least 50% greater than the second lateral width. In another example, a wrist-worn computing device (such as a smart watch) with a multi-configuration display can comprise: a foldable band which is worn around a person's wrist and/or lower arm; a plurality of foldable displays which are attached to the foldable band; wherein the device has a first configuration in which one or more displays in the plurality of foldable displays are folded over each other and the foldable band is folded over itself;

and wherein the device has a second configuration in which one or more displays in the plurality of foldable displays are unfolded and the foldable band is unfolded.

In an example, a wrist-worn computing device with a multi-configuration display can comprise: a band which is worn around a person's wrist and/or lower arm, wherein the band further comprises a proximal ring and a distal ring, wherein one of the rings can be rotated relative to the other ring around the person's wrist and/or lower arm; a first display which is attached to the proximal ring and a second display which is attached to the distal ring; wherein the device has a first configuration in which the first and second displays are on opposite sides of the person's wrist and/or lower arm; wherein the device has a second configuration in which the first and second displays are (aligned) on the same side of the person's wrist and/or lower arm; and wherein the device is changed from its first configuration to its second configuration by rotating one of the rings relative to the other ring. Alternatively, a wrist-worn computing device with a multi-configuration display can comprise: a housing which is worn on a person's wrist and/or lower arm; wherein the housing further comprises a base portion and a movable portion, wherein one edge of the moveable portion is moveably attached to the base portion by a hinge, joint, strap, band, cord, or membrane; wherein the device has a first configuration in which the movable portion is folded over the base portion; wherein the device has a second configuration in which the movable portion is unfolded from the base portion; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In another embodiment, a wrist-worn computing device with a multi-configuration display can comprise: a housing which is worn on the dorsal surface of a person's wrist and/or lower arm; wherein the housing further comprises a base portion and a movable portion, wherein the moveable portion is moveably attached to the base portion; wherein the device has a first configuration in which the movable portion is folded over the base portion; wherein the device has a second configuration in which the movable portion is unfolded from the base portion; wherein the movable portion has a first side which faces diametrically away from the wrist and/or lower arm in the first configuration and faces (substantially) toward the wrist and/or lower arm in the second configuration; wherein the movable portion has a second side which faces (substantially) toward the wrist and/or lower arm in the first configuration and faces diametrically away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is worn on the dorsal surface of a person's wrist and/or lower arm; wherein the housing further comprises a base portion and a movable portion, wherein the moveable portion is moveably attached to the base portion; wherein the device has a first configuration in which the movable portion is folded over the base portion; wherein the device has a second configuration in which the movable portion is unfolded from the base portion; wherein the movable portion has a first side which faces diametrically away from the wrist and/or lower arm in the first configuration and faces (substantially) toward the wrist and/or lower arm in the second configuration; wherein the movable portion has a second side which faces (substantially) toward the wrist and/or lower arm in the first configuration and faces diametrically away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device (such as a smart watch) with a multi-configuration display can comprise: a housing on a person's wrist and/or lower arm; wherein the housing further comprises a base portion and a movable portion which is attached to the base portion; wherein the device has a first configuration in which the movable portion is folded over the base portion and a second configuration in which the movable portion is unfolded away from the base portion; wherein the movable portion has a first side and a second side which is opposite the first side; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing (such as a smart watch) which is worn on a person's wrist and/or lower arm; wherein the housing further comprises a base portion and a sliding extension; wherein the device has a first configuration in which the sliding extension is on top of the base portion; wherein the device has a second configuration in which the sliding extension is laterally adjacent to the base portion in a proximal, distal, right-lateral, or left-lateral direction; a first display on the housing; and a second display on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is inside the rest of the housing; wherein the device has a second configuration in which the sliding extension extends laterally outward from the rest of the housing; a first quadrilateral display with rounded corners on the housing; and a second quadrilateral display with rounded corners on the sliding extension. In another example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially inside the rest of the housing; wherein the device has a second configuration in which the sliding extension extends in a parallel manner outward from the rest of the housing; a first display on the housing; and a second display on the sliding extension.

For example, a wrist-worn computing device (such as a smart watch) with a multi-configuration display can comprise: a housing (such as a smart watch) which is worn on a person's wrist and/or lower arm; wherein the housing further comprises a sliding extension; wherein the device has a first configuration in which the sliding extension is substantially inside the rest of the housing; wherein the device has a second configuration in which the sliding extension is extended outward, remaining in substantially the same plane, from the rest of the housing; a first display on the housing; and a second display on the sliding extension. Alternatively, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is inside the housing; wherein the device has a second configuration in which the sliding extension is proximally, distally, or laterally extended outward from the housing; a first display on the housing; and a second display on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially on top of (or inside) the housing; wherein the device has a second configuration in which the sliding extension extends outward from the rest of the housing, wherein the virtual plane which best fits the sliding extension remains substantially parallel to the virtual plane which best fits the housing as the sliding extension is moved from the first configuration and in the second configuration; a first display on the housing; and a second display on the sliding extension. In another example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially on top of (or inside) the housing; wherein the device has a second configuration in which the sliding extension extends outward from the rest of the housing, wherein the sliding extension is moved from the first configuration to the second configuration by a spring or other mechanically-tensile member; a first display on the housing; and a second display on the sliding extension.

For example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially within the perimeter of the rest of the housing; wherein the device has a second configuration wherein the sliding extension extends outward between ½" and 3" from the perimeter of the rest of the housing; a first display on the housing; and a second display on the sliding extension. Alternatively, a wrist-worn computing device (such as a smart watch) with a multi-configuration display can comprise: a housing which is worn on a person's wrist and/or lower arm; wherein the housing further comprises a base portion and a movable portion; wherein the distal edge of the moveable portion is movably attached to the base portion (by a hinge, joint, strap, band, cord, or membrane), wherein distal means father from a person's elbow; wherein the device has a first configuration in which the movable portion is folded over the base portion; wherein the device has a second configuration in which the movable portion is unfolded from the base portion; wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion.

In another embodiment, a wrist-worn computing device with a multi-configuration display can comprise: a band which is worn on a person's wrist and/or lower arm; a flexible/bendable display which is attached to the band; wherein the flexible/bendable display has a first configuration in which the flexible/bendable display at least partially spans a lateral (e.g. right or left) portion of the circumference of the band; wherein the flexible/bendable display has a second configuration in which the flexible/bendable display extends outward from the band in a lateral (e.g. right or left) direction in a plane which is substantially tangential to the circumference of the band; wherein the flexible/bendable display is moved from its first configuration to its second configuration by pivoting, tilting, and/or straightening a ventral portion of the flexible/bendable display away from the band; wherein the flexible/bendable display has a third configuration in which the flexible/bendable display extends outward from the band in a distal or proximal direction in a plane which is substantially tangential to the circumference of the band; and wherein the flexible/bendable display is moved from its second configuration to its third configuration by being rotated (approximately 90 degrees) around a rotating joint on the band. In another example, a wrist-worn computing device with a multi-configuration display can comprise: a band which is worn on a person's wrist and/or lower arm; a housing attached to the band; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a band which is worn around a person's wrist and/or lower arm; a housing on the dorsal side of the wrist and/or arm which is attached to the band; wherein the housing further comprises a base portion and a movable portion, wherein the moveable portion is moveably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. Alternatively, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first (single-display) configuration in which the movable portion is folded over the base portion; wherein the device has a second (multi-display) configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which at least part of the movable portion is folded over at least part of the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In another embodiment, a wrist-worn computing device with a multi-configuration display can comprise: a housing which is attached by a band to the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and distal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is worn on the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and distal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration. In another example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded (e.g. pivoted, tilted, flipped, and/or rotated) in an outward and distal direction (away from the person's elbow) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device (such as a smart watch) with a multi-configuration display can comprise: a housing which is attached by a band to the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and proximal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is worn on the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and proximal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device (such as a smart watch) with a multi-configuration display can comprise: a housing which is attached by a band to the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward around the hinge, joint, strap, band, cord, or membrane to a location which is proximal (closer to the person's elbow) relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is attached by a band to a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration (along a radial vector outward from the center of the wrist and/or lower arm) and faces generally toward the wrist and/or lower arm in the second configuration; wherein the movable portion has a second side which faces generally toward the wrist and/or lower arm in the first configuration and faces away from the wrist and/or lower arm in the second configuration (along a radial vector outward from the center of the wrist and/or lower arm); a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a housing which is attached by a band to the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) to a location which is lateral relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In another embodiment, a wrist-worn computing device with a multi-configuration display can comprise: a housing which is attached (by a band) to the surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward in a lateral direction (substantially perpendicular to the longitudinal axis of the person's lower arm) around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded outward from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over (being parallel to and on top of) the base portion; wherein the device has a second configuration in which the movable portion is unfolded from (not being parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. Alternatively, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over the base portion; wherein the device has a second configuration in which the movable portion is unfolded (e.g. pivoted, tilted, flipped, and/or rotated) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded (e.g. pivoted, tilted, flipped, and/or rotated) in an outward and lateral direction (perpendicular to the longitudinal axis of the person's lower arm) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is worn on the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward in a lateral direction (substantially perpendicular to the longitudinal axis of the person's lower arm) around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In another embodiment, a wrist-worn computing device with a multi-configuration display can comprise: a housing which is worn on the dorsal surface of a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded (e.g. pivoted, tilted, flipped, and/or rotated) outward from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a single-display configuration in which the movable portion is folded over the base portion; wherein the device has a multi-display configuration in which the movable portion is unfolded from the base portion; wherein the movable portion has a first side which faces away from the wrist and/or lower arm in the single-display configuration and faces (substantially) toward the wrist and/or lower arm in the second configuration; wherein the movable portion has a second side which faces (substantially) toward the wrist and/or lower arm in the first configuration and faces away from the wrist and/or lower arm in the multi-display configuration; a first display on the first side of the movable portion which functions as the single display in the single-display configuration; a second display on the second side of the movable portion which functions as one of a plurality of displays in the multi-display configuration; and a third display on the base portion which functions as one of a plurality of displays in the multi-display configuration.

In an example, a wrist-worn computing device (such as a smart watch) with a multi-configuration display can comprise: a band which is worn on a person's wrist and/or lower arm; a housing which is attached by the band to the dorsal side of the wrist and/or lower arm; wherein the housing further comprises a rotating portion (such as a ring or bezel), wherein the rotating portion of the housing rotates in a virtual plane which is substantially parallel to the virtual plane which best fits the rest of the housing and/or is substantially parallel to a virtual plane which is tangential to the circumference of the band; a flexible/bendable display which are attached to the rotating portion of the housing; wherein the flexible/bendable display has a first configuration in which the flexible/bendable display is arcuate and curves around a lateral (e.g. right or left) portion of the circumference of the band; wherein the flexible/bendable display has a second configuration in which the flexible/bendable display is substantially planar and extends outward from the rotating portion in a lateral (e.g. right and/or left) direction; wherein the flexible/bendable display has a second configuration in which the flexible/bendable display is substantially planar and extends outward from the rotating portion in a proximal (closer to the person's elbow) and/or distal (farther from the person's elbow) direction; wherein the flexible/bendable display is moved from its first configuration to its second configuration by pivoting, tilting, and/or straightening a ventral portion of the flexible/bendable display away from the circumference of the band; and wherein the flexible/bendable display is moved from its second configuration to its third configuration by rotating the rotating portion of the housing (by 90 degrees).

For example, a wrist-worn computing device with a multi-configuration display can comprise: a housing which is worn on the dorsal surface of a person's wrist and/or lower arm; wherein the housing further comprises a lower base portion; wherein the housing further comprises a upper movable portion, wherein the distal (e.g. farther from the person's elbow) edge of the upper moveable portion is movably and/or flexibly attached to the lower base portion by a hinge, joint, strap, band, cord, or membrane; wherein the device has a single-display configuration in which the movable portion is folded over the base portion; wherein the device has a multi-display configuration in which the movable portion is unfolded from the base portion by pivoting, tilting, and/or rotating the proximal (e.g. closer to the person's elbow) edge of the movable portion away from the base portion; wherein the movable portion has a first side which faces generally away from the wrist in the single-display configuration and faces generally toward the wrist and/or lower arm in the multi-display configuration; wherein the movable portion has a second side which faces generally toward the wrist and/or lower arm in the single-display configuration and faces generally away from the wrist in the multi-display configuration; a first display on the first side of the movable portion; a second display (or portion of a multi-part display) on the second side of the movable portion; and a third display (or portion of a multi-part display) on the base portion.

In another embodiment, a wrist-worn computing device with a multi-configuration display can comprise: a housing which is worn on a person's wrist and/or lower arm; wherein the housing further comprises a base portion and a movable portion; wherein the left-lateral edge of the moveable portion is movably attached to the base portion (by a hinge, joint, strap, band, cord, or membrane), wherein lateral means perpendicular to the longitudinal axis of a person's lower arm; wherein the device has a first configuration in which the movable portion is folded over the base portion; wherein the device has a second configuration in which the movable portion is unfolded from the base portion; wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is worn on a person's wrist and/or lower arm; wherein the housing further comprises a base portion and a movable portion; wherein the moveable portion is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and distal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device (such as a smart watch) with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and proximal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over the base portion; wherein the device has a second configuration in which an edge of the movable portion is unfolded outward in a lateral direction (substantially perpendicular to the longitudinal axis of the person's lower arm) relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device (such as a smart watch) with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over the base portion; wherein the device has a second configuration in which the movable portion is unfolded relative to the base portion; wherein the movable portion has a first side which faces away from the wrist and/or lower arm in the first configuration and faces generally toward the wrist and/or lower arm in the second configuration; wherein the movable portion has a second side which faces generally toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. Alternatively, a wrist-worn computing device with a multi-configuration display can comprise: a band which is worn on a person's wrist and/or lower arm; one or more displays which are attached to a rotating joint or axle on the band; wherein the one or more displays have a first configuration in which the one or more displays at least partially span a lateral (e.g. right or left) portion of the circumference of the band; wherein the one or more displays have a second configuration in which the one or more displays are substantially planar and extend outward from the band in a lateral (e.g. right or left) direction in a plane which is substantially tangential to the circumference of the band; wherein the one or more displays are moved from their first configuration to their second configuration by pivoting, tilting, and/or straightening a ventral portion of the one or more displays away from the band; wherein the one or more displays have a third configuration in which the one or more displays are substantially planar and extend outward from the band in a distal or proximal direction in a plane which is substantially tangential to the circumference of the band; and wherein the one or more displays are moved from their second configuration to their third configuration by being rotated (approximately 90 degrees) around the rotating joint or axle on the band.

In an example, a wrist-worn computing device with a multi-configuration display can comprise: a band which is worn on a person's wrist and/or lower arm; one or more displays which are attached to the dorsal side of the band and/or to a housing on the dorsal side of the band; wherein the one or more displays have a first configuration in which the one or more displays curve around a lateral (right or left) portion of the circumference of the band; wherein the one or more displays have a second configuration in which the one or more displays stick out like one or more wings in a lateral (right and/or left) manner from the dorsal side of the band and/or the housing on the dorsal side of the band; wherein the one or more displays have a third configuration in which the one or more displays stick out in a proximal (closer to the person's elbow) and/or distal (farther from the person's elbow) manner from the dorsal side of the band and/or the housing on the dorsal side of the band; wherein the one or more displays are changed from their first configuration to their second configuration by moving (e.g. pivoting, bending, unfolding, or lifting) an end of the one or more displays away from the circumference of the band; wherein the one or more displays are changed from their second configuration to their third configuration by rotating (the end of) the one or more displays around the dorsal side of the band and/or around the housing on the dorsal side of the band. In another example, a wrist-worn computing device with a multi-configuration display can comprise: a housing which is worn on a person's wrist and/or lower arm; wherein the housing further comprises a base portion and a movable portion; wherein the proximal edge of the moveable portion is movably attached to the base portion (by a hinge, joint, strap, band, cord, or membrane), wherein proximal means closer to a person's elbow; wherein the device has a first configuration in which the movable portion is folded over the base portion; wherein the device has a second configuration in which the movable portion is unfolded from the base portion; wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a band which is worn on a person's wrist and/or lower arm; a segmented display which is attached to the band by a rotating joint or axle; wherein the segmented display has a first configuration in which it at least partially curves around a lateral (e.g. right or left) portion of the circumference of the band; wherein the segmented display has a second configuration in which it extends outward from the band in a lateral (e.g. right and/or left) direction in a plane which is substantially tangential to the circumference of the band; wherein the segmented display is moved from its first configuration to its second configuration by pivoting, tilting, and/or straightening an end of the segmented display away from the band; wherein the segmented display has a third configuration in which the segmented display extends outward from the band in a distal and/or proximal direction in a plane which is substantially tangential to the circumference of the band; and wherein the segmented display is moved from its second configuration to its third configuration by being rotated (approximately 90 degrees) around the rotating joint or axle.

In another embodiment, a wrist-worn computing device (such as a smart watch) with a multi-configuration display can comprise: a band which is worn on a person's wrist and/or lower arm; a housing which is attached by the band to the dorsal side of the wrist and/or lower arm; a chain of displays which is attached to the housing and/or the band; wherein the chain of displays has a first configuration in which the chain of displays is arcuate and at least partially curves around a lateral (e.g. right or left) portion of the circumference of the band; wherein the chain of displays has a second configuration in which the chain of displays is substantially planar and extends straight outward from the band and/or the housing in a lateral (e.g. right or left) direction in a plane which is substantially coplanar with the housing and/or substantially tangential to the circumference of the band; wherein the chain of displays is moved from its first configuration to its second configuration by pivoting, tilting, and/or straightening a ventral portion of the chain of displays away from the band; wherein the chain of displays has a third configuration in which the chain of displays is substantially planar and extends straight outward from the band and/or the housing in a distal or proximal direction in a plane which is substantially coplanar with the housing and/or substantially tangential to the circumference of the band; and wherein the chain of displays is moved from its second configuration to its third configuration by being rotated (approximately 90 degrees) around the housing and/or around a rotating joint on the band.

For example, a wrist-worn computing device with a multi-configuration display can comprise: a band which is worn on a person's wrist and/or lower arm; a housing which is attached by the band to the dorsal side of the wrist and/or lower arm; a connected array of displays; wherein the connected array of displays has a first configuration in which the connected array of displays at least partially spans a lateral (e.g. right or left) side of the band; wherein the connected array of displays has a second configuration in which the connected array of displays extends straight outward from the band and/or the housing in a lateral (e.g.

right or left) direction in a plane which is substantially coplanar with the housing and/or substantially tangential to the circumference of the band; wherein the connected array of displays is moved from its first configuration to its second configuration by pivoting, tilting, and/or straightening a ventral portion of the connected array of displays away from the band; wherein the connected array of displays has a third configuration in which the connected array of displays extends straight outward from the band and/or the housing in a distal or proximal direction in a plane which is substantially coplanar with the housing and/or substantially tangential to the circumference of the band; and wherein the connected array of displays is moved from its second configuration to its third configuration by being rotated (approximately 90 degrees) around the housing and/or around a rotating joint on the band.

In an example, a wrist-worn computing device (such as a smart watch) with a multi-configuration display can comprise: a band which is worn on a person's wrist and/or lower arm; a housing which is attached by the band to the dorsal side of the wrist and/or lower arm; a connected series of displays; wherein the connected series of displays has a first configuration in which the connected series of displays is arcuate and at least partially curves around a lateral (e.g. right or left) portion of the circumference of the band; wherein the connected series of displays has a second configuration in which the connected series of displays is substantially planar and extends straight outward from the band and/or the housing in a lateral (e.g. right or left) direction in a plane which is substantially coplanar with the housing and/or substantially tangential to the circumference of the band; wherein the connected series of displays is moved from its first configuration to its second configuration by pivoting, tilting, and/or straightening out a ventral portion of the connected series of displays away from the band; wherein the connected series of displays has a third configuration in which the connected series of displays is substantially planar and extends straight outward from the band and/or the housing in a distal or proximal direction in a plane which is substantially coplanar with the housing and/or substantially tangential to the circumference of the band; and wherein the connected series of displays is moved from its second configuration to its third configuration by being rotated (approximately 90 degrees) around the housing and/or around a rotating joint on the band.

In an example, a wrist-worn computing device with a multi-configuration display can comprise: a band which is worn on a person's wrist and/or lower arm; a housing which is attached by the band to the dorsal side of the wrist and/or lower arm; a display which is attached to the housing and/or the band; wherein the display has a first configuration in which the display is arcuate and at least partially curves around a lateral (e.g. right or left) portion of the circumference of the band; wherein the display has a second configuration in which the display is substantially flat and extends outward from the band and/or the housing in a lateral (e.g. right or left) direction in a plane which is substantially coplanar with the housing and/or substantially tangential to the circumference of the band; wherein the display is moved from its first configuration to its second configuration by pivoting, tilting, and/or straightening out a ventral portion of the display away from the band; wherein the display has a third configuration in which the display is substantially flat and extends outward from the band and/or the housing in a distal or proximal direction in a plane which is substantially coplanar with the housing and/or substantially tangential to the circumference of the band; and wherein the display is moved from its second configuration to its third configuration by being rotated (approximately 90 degrees) around the housing and/or around a rotating joint on the band. In another example, a wrist-worn computing device with a multi-configuration display can comprise: a band which is worn on a person's wrist and/or lower arm; a housing which is attached by the band to the dorsal side of the wrist and/or lower arm; a display which is on one lateral side (e.g. right or left) of the housing; wherein the display has a first configuration in which the display at spans at least a portion of the lateral side of the band; wherein the display has a second configuration in which the display extends outward from the band and/or the housing in a lateral (e.g. right or left) direction in a plane which is substantially coplanar with the housing and/or substantially tangential to the circumference of the band; wherein the display is moved from its first configuration to its second configuration by detaching a ventral portion of the display from the band and pivoting, tilting, and/or straightening the ventral portion away from the band; wherein the display has a third configuration in which the display extends outward from the band and/or the housing in a distal or proximal direction in a plane which is substantially coplanar with the housing and/or substantially tangential to the circumference of the band; and wherein the display is moved from its second configuration to its third configuration by being rotated (approximately 90 degrees) around the housing and/or around a rotating joint on the band.

In an example, a wrist-worn computing device with a multi-configuration display can comprise: a band which is worn on a person's wrist and/or lower arm; a housing which is attached by the band to the dorsal side of the person's wrist and/or arm; a first display; and a second display; wherein the device has a first configuration in which the first display is on top of the housing, the second display is on the housing under the first display, and the dorsal side of the band has a first width; wherein the device has a second configuration in which the first display extends out from the housing in a distal (farther from the person's elbow) direction, the second display is on the housing, and the dorsal side of the band has a second width, wherein the second width is greater than the first width; and wherein the first display slides out from the housing in a proximal direction and the width of the dorsal side of the band expands as the device changes from the first configuration to the second configuration. Alternatively, a wrist-worn computing device with a multi-configuration display can comprise: a distal band which is worn around a person's wrist and/or lower arm; a proximal band which is worn around the person's wrist and/or lower arm, wherein the proximal band is closer to the person's elbow than the distal band, and wherein the proximal band can be rotated relative to the distal band (around the person's wrist and/or lower arm); a first display which is attached to the distal band; a second display which is attached to the proximal band; wherein the device has a first configuration in which the first display is on a first (e.g. dorsal) side of the person's wrist and/or lower arm and the second display is on a second (e.g. ventral) side of the person's wrist and/or arm, wherein the second side is opposite the first side; wherein the device has a second configuration in which the first display is on the first (e.g. dorsal) side of the person's wrist and/or lower arm and the second display is also on the first (e.g. dorsal) side of the person's wrist and/or arm; and wherein the device is changed from its first configuration to its second configuration by rotating the proximal band (180 degrees) relative to the distal band.

For example, a wrist-worn computing device (such as a smart watch) with a multi-configuration display can comprise: a distal band which is worn around a person's wrist and/or lower arm; a proximal band which is worn around the person's wrist and/or lower arm, wherein the proximal band is closer to the person's elbow than the distal band, and wherein the proximal band can be rotated relative to the distal band (around the person's wrist and/or lower arm); a first display which is attached to the distal band; a second display which is attached to the proximal band; wherein the device has a first configuration in which the first display is on a first (e.g. dorsal) side of the person's wrist and/or lower arm and the second display is on a second (e.g. ventral) side of the person's wrist and/or arm, wherein the second side is opposite the first side; wherein the device has a second configuration in which the first display and the second display align to form a combined larger display on the first (e.g. dorsal) side of the person's wrist and/or arm; and wherein the device is changed from its first configuration to its second configuration by rotating the proximal band relative to the distal band. In another example, a wrist-worn computing device with a multi-configuration display can comprise: a band which is worn on a person's wrist and/or lower arm; a housing which is attached by the band to the dorsal side of the wrist and/or lower arm; a flexible/bendable display which is attached the housing and/or the band; wherein the flexible/bendable display has a first configuration in which the flexible/bendable display is arcuate and curves around a lateral (e.g. right or left) portion of the circumference of the band; wherein the flexible/bendable display has a second configuration in which the flexible/bendable display extends outward from the band and/or the housing in a lateral (e.g. right or left) direction in a plane which is substantially coplanar with the housing and/or substantially tangential to the circumference of the band; wherein the flexible/bendable display is moved from its first configuration to its second configuration by detaching a ventral portion of the flexible/bendable display from the band and pivoting, tilting, and/or straightening out the ventral portion away from the band; wherein the flexible/bendable display has a third configuration in which the flexible/bendable display extends outward from the band and/or the housing in a distal or proximal direction in a plane which is substantially coplanar with the housing and/or substantially tangential to the circumference of the band; and wherein the flexible/bendable display is moved from its second configuration to its third configuration by being rotated (approximately 90 degrees) around the housing and/or around a rotating joint on the band.

In another embodiment, a wrist-worn computing device with a multi-configuration flexible/bendable display can comprise: a band which is worn on a person's wrist and/or lower arm; a housing which is attached by the band to the dorsal side of the wrist and/or lower arm; a flexible/bendable display which is attached to the housing and/or the band; wherein the flexible/bendable display has a first configuration in which the flexible/bendable display is arcuate and at least partially curves around a lateral (e.g. right or left) portion of the circumference of the band; wherein the flexible/bendable display has a second configuration in which the flexible/bendable display extends outward from the band and/or the housing in a lateral (e.g. right or left) direction in a plane which is substantially coplanar with the housing and/or substantially tangential to the circumference of the band; wherein the flexible/bendable display is moved from its first configuration to its second configuration by pivoting, tilting, and/or straightening out a ventral portion of the flexible/bendable display away from the band; wherein the flexible/bendable display has a third configuration in which the flexible/bendable display extends outward from the band and/or the housing in a distal or proximal direction in a plane which is substantially coplanar with the housing and/or substantially tangential to the circumference of the band; and wherein the flexible/bendable display is moved from its second configuration to its third configuration by being rotated (approximately 90 degrees) around the housing and/or around a rotating joint on the band.

For example, a wrist-worn computing device with a multi-configuration display can comprise: a band which is worn on a person's wrist and/or lower arm; a right display which is attached by a first rotational joint to the right-dorsal quadrant of the band circumference; a left display which is attached by a second rotational joint to the left-dorsal quadrant of the band circumference; wherein the device has a first configuration in which the right and left displays are arcuate and curve around the circumference of the band; wherein the device has a second configuration in which the right and left displays are substantially planar and extend out from the band in lateral (right and left) directions, respectively; wherein the device has a third configuration in which the right and left displays are substantially planar and extend out from the band in proximal and distal directions, respectively; wherein the right and left displays are changed from the first configuration to the second configuration by pivoting, bending, or straightening their ventral portions away from the circumference of the band; wherein the right and left displays are changed from the second configuration to the third configuration by rotating them, clockwise and counterclockwise, respectively, around the first and second rotational joints, respectively.

In an example, a wrist-worn computing device with a multi-configuration display can comprise: a band which is worn on a person's wrist and/or lower arm; a rotating housing which is attached by the band to the dorsal side of the person's wrist and/or lower arm; a right display which is attached to the right side of the housing; a left display which is attached to the left side of the housing; wherein the device has a first configuration in which the right and left displays lie along the circumference of the band; wherein the device has a second configuration in which the right and left displays extend out from the band in lateral (right and left) directions, respectively; wherein the device has a third configuration in which the right and left displays both extend out from the band in a proximal direction; wherein the right and left displays are changed from the first configuration to the second configuration by pivoting, bending, or straightening their ventral portions away from the circumference of the band; wherein the right and left displays are changed from the second configuration to the third configuration by rotating the housing (90 degrees). In another example, a wrist-worn computing device (such as a smart watch) with a multi-configuration display can comprise: a band which is worn on a person's wrist and/or lower arm; a housing which is attached by the band to the dorsal side of the person's wrist and/or lower arm; a rotating ring or bezel around the housing; a right display which is attached to the right side of the ring or bezel; a left display which is attached to the left side of the ring or bezel; wherein the device has a first configuration in which the right and left displays lie along the circumference of the band; wherein the device has a second configuration in which the right and left displays extend out from the band in lateral (right and left) directions, respectively; wherein the device has a third configuration in which the right and left displays extend out from the band in proximal and distal directions, respectively; wherein the right and left displays are changed from the first configuration to the second configuration by pivoting, bending, or straightening their ventral portions away from the circumference of the band; wherein the right and left displays are changed from the second configuration to the third configuration by rotating the ring or bezel (by 90 degrees).

For example, a wrist-worn computing device with a multi-configuration display can comprise: a band which is worn on a person's wrist and/or lower arm; a housing which is attached to the dorsal side of band; a rotating ring or bezel around the housing; one or more displays which are attached to the rotating ring or bezel; wherein the one or more displays have a first configuration in which the one or more displays curve around a lateral (e.g. right or left) portion of the circumference of the band; wherein the one or more displays have a second configuration in which the one or more displays extend outward from the ring or bezel in a lateral (e.g. right and/or left) direction; wherein the one or more displays have a third configuration in which the one or more displays extend outward from the ring or bezel in a proximal (e.g. farther from the person's elbow) and/or distal (closer to the person's elbow) direction; wherein the one or more displays are moved from their first configuration to their second configuration by pivoting, tilting, and/or straightening a ventral portion of the one or more displays away from the band; and wherein the one or more displays are moved from their second configuration to their third configuration by rotating the ring or bezel (by 90 degrees) around the housing. Alternatively, a wrist-worn computing device (such as a smart watch) with a multi-configuration display can comprise: a band which is worn around a person's wrist and/or lower arm, wherein the band further comprises a proximal ring with a circumferentially-variable width and a distal ring with a circumferentially-variable width, wherein one of the rings can be rotated relative to the other ring around the person's wrist and/or lower arm; a first display which is attached to the proximal ring; and a second display which is attached to the distal ring on a wide portion of the distal ring, wherein the distal perimeter of the second display extends out from the distal ring in a distal manner; wherein the device has a first configuration in which the first and second displays are on opposite sides of the person's wrist and/or lower arm; wherein the device has a second configuration in which the first and second displays are aligned on the same side of the person's wrist and/or lower arm to form a (large) combined display; and wherein the device is changed from its first configuration to its second configuration by rotating one of the rings relative to the other ring.

In an example, a wrist-worn computing device with a multi-configuration display can comprise: a band which is worn on a person's wrist and/or lower arm; a housing which is attached by the band to the dorsal side of the wrist and/or lower arm; flexible/bendable display which is attached to the housing and/or the band; wherein the flexible/bendable display has a first configuration in which the flexible/bendable display at least partially spans a lateral (e.g. right or left) portion of the band; wherein the flexible/bendable display has a second configuration in which the flexible/bendable display extends outward from the band and/or the housing in a lateral (e.g. right or left) direction in a plane which is substantially coplanar with the housing and/or substantially tangential to the circumference of the band; wherein the flexible/bendable display is moved from its first configuration to its second configuration by pivoting, tilting, and/or straightening a ventral portion of the flexible/bendable display away from the band; wherein the flexible/bendable display has a third configuration in which the flexible/bendable display extends outward from the band and/or the housing in a distal or proximal direction in a plane which is substantially coplanar with the housing and/or substantially tangential to the circumference of the band; and wherein the flexible/bendable display is moved from its second configuration to its third configuration by being rotated around ring or bezel around the housing.

In an example, a wrist-worn computing device with a multi-configuration display can comprise: a band which is worn on a person's wrist and/or lower arm; a housing which is attached by the band to the dorsal side of the wrist and/or lower arm; one or more displays which are attached to the housing and/or the band; wherein the one or more displays have a first configuration in which the one or more displays at least partially span a lateral (e.g. right or left) portion of the band; wherein the one or more displays have a second configuration in which the one or more displays extend outward from the band and/or the housing in a lateral (e.g. right or left) direction in a plane which is substantially coplanar with the housing and/or substantially tangential to the circumference of the band; wherein the one or more displays are moved from their first configuration to their second configuration by pivoting, tilting, and/or straightening a ventral portion of the one or more displays away from the band; wherein the one or more displays have a third configuration in which the one or more displays extend outward from the band and/or the housing in a distal or proximal direction in a plane which is substantially coplanar with the housing and/or substantially tangential to the circumference of the band; and wherein the one or more displays are moved from their second configuration to their third configuration by being rotated around the housing.

In another embodiment, a wrist-worn computing device with a multi-configuration display can comprise: a housing which is worn on the dorsal surface of a person's wrist and/or lower arm; wherein the housing further comprises a base portion and a movable portion; wherein a first edge of the moveable portion is moveably attached to the base portion; wherein the device has a first configuration in which the movable portion is folded over the base portion; wherein the device has a second configuration in which the movable portion is unfolded from the base portion by moving a second edge of the movable portion away from the base portion, and wherein the second edge is opposite the first edge; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device (such as a smart watch) with a multi-configuration display can comprise: a band which is worn on a person's wrist and/or lower arm; wherein the band further comprises a distal ring; wherein the band further comprises a proximal ring; wherein the band further comprises a stretchable (and/or extendable) mesh between the distal ring and the proximal ring; a housing which is attached to the proximal ring; a first display on the housing; and a second display which is attached to the distal ring, wherein the second display slides into (and out of) the housing.

For example, a wrist-worn computing device with a multi-configuration display can comprise: a band which is worn on a person's wrist and/or lower arm; wherein the band further comprises a first ring around the person's wrist and/or lower arm; wherein the band further comprises a second ring around the person's wrist and/or lower arm; wherein the band further comprises a stretchable mesh (or fabric) between the first ring and the second ring; a housing which is attached to the first ring; a first display on the housing; and a second display which is attached to the second ring; wherein the device has a first configuration in which at least three-quarters of the second display is inside the housing and the stretchable mesh (or fabric) has a first width; wherein the device has a second configuration in which at least three quarters of the second display is outside the housing and the stretchable mesh (or fabric) has a second width, wherein the second width is greater than the first width. Alternatively, a wrist-worn computing device with a multi-configuration display can comprise: a housing (such as a smart watch) which is worn on a person's wrist and/or lower arm; wherein the housing further comprises a sliding extension; wherein the device has a first configuration in which at least 75% of the upper surface of the sliding extension is inside the housing; wherein the device has a second configuration in which at least 75% of the upper surface of the sliding extension is outside the housing; a first display on the housing; and a second display on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which at least 90% of the upper surface of the sliding extension is inside the rest of the housing; wherein the device has a second configuration in which at least 90% of the upper surface of the sliding extension is outside the rest of the housing; a first display on the housing; and a second display on the sliding extension. In another example, a wrist-worn computing device (such as a smart watch) with a multi-configuration display can comprise: a housing (such as a smart watch) which is worn on a person's wrist and/or lower arm; wherein the housing further comprises a base portion and a sliding extension; wherein the device has a first configuration in which at least three-quarters of the sliding extension is on top of the base portion; wherein the device has a second configuration in which at least three-quarters of the sliding extension is extended outward from the base portion in a proximal, distal, right-lateral, or left-lateral direction; a first display on the housing; and a second display on the sliding extension.

For example, a wrist-worn computing device with a multi-configuration display can comprise: a housing (such as a smart watch) which is worn on a person's wrist and/or lower arm; wherein the housing further comprises a sliding extension; wherein the device has a first configuration in which at least three-quarters of the sliding extension is on top of the rest of the housing; wherein the device has a second configuration in which at least three-quarters of the sliding extension extends laterally outward from the rest of the housing; wherein the sliding extension remains in substantially the same virtual plane in both the first configuration and the second configuration as well as in the transition from the first configuration to the second configuration; wherein the sliding extension is moved from the first configuration to the second configuration by an electromagnetic actuator or by a mechanical spring; a first quadrilateral display with rounded corners on the housing; and a second quadrilateral display with rounded corners on the sliding extension. In another example, a wrist-worn computing device with a multi-configuration display can comprise: a housing (such as a smart watch) which is worn on a person's wrist and/or lower arm; wherein the housing further comprises a sliding extension; wherein the device has a first configuration in which at least three-quarters of the sliding extension is inside the rest of the housing; wherein the device has a second configuration in which at least three-quarters of the sliding extension extends laterally outward in a distal, proximal, right-lateral, or left-lateral direction from the rest of the housing; wherein the sliding extension remains in substantially the same virtual plane in both the first configuration and the second configuration as well as in the transition from the first configuration to the second configuration; wherein the sliding extension is moved from the first configuration to the second configuration by an electromagnetic actuator or by a mechanical spring; a first quadrilateral display with rounded corners on the housing; and a second quadrilateral display with rounded corners on the sliding extension.

In another embodiment, a wrist-worn computing device with a multi-configuration display can comprise: a housing (such as a smart watch) which is worn on a person's wrist and/or lower arm; wherein the housing further comprises a sliding extension; wherein the device has a first configuration in which at least three-quarters of the sliding extension is inside the rest of the housing; wherein the device has a second configuration in which at least three-quarters of the sliding extension extends out from the rest of the housing in a proximal, distal, right-lateral, or left-lateral direction; a first display on the housing; and a second display on the sliding extension. In another example, a wrist-worn computing device (such as a smart watch) with a multi-configuration display can comprise: a band with a stretchable and/or expandable mesh (or fabric), wherein the band is worn around a person's wrist and/or lower arm; a plurality of displays which are attached to the band; wherein the device has a first configuration in which displays in the plurality of displays collectively span a first lateral width and the band has a second lateral width; wherein the device has a second configuration in which displays in the plurality of displays collectively span a third lateral width and the band has a fourth lateral width; wherein the third lateral width is at least 50% greater than the first lateral width and the fourth lateral width is at least 50% greater than the second lateral width; and where the device is changed from its first configuration to its second configuration by sliding one or more displays in proximal and/or distal direction(s) and expanding the width of the band in proximal and/or distal direction(s).

For example, a wrist-worn computing device with a multi-configuration display can comprise: a variable-width band which is worn around a person's wrist and/or lower arm; a plurality of displays which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width. Alternatively, a wrist-worn computing device (such as a smart watch) with a multi-configuration display can comprise: a variable-width band which is worn around a person's wrist and/or lower arm; a plurality of displays which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by unfolding one or more displays in a distal direction relative to the other displays and by expanding and/or stretching the band in a distal direction.

In an example, a wrist-worn computing device with a multi-configuration display can comprise: a variable-width band which is worn around a person's wrist and/or lower arm; a telescoping series of displays which are attached to the variable-width band; wherein the device has a first configuration in which displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by un-telescoping (e.g. sliding out) one or more displays in a proximal direction and by expanding and/or stretching the band in a proximal direction. In another example, a wrist-worn computing device with a multi-configuration display can comprise: a band with an elastic mesh which is worn around a person's wrist and/or lower arm; a plurality of folded displays which are attached to the band; wherein the device has a first configuration in which one or more displays in the plurality of displays are folded over each other and the band has a first width; and wherein the device has a second configuration in which one or more displays in the plurality of displays are unfolded and the band has a second width, wherein the second width is greater than the first width.

In an example, a wrist-worn computing device with a multi-configuration display can comprise: a band which is worn around a person's wrist and/or lower arm, wherein the band further comprises a proximal ring and a distal ring, wherein one of the rings can be rotated relative to the other ring around the person's wrist and/or lower arm; a first display which is attached to the proximal ring and a second display which is attached to the distal ring; wherein the device has a first configuration in which the first and second displays are on opposite sides of the person's wrist and/or lower arm; wherein the device has a second configuration in which the first and second displays are aligned on the same side of the person's wrist and/or lower arm to form a (large) combined display; and wherein the device is changed from its first configuration to its second configuration by rotating one of the rings relative to the other ring. Alternatively, a wrist-worn computing device with a multi-configuration display can comprise: a housing which is worn on the dorsal surface of a person's wrist and/or lower arm; wherein the housing further comprises a base portion and a movable portion, wherein one edge of the moveable portion is moveably attached to the base portion by a hinge, joint, strap, band, cord, or membrane; wherein the device has a first configuration in which the movable portion is folded over the base portion; wherein the device has a second configuration in which the movable portion is unfolded from the base portion; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device (such as a smart watch) with a multi-configuration display can comprise: a housing which is worn on the dorsal surface of a person's wrist and/or lower arm; wherein the housing further comprises a base portion and a movable portion, wherein one edge of the moveable portion is moveably attached to the base portion by a hinge, joint, strap, band, cord, or membrane; wherein the device has a first configuration in which the movable portion is folded over the base portion; wherein the device has a second configuration in which the movable portion is unfolded from the base portion; wherein the movable portion has a first side which faces radially away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a smart watch which is worn on person's wrist and/or arm; wherein the smart watch further comprises a base portion and a movable portion, wherein the moveable portion is moveably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device (such as a smart watch) with a multi-configuration display can comprise: a housing (such as a smart watch) which is worn on a person's wrist and/or lower arm; wherein the housing further comprises a base portion and a sliding extension; wherein the device has a first configuration in which the sliding extension is on top of the base portion; wherein the device has a second configuration in which the sliding extension is extended outward from the base portion in a proximal, distal, right-lateral, or left-lateral direction; a first display on the housing; and a second display on the sliding extension. Alternatively, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is on top of the rest of the housing; wherein the device has a second configuration in which the sliding extension extends laterally outward from the rest of the housing; a first quadrilateral display with rounded corners on the housing; and a second quadrilateral display with rounded corners on the sliding extension.

In another embodiment, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is inside the rest of the housing; wherein the device has a second configuration in which the sliding extension extends out from the rest of the housing; a first quadrilateral display with rounded corners on the housing; and a second quadrilateral display with rounded corners on the sliding extension. In another example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially inside the rest of the housing; wherein the device has a second configuration in which the sliding extension is extended outward, remaining in substantially the same plane, from the rest of the housing; a first display on the housing; and a second display on the sliding extension.

For example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is inside the rest of the housing; wherein the device has a second configuration in which the sliding extension extends out from the rest of the housing in a proximal, distal, right-lateral, or left-lateral direction; a first display on the housing; and a second display on the sliding extension. In another example, a wrist-worn computing device (such as a smart watch) with a multi-configuration display can comprise: a housing (such as a smart watch) which is worn on a person's wrist and/or lower arm; wherein the housing further comprises a sliding extension; wherein the device has a first configuration in which the sliding extension is substantially inside the housing; wherein the device has a second configuration in which the sliding extension is substantially outside the housing; a first display on the housing; and a second display on the sliding extension. In another example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially on top of (or inside) the housing; wherein the device has a second configuration in which the sliding extension extends outward from the rest of the housing, wherein the sliding extension is in substantially the same virtual plane in both the first and second configurations; a first display on the housing; and a second display on the sliding extension. Alternatively, a wrist-worn computing device (such as a smart watch) with a multi-configuration display can comprise: a housing (such as a smart watch) which is worn on a person's wrist and/or lower arm; wherein the housing further comprises a sliding extension; wherein the device has a first configuration in which the sliding extension is substantially on top of (or inside) the housing; wherein the device has a second configuration in which the sliding extension extends outward from the rest of the housing, wherein the centroid of the sliding extension is moved in a proximal direction (e.g. closer to the person's elbow) as the sliding extension is moved from the first configuration to the second configuration; a first display on the housing; and a second display on the sliding extension.

In an example, a wrist-worn computing device with a multi-configuration display can comprise: a housing (such as a smart watch) which is worn on a person's wrist and/or lower arm; wherein the housing further comprises a sliding extension; wherein the device has a first configuration in which the sliding extension is substantially within the perimeter of the rest of the housing; wherein the device has a second configuration wherein the sliding extension extends outward between 2" and 5" from the perimeter of the rest of the housing; a first display on the housing; and a second display on the sliding extension. In another example, a wrist-worn computing device with a multi-configuration display can comprise: a housing which is worn on a person's wrist and/or lower arm; wherein the housing further comprises a base portion which is a first distance from the surface of the person's wrist and/or lower arm and a movable portion which is a second distance from the surface of the person's wrist and/or lower arm, wherein the second distance is greater than the first distance; wherein the distal edge of the moveable portion is movably attached to the base portion by a hinge, joint, strap, band, cord, or membrane, wherein distal means father from a person's elbow; wherein the device has a first configuration in which the movable portion is folded over the base portion (being substantially parallel to and above the base portion); wherein the device has a second configuration in which the movable portion is unfolded from the base portion (being substantially coplanar with and adjacent to the base portion); wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a band which is worn on a person's wrist and/or lower arm; a flexible/bendable display which is attached to the dorsal side of the band and/or to a housing on the dorsal side of the band; wherein the flexible/bendable display has a first configuration in which the flexible/bendable display curves around a lateral (right or left) portion of the circumference of the band; wherein the flexible/bendable display has a second configuration in which the flexible/bendable display sticks out in a lateral (right and/or left) manner from the dorsal side of the band and/or the housing on the dorsal side of the band; wherein the flexible/bendable display has a third configuration in which the flexible/bendable display sticks out in a proximal (closer to the person's elbow) and/or distal (farther from the person's elbow) manner from the dorsal side of the band and/or the housing on the dorsal side of the band; wherein the flexible/bendable display is changed from its first configuration to its second configuration by moving (e.g. pivoting, bending, unfolding, or lifting) an end of the flexible/bendable display away from the circumference of the band; wherein the flexible/bendable display is changed from its second configuration to its third configuration by rotating (the end of) the flexible/bendable display around the dorsal side of the band and/or around the housing on the dorsal side of the band. Alternatively, a wrist-worn computing device with a multi-configuration display can comprise: a band which is worn on a person's wrist and/or lower arm; a housing which is attached to the band; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In another embodiment, a wrist-worn computing device (such as a smart watch) with a multi-configuration display can comprise: a band which is worn on a person's wrist and/or lower arm; a housing which is attached to the band; wherein the housing further comprises a base portion and a movable portion, wherein the moveable portion is moveably attached to the base portion by a hinge, joint, strap, band, cord, or membrane; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first (single-display) configuration in which the movable portion is folded over the base portion; wherein the device has a second (multi-display) configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which at least part of the movable portion is folded over at least part of the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device with a multi-configuration display can comprise: a housing which is attached (by a band) to the surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and distal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded in a distal direction (away from the person's elbow) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is attached by a band to the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward around the hinge, joint, strap, band, cord, or membrane to a location which is distal (farther from the person's elbow) relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device (such as a smart watch) with a multi-configuration display can comprise: a housing which is attached (by a band) to the surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and proximal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In another embodiment, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded in an outward and proximal direction (toward the person's elbow) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device (such as a smart watch) with a multi-configuration display can comprise: a housing which is attached by a band to the dorsal surface of a person's wrist and/or lower arm; wherein the housing further comprises a base portion; wherein the housing further comprises a movable portion which is movably attached to the base portion; wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) to a location which is proximal (closer to the person's elbow) relative to the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In an example, a wrist-worn computing device with a multi-configuration display can comprise: a housing which is attached by a band to a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which the movable portion is unfolded (e.g. pivoted, tilted, flipped, and/or rotated) outward around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

In another embodiment, a wrist-worn computing device (such as a smart watch) with a multi-configuration display can comprise: a housing which is attached by a band to the dorsal surface of a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is attached (by a band) to the surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward in a lateral direction (substantially perpendicular to the longitudinal axis of the person's lower arm) around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over (being parallel to and on top of) the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. Alternatively, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded (e.g. pivoted, tilted, flipped, and/or rotated) outward from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

In an example, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and seen in the first configuration and faces (substantially) toward the wrist and/or lower arm in the second configuration; wherein the movable portion has a second side which faces (substantially) toward the wrist and/or lower arm in the first configuration and faces away from the wrist and seen in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded in an outward and lateral direction (perpendicular to the longitudinal axis of the person's lower arm) from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion.

For example, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over (being parallel to and on top of) the base portion; wherein the device has a second configuration in which the movable portion is unfolded from (no longer parallel to and on top of) the base portion; wherein the movable portion has a first side which faces away from the wrist and seen in the first configuration and faces (substantially) toward the wrist and/or lower arm in the second configuration; wherein the movable portion has a second side which faces (substantially) toward the wrist and/or lower arm in the first configuration and faces away from the wrist and seen in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on the dorsal surface of a person's wrist and/or lower arm; wherein the housing further comprises a base portion; wherein the housing further comprises a movable portion which is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward in a lateral direction (substantially perpendicular to the longitudinal axis of the person's lower arm) around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device (such as a smart watch) with a multi-configuration display can comprise: a housing which is worn on a person's wrist and/or lower arm; wherein the housing further comprises a base portion; wherein the housing further comprises a movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a housing which is worn on a person's wrist and/or lower arm; wherein the housing further comprises a base portion which is a first distance from the surface of the person's wrist and/or lower arm; wherein the housing further comprises a movable portion which is movably attached to the base portion and is a second distance from the surface of the person's wrist and/or lower arm, wherein the second distance is greater than the first distance; wherein the device has a single-display configuration in which the movable portion is folded over the base portion; wherein the device has a multi-display configuration in which the movable portion is unfolded from the base portion; wherein the movable portion has a first side which faces generally away from the wrist and/or lower arm in the single-display configuration and faces generally toward the wrist and/or lower arm in the multi-display configuration; wherein the movable portion has a second side which faces generally toward the wrist and/or lower arm in the single-display configuration and faces generally away from the wrist and/or lower arm in the multi-display configuration; a first quadrilateral display (with rounded corners) on the first side of the movable portion; a second quadrilateral display (with rounded corners) on the second side of the movable portion; and a third (round corner) quadrilateral display on the base portion.

In another embodiment, a wrist-worn computing device with a multi-configuration display can comprise: a housing which is worn on a person's wrist and/or lower arm; wherein the housing further comprises a lower base portion; wherein the housing further comprises a upper movable portion which is movably attached to the base portion; wherein the device has a first configuration in which the movable portion is folded over the base portion; wherein the device has a second configuration in which the movable portion is unfolded from the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. Alternatively, a wrist-worn computing device with a multi-configuration display can comprise: a housing which is worn on the dorsal surface of a person's wrist and/or lower arm; wherein the housing further comprises a lower base portion; wherein the housing further comprises a upper movable portion, wherein the proximal (e.g. closer to the person's elbow) edge of the upper moveable portion is movably and/or flexibly attached to the lower base portion by a hinge, joint, strap, band, cord, or membrane; wherein the device has a single-display configuration in which the movable portion is folded over the base portion; wherein the device has a multi-display configuration in which the movable portion is unfolded from the base portion by pivoting, tilting, and/or rotating the distal (e.g. farther from the person's elbow) edge of the movable portion away from the base portion; wherein the movable portion has a first side which faces generally away from the wrist in the single-display configuration and faces generally toward the wrist and/or lower arm in the multi-display configuration; wherein the movable portion has a second side which faces generally toward the wrist and/or lower arm in the single-display configuration and faces generally away from the wrist in the multi-display configuration; a first display on the first side of the movable portion; a second display (or portion of a multi-part display) on the second side of the movable portion; and a third display (or portion of a multi-part display) on the base portion.

In an example, a wrist-worn computing device (such as a smart watch) with a multi-configuration display can comprise: a housing which is worn on a person's wrist and/or lower arm; wherein the housing further comprises a base portion which is a first distance from the surface of the person's wrist and/or lower arm and a movable portion which is a second distance from the surface of the person's wrist and/or lower arm, wherein the second distance is greater than the first distance; wherein the left-lateral edge of the moveable portion is movably attached to the base portion by a hinge, joint, strap, band, cord, or membrane, wherein lateral means perpendicular to the longitudinal axis of a person's lower arm; wherein the device has a first configuration in which the movable portion is folded over the base portion (being substantially parallel to and above the base portion); wherein the device has a second configuration in which the movable portion is unfolded from the base portion (being substantially coplanar with and adjacent to the base portion); wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion.

In another embodiment, a wrist-worn computing device (such as a smart watch) with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) in an outward and distal direction around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over the base portion (being substantially parallel to and above the base portion); wherein the device has a second configuration in which the movable portion is unfolded from the base portion (being substantially coplanar with and adjacent to the base portion); wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion.

In an example, a wrist-worn computing device with a multi-configuration display can comprise: a housing which is worn on a person's wrist and/or lower arm; wherein the housing further comprises a base portion and a movable portion; wherein the moveable portion is movably attached to the base portion (e.g. by a hinge, joint, strap, band, cord, or membrane); wherein the device has a first configuration in which the movable portion is folded over (being parallel to and on top of) the base portion; wherein the device has a second configuration in which an edge of the movable portion is unfolded (e.g. pivoted, tilted, flipped, and/or rotated) outward in a lateral direction (substantially perpendicular to the longitudinal axis of the person's lower arm) around the hinge, joint, strap, band, cord, or membrane relative to (being no longer parallel to) the base portion; wherein the movable portion has a first side which faces away from the wrist and/or lower arm in the first configuration and faces (substantially) toward the wrist and/or lower arm in the second configuration; wherein the movable portion has a second side which faces (substantially) toward the wrist and/or lower arm in the first configuration and faces away from the wrist and/or lower arm in the second configuration; a first display (or portion of a display) on the first side of the movable portion which functions as a visible display in the first configuration; a second display (or portion of a display) on the second side of the movable portion which functions as one of a plurality of visible displays in the second configuration; and a third display (or portion of a display) on the base portion which functions as one of a plurality of visible displays in the second configuration.

For example, a wrist-worn computing device with a multi-configuration display can comprise: a housing which is worn on a person's wrist and/or lower arm; wherein the housing further comprises a base portion and a movable portion; wherein the moveable portion is movably attached to the base portion; wherein the device has a first configuration in which the movable portion is folded over the base portion; wherein the device has a second configuration in which the movable portion is unfolded; wherein the movable portion has a first side which faces away from the wrist and/or lower arm in the first configuration and faces generally toward the wrist and/or lower arm in the second configuration; wherein the movable portion has a second side which faces generally toward the wrist and/or lower arm in the first configuration and faces away from the wrist and/or lower arm in the second configuration; a first display (or portion of a display) on the first side of the movable portion; a second display (or portion of a display) on the second side of the movable portion; and a third display (or portion of a display) on the base portion. In another example, a wrist-worn computing device with a multi-configuration display can comprise: a band which is worn on a person's wrist and/or lower arm; one or more displays which are attached to the band and/or to a housing on the band; wherein the one or more displays have a first configuration in which the one or more displays curve around a lateral (right or left) portion of the circumference of the band; wherein the one or more displays have a second configuration in which the one or more displays stick out in a lateral (right and/or left) manner from the band and/or the housing on the dorsal side of the band; wherein the one or more displays have a third configuration in which the one or more displays stick out in a proximal (closer to the person's elbow) and/or distal (farther from the person's elbow) manner from the band and/or the housing on the band; wherein the one or more displays are changed from their first configuration to their second configuration by detaching an end and moving (e.g. pivoting, bending, unfolding, or lifting) the one or more displays away from the circumference of the band; wherein the one or more displays are changed from their second configuration to their third configuration by rotating (the end of) the one or more displays around the band and/or around the housing on the band.

In an example, a wrist-worn computing device with a multi-configuration display can comprise: a proximal band which is worn around a person's wrist and/or lower arm; a distal band which is worn around the person's wrist and/or lower arm; wherein the proximal band and the distal band are attached to each other in a manner which allows one band to rotate relative to the other band; a first display which is attached to the proximal band; a second display which is attached to the distal band; wherein the device has a first configuration in which the first display and the second display are on different sides of the person's wrist and/or lower arm; wherein the device has a second configuration in which the first display and the second display are (aligned) on the same side of the person's wrist in order to form a (large) combined display; and wherein the device is changed from its first configuration to its second configuration by rotating one of the bands relative to the other band.

In an example, a wrist-worn computing device (such as a smart watch) with a multi-configuration display can comprise: a housing which is worn on a person's wrist and/or lower arm; wherein the housing further comprises a base portion which is a first distance from the surface of the person's wrist and/or lower arm and a movable portion which is a second distance from the surface of the person's wrist and/or lower arm, wherein the second distance is greater than the first distance; wherein the proximal edge of the moveable portion is movably attached to the base portion by a hinge, joint, strap, band, cord, or membrane, wherein proximal means closer to a person's elbow; wherein the device has a first configuration in which the movable portion is folded over the base portion (being substantially parallel to and above the base portion); wherein the device has a second configuration in which the movable portion is unfolded from the base portion (being substantially coplanar with and adjacent to the base portion); wherein the movable portion has a first side and a second side; wherein the first side faces more directly away from the wrist and/or lower arm than the second side in the first configuration; wherein the second side faces more directly away the wrist and/or lower arm than the first side in the second configuration; a first display (or portion of a display) on the first side of the movable portion; a second display (or portion of a display) on the second side of the movable portion; and a third display (or portion of a display) on the base portion.

In an example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an arcuate band, wherein the proximal display and the distal display are connected by (and nested within) the arcuate band. In a variation on this example, a wrist-worn device can be specified as having a "display screen" or just a "screen," instead of being specified as having a "display." In an example, a wrist-worn device with multiple displays can comprise: a proximal display screen and a distal display screen which are both worn on the same (ventral or dorsal) side of a person's wrist; wherein the centroid of the proximal display screen is ½" to 4" closer to the person's elbow than the centroid of the distal display screen; and an arcuate band, wherein the proximal display and the distal display are connected by (and nested within) the arcuate band.

In a variation on this example, a wrist-worn device can be specified as having a "strap," "coil," "cable," "link," "wire," or "loop," instead of just a "band." In an example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an arcuate band, strap, coil, cable, link, wire, or loop; wherein the proximal display and the distal display are connected by (and nested within) the arcuate band, strap, coil, cable, link, wire, or loop.

In a variation on this example, a device can be more precisely specified as having a band selected from the group consisting of "arcuate band," "oval or elliptical band," "convex band," "figure-eight-shaped band," "hourglass-shaped band," "sinusoidal," "S-shaped," or "serpentine band" instead of being specified as having an "arcuate band" or just a "band." In an example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an arcuate band; wherein the proximal display and the distal display are connected by (and nested within) the arcuate band; and wherein the arcuate band has a shaped selected from the group consisting of: oval or elliptical, convex, figure-eight shaped, hourglass shaped, sinusoidal, S shaped, and serpentine.

In a variation on this example, being "closer to the person's elbow" can be more precisely defined as being "closer to a cross-sectional perimeter of the person's arm around the person's elbow" or "closer to a virtual circle around the center of the person's elbow." In an example, a wrist-worn device with multiple displays can comprise: a proximal display and a distal display which are both worn on the same (ventral or dorsal) side of a person's wrist; wherein the centroid of the proximal display is ½" to 4" closer to a cross-sectional perimeter of the person's arm around the person's elbow than the centroid of the distal display; and an arcuate band, wherein the proximal display and the distal display are connected by (and nested within) the arcuate band. In an example, a wrist-worn device with multiple displays can comprise: a proximal display and a distal display which are both worn on the same (ventral or dorsal) side of a person's wrist; wherein the centroid of the proximal display is ½" to 4" closer to a virtual circle around the center of the person's elbow than the centroid of the distal display; and an arcuate band, wherein the proximal display and the distal display are connected by (and nested within) the arcuate band.

In a variation on this example, a device can be specified relative to a person's "wrist and/or arm," instead being specified relative to the person's "wrist." In an example, a wrist-worn device with multiple displays can comprise: a proximal display and a distal display which are both worn on the same (ventral or dorsal) side of a person's wrist and/or arm; wherein the centroid of the proximal display is ½" to 4" closer to the person's elbow than the centroid of the distal display; and an arcuate band, wherein the proximal display and the distal display are connected by (and nested within) the arcuate band.

In an variation on this example, displays can differ in one or more respects selected from the group consisting of: angular range of locations from which information displayed can be seen; display (screen) shape; display (screen) size; display on continuously vs. display activated by an incoming communication; display on continuously vs. display activated by data from a biometric or environmental sensor; display resolution level; display functions primarily as a human-to-computer interface (input) vs. a computer-to-human interface (output); light spectral frequency and/or spectral frequency range of information displayed; privacy or confidentiality level of information displayed; and rotational or angular orientation of information displayed.

In an example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and wherein the proximal display and the distal display differ in one or more respects selected from the group consisting of: angular range of locations from which information displayed can be seen; display (screen) shape; display (screen) size; display on continuously vs. display activated by an incoming communication; display on continuously vs. display activated by data from a biometric or environmental sensor; display resolution level; display functions primarily as a human-to-computer interface (input) vs. a computer-to-human interface (output); light spectral frequency and/or spectral frequency range of information displayed; privacy or confidentiality level of information displayed; and rotational or angular orientation of information displayed.

In an example, a wrist-worn device with multiple displays can comprise: a bifurcating band which is worn around a person's wrist; wherein the bifurcating band has proximal and distal branches on a selected (ventral or dorsal) side of a person's wrist; a proximal display and a distal display which are both worn on the selected side of the person's wrist; wherein the centroid of the proximal display is ½" to 4" closer to the person's elbow than the centroid of the distal display; wherein the proximal display is connected to the proximal branch of the bifurcating band and the distal display is connected to the distal branch of the bifurcating band.

In an example, a wrist-worn device with multiple displays can comprise: a bifurcating band which is worn around a person's wrist; wherein the bifurcating band splits into proximal and distal branches on a selected (ventral or dorsal) side of a person's wrist; a proximal display and a distal display which are both worn on the selected side of the person's wrist; wherein the centroid of the proximal display is ½" to 4" closer to the person's elbow than the centroid of the distal display; wherein the proximal display is connected to the proximal branch of the bifurcating band and the distal display is connected to the distal branch of the bifurcating band.

In an example, a wrist-worn device with multiple displays can comprise: a proximal band and a distal band around a person's wrist; wherein the proximal band and the distal band are connected to each other on the lateral (right and left) sides of the person's wrist; and a proximal display and a distal display which are both worn on the same (ventral or dorsal) side of the person's wrist; wherein the centroid of the proximal display is ½" to 4" closer to the person's elbow than the centroid of the distal display; wherein the proximal display is connected to the proximal band and the distal display is connected to the distal band.

In an example, a wrist-worn device with multiple displays can comprise: a proximal band and a distal band around a person's wrist; wherein the proximal band and the distal band are connected to each other on a selected (ventral or dorsal) side of the person's wrist; and a proximal display and a distal display which are both worn on the selected side of the person's wrist; wherein the centroid of the proximal display is ½" to 4" closer to the person's elbow than the centroid of the distal display; wherein the proximal display is connected to the proximal band and the distal display is connected to the distal band.

In an example, a wrist-worn device with multiple displays can comprise: a first display worn on a first (ventral or dorsal) side of a person's wrist; and a second display worn on a second (dorsal or ventral) side of the person's wrist; wherein the second side is opposite the first side; wherein the first display and the second display differ in one or more respects selected from the group consisting of: angular range of locations from which information displayed can be seen; display (screen) shape; display (screen) size; display on continuously vs. display activated by an incoming communication; display on continuously vs. display activated by data from a biometric or environmental sensor; display resolution level; display functions primarily as a human-to-computer interface (input) vs. a computer-to-human interface (output); light spectral frequency and/or spectral frequency range of information displayed; privacy or confidentiality level of information displayed; and rotational or angular orientation of information displayed.

In an example, a wrist-worn device with multiple displays can comprise: a band around a person's wrist which bifurcates on a selected (ventral or dorsal) side of the person's wrist; a proximal display and distal display on the selected side of the person's wrist; wherein the centroid of the proximal display is ½" to 4" closer to the person's elbow than the centroid of the distal display; and wherein the proximal display is visible from a first range of incidence angles and the distal display is visible from a second range of incidence angles. In another example, a wearable device with multiple displays can comprise: a band around a person's wrist; a proximal display and a distal display which are both worn on the same (ventral or dorsal) side of the person's wrist; wherein the centroid of the proximal display is ½" to 4" closer to the person's elbow than the centroid of the distal display; and wherein the proximal display is an analog display and the distal display is a digital display, or vice versa.

In an example, a wrist-worn device with multiple displays can comprise: a band around a person's wrist; and a proximal display and a distal display which are both worn on the same (ventral or dorsal) side of the person's wrist, wherein the centroid of the proximal display is ½" to 4" closer to the person's elbow than the centroid of the distal display, and wherein the proximal display is 20% to 200% larger than the distal display, or vice versa.

For example, a wearable device with multiple displays can comprise: a band around a person's wrist; and a proximal display and a distal display which are both worn on the same (ventral or dorsal) side of the person's wrist, wherein the centroid of the proximal display is ½" to 4" closer to the person's elbow than the centroid of the distal display, and wherein images on the proximal display are displayed with a first polarization vector and images on the distal display are displayed with a second polarization vector.

In an example, a wrist-worn device with multiple displays can comprise: a band around a person's wrist; and a proximal display and a distal display which are both worn on the same (ventral or dorsal) side of the person's wrist, wherein the centroid of the proximal display is ½" to 4" closer to the person's elbow than the centroid of the distal display, and the proximal display is an analog display and the distal display is a digital display, or vice versa. In an example, a wrist-worn device with multiple displays can comprise: a band around a person's wrist; and a proximal display and a distal display which are both worn on the same (ventral or dorsal) side of the person's wrist, wherein the centroid of the proximal display is ½" to 4" closer to the person's elbow than the centroid of the distal display, wherein information on a selected (proximal or distal) display is only visible to the person wearing the device.

For example, a wearable device with multiple displays can comprise: a band around a person's wrist; wherein the band diverges into proximal and distal branches on the ventral side of the person's wrist; a proximal display and a distal display on the ventral side of the person's wrist; wherein the proximal display is connected to the proximal branch of the band and the distal display device is connected to the distal branch of the band; and wherein proximal means closer to (and distal means farther from) a cross-sectional perimeter of the person's arm around the person's elbow. In another example, a wrist-worn device with multiple displays can comprise: a band comprising connected metal links which is worn around a person's wrist; a proximal display and a distal display on the band, wherein the proximal and distal displays are both worn on the same side (ventral or dorsal) of the person's wrist; wherein the centroid of the proximal display is ½" to 4" closer to the person's elbow than the centroid of the distal display.

In an example, a wearable device with multiple displays can comprise: a band worn around a person's wrist, wherein the band is a single band on a first side (ventral or dorsal) of the person's wrist and is bifurcated into two branches on a second side of the person's wrist, wherein the second side is opposite the first side; a proximal display and a distal display which are both worn on the second side; wherein the centroid of the proximal display is ½" to 4" closer to the person's elbow than the centroid of the distal display. Alternatively, a wrist-worn device with multiple displays can comprise: a band worn around a person's wrist, wherein the band is a single band on a first side (ventral or dorsal) of the person's wrist and is bifurcated into proximal and distal branches on a second side of the person's wrist, wherein the second side is opposite the first side; a proximal display on the middle of the proximal branch of the band on the second side and a distal display on the middle of the distal branch of the band on the second side; wherein the centroid of the proximal display is ½" to 4" closer to the person's elbow than the centroid of the distal display.

In an example, a wrist-worn device with multiple displays can comprise: a band worn around a person's wrist, wherein the band is wider on a first side (e.g. ventral or dorsal) than on a second side, wherein the second side is opposite the first side; a proximal display and a distal display which are both worn on the first side of the person's wrist; wherein the centroid of the proximal display is ½" to 4" closer to the person's elbow than the centroid of the distal display. In another example, a wearable device with multiple displays can comprise: a band worn around a person's wrist; wherein the band which bifurcates into proximal and distal branches on a selected side (ventral or dorsal) the person's wrist; wherein a central longitudinal axis of the proximal branch is ½" to 4" closer to the person's elbow than the central longitudinal axis of the distal branch; and a proximal display and distal display which are attached to the proximal and distance branches, respectively; wherein the proximal display functions primarily as a human-to-computer interface and the distal display functions primarily as a computer-to-human interface, or vice versa.

For example, a wrist-worn device with multiple displays can comprise: a bifurcating band around a person's wrist; a first display which is connected to a first branch of the bifurcating band; and a second display which is connected to a second branch of the bifurcating band. In another example, a wrist-worn device with multiple displays can comprise: a bifurcating band which is worn around a person's wrist; wherein the bifurcating band divides into two branches on a first side (ventral or dorsal) of the person's wrist and is a single band on a second side (dorsal or ventral) of the person's wrist, wherein the second side is opposite the first side; and a proximal display and a distal display on the first side of the person's wrist, wherein proximal means closer to the person's elbow and distal means farther from the person's elbow. Alternatively, a wearable device with multiple displays can comprise: a bracelet which spans between 50% and 90% of the cross-sectional perimeter of a person's wrist; and a circular proximal display and a circular distal display which are both worn on the same (ventral or dorsal) side of a person's wrist; wherein the centroid of the proximal display is ½" to 4" closer to the person's elbow than the centroid of the distal display.

In an example, a wrist-worn device with multiple displays can comprise: a bracelet which spans between 50% and 90% of the cross-sectional perimeter of a person's wrist; and a proximal display and a distal display which are both worn on the same (ventral or dorsal) side of the person's wrist, wherein the centroid of the proximal display is ½" to 4" closer to the person's elbow than the centroid of the distal display. For example, a wrist-worn device with multiple displays can comprise: a bracelet which spans between 50% and 90% of the cross-sectional perimeter of a person's wrist; and a rounded polygonal proximal display and a rounded polygonal distal display which are both worn on the same (ventral or dorsal) side of the person's wrist, wherein the centroid of the proximal display is ½" to 4" closer to the person's elbow than the centroid of the distal display.

In an example, a wearable device with multiple displays can comprise: a circular proximal display and a circular distal display which are both worn on the same (ventral or dorsal) side of a person's wrist; wherein the centroid of the proximal display is ½" to 4" closer to the person's elbow than the centroid of the distal display; and an arcuate band, wherein the proximal and distal displays are inside loops of the arcuate band. In another example, a wrist-worn device with multiple displays can comprise: a circular proximal display and a circular distal display which are both worn on the same (ventral or dorsal) side of a person's wrist; wherein the centroid of the proximal display is ½" to 4" closer to the person's elbow than the centroid of the distal display; and an arcuate band, wherein the proximal and distal displays are inside concave sections of the arcuate band.

In an example, a wrist-worn device with multiple displays can comprise: a circular proximal display and a circular distal display which are both worn on the same (ventral or dorsal) side of a person's wrist; wherein the centroid of the proximal display is ½" to 4" closer to the person's elbow than the centroid of the distal display; and an undulating band, wherein the proximal and distal displays are inside concave sections of the arcuate band. In another example, a wearable device with multiple displays can comprise: a circular proximal display and a circular distal display which are both worn on a first (ventral or dorsal) side of a person's wrist; wherein the centroid of the proximal display is ½" to 4" closer to the person's elbow than the centroid of the distal display; a first Y-shaped band, wherein bifurcated ends of the first Y-shaped band connect to the right sides of the proximal and distal displays, respectively; a second Y-shaped band, wherein bifurcated ends of the second Y-shaped band connect to the left sides of the proximal and distal displays, respectively; and wherein the non-bifurcated ends of the first and second Y-shaped bands connect (e.g. buckle, clip, or snap) to each other a second side of the person's wrist, wherein the second side is opposite the first side.

For example, a wrist-worn device with multiple displays can comprise: a circular proximal display and a circular distal display which are both worn on a first (ventral or dorsal) side of a person's wrist; wherein the centroid of the proximal display is ½" to 4" closer to the person's elbow than the centroid of the distal display; a first Y-shaped band, wherein bifurcated ends of the first Y-shaped band connect to the right sides of the proximal and distal displays, respectively; a second Y-shaped band, wherein bifurcated ends of the second Y-shaped band connect to the left sides of the proximal and distal displays, respectively; wherein the non-bifurcated ends of the first and second Y-shaped bands connect (e.g. buckle, clip, or snap) to each other a second side of the person's wrist, wherein the second side is opposite the first side; and wherein the proximal and distal displays are connected to each other on the first side of the person's wrist by a flexible band, strip, membrane, joint, or hinge. Alternatively, a wearable device with multiple displays can comprise: a circular proximal display and a circular distal display which are both worn on a first (ventral or dorsal) side of a person's wrist; wherein the centroid of the proximal display is ½" to 4" closer to the person's elbow than the centroid of the distal display; a first Y-shaped band, wherein bifurcated ends of the first Y-shaped band connect to the right sides of the proximal and distal displays, respectively; a second Y-shaped band, wherein bifurcated ends of the second Y-shaped band connect to the left sides of the proximal and distal displays, respectively; wherein the non-bifurcated ends of the first and second Y-shaped bands connect (e.g. buckle, clip, or snap) to each other a second side of the person's wrist, wherein the second side is opposite the first side; and wherein the proximal and distal displays are connected to each other on the first side of the person's wrist by a flexible piece of fabric.

In an example, a wrist-worn device with multiple displays can comprise: a circular proximal display and a circular distal display which are both worn on a first (ventral or dorsal) side of a person's wrist; wherein the centroid of the proximal display is ½" to 4" closer to the person's elbow than the centroid of the distal display; a first Y-shaped band, wherein bifurcated ends of the first Y-shaped band connect to the right sides of the proximal and distal displays, respectively; a second Y-shaped band, wherein bifurcated ends of the second Y-shaped band connect to the left sides of the proximal and distal displays, respectively; wherein the non-bifurcated ends of the first and second Y-shaped bands connect (e.g. buckle, clip, or snap) to each other a second side of the person's wrist, wherein the second side is opposite the first side; and wherein the proximal and distal displays are connected to each other on the first side of the person's wrist by a bendable hinge or joint.

For example, a wrist-worn device with multiple displays can comprise: a circular proximal display and a circular distal display which are worn on a person's wrist; wherein the centroid of the proximal display is ½" to 4" closer to the person's elbow than the centroid of the distal display; and wherein the diameter of the distal display is between 50% and 300% larger than the diameter of the proximal display, or vice versa.

In an example, a system for connecting two wrist-worn devices can comprise: a connecting link which is worn on a person's wrist; wherein a first (proximal or distal) portion of the link has an opening into which a first (type of) wrist-worn device (selected from the group consisting of smart watch, fitness band, and biometric sensor band) is inserted; and wherein a second (distal or proximal) portion of the link has an opening into which a second (type of) wrist-worn device (selected from the group consisting of smart watch, fitness band, and biometric sensor band) is inserted. In another example, a system for connecting two wrist-worn devices can comprise: a connecting link which is worn on a person's wrist; wherein the connecting link has a proximal portion to which a band of a first (type of) wrist-worn device is attached and a distal portion to which a band of a second (type of) wrist-worn device is attached.

In an example, a system for connecting two wrist-worn devices can comprise: a connecting link which is worn on a right or left side of a person's wrist; wherein a band of a first (type of) wrist-worn device is attached to the proximal end of the link and a band of a second (type of) wrist-worn device is attached to the distal end of the link. In another example, a system for connecting two wrist-worn devices can comprise: a connecting link which is worn on a right or left side of a person's wrist; wherein a first (type of) wrist-worn device is attached to a proximal portion of the link and a second (type of) wrist-worn device is attached to a distal portion of the link.

For example, a system for connecting two wrist-worn devices can comprise: a connecting link which is worn on a selected side (e.g. right, left, ventral, or dorsal) of a person's wrist; wherein a first (type of) wrist-worn device is inserted into a proximal portion of the link and a second (type of) wrist-worn device is inserted into a distal portion of the link. Alternatively, a system for connecting two wrist-worn devices can comprise: a connecting link which is worn on the ventral or dorsal side of a person's wrist; wherein a display of a first (type of) wrist-worn device is attached to a proximal portion of the link and a display of a second (type of) wrist-worn device is attached to a distal portion of the link.

In an example, a system for connecting two wrist-worn devices can comprise: a connecting link which is worn on the ventral or dorsal side of a person's wrist; wherein an band of a first (type of) wrist-worn device is attached to a proximal portion of the link and an band of a second (type of) wrist-worn device is attached to a distal portion of the link. In another example, a system for connecting two wrist-worn devices can comprise: a connecting link which is worn on the ventral or dorsal side of a person's wrist; wherein an electronics housing of a first (type of) wrist-worn device is attached to a proximal portion of the link and an electronics housing of a second (type of) wrist-worn device is attached to a distal portion of the link. For example, a wearable device with multiple displays can comprise: a distal display and a proximal display; wherein the centroid of the proximal display is ½" to 4" closer to the person's elbow than the centroid of the distal display; and wherein the area of the distal display is between 50% and 300% larger than the area of the proximal display.

In an example, a wrist-worn device with multiple displays can comprise: a distal display and a proximal display; wherein the centroid of the proximal display is ½" to 4" closer to the person's elbow than the centroid of the distal display; and wherein the number of image elements (e.g. pixels) in the distal display is between 50% and 300% greater than the number of image elements in the proximal display. In another example, a wrist-worn device with multiple displays can comprise: a distal display and a proximal display; wherein the centroid of the proximal display is ½" to 4" closer to the person's elbow than the centroid of the distal display; and wherein the images in the proximal display are in portion of the light spectrum which is visible to the naked eye and images in the distal display are in a portion of the light spectrum which are not visible to the naked eye, or vice versa Alternatively, a wearable device with multiple displays can comprise: a dorsal display on the dorsal side of a person's wrist; and a ventral display on the ventral side of the person's wrist; wherein content on the ventral display is more private or confidential than content on the dorsal display.

In an example, a system for connecting two wrist-worn devices can comprise: a first connecting link which is worn on a first selected side (right, left, ventral or dorsal) of a person's wrist; wherein a first (type of) wrist-worn device (selected from the group consisting of smart watch, fitness band, and biometric sensor band) is attached to a proximal portion of the first link (with a snap, clip, pin, hook, or clasp) and a second (type of) wrist-worn device (selected from the group consisting of smart watch, fitness band, and biometric sensor band) is attached to a distal portion of the first link (with a snap, clip, pin, hook, or clasp); and a second connecting link which is worn on a second selected side of a person's wrist; wherein the second side is opposite the first side; and wherein the first (type of) wrist-worn device is attached to a proximal portion of the second link (with a snap, clip, pin, hook, or clasp) and the second (type of) wrist-worn device is attached to a distal portion of the second link (with a snap, clip, pin, hook, or clasp). In another example, a system for connecting two wrist-worn devices can comprise: a first connecting link which is worn on a first selected side (right, left, ventral or dorsal) of a person's wrist; wherein a first (type of) wrist-worn device is attached to a proximal portion of the first link and a second (type of) wrist-worn device is attached to a distal portion of the first link; and a second connecting link which is worn on a second selected side of a person's wrist; wherein the second side is opposite the first side; and wherein the first (type of) wrist-worn device is attached to a proximal portion of the second link and the second (type of) wrist-worn device is attached to a distal portion of the second link.

For example, a system for connecting two wrist-worn devices can comprise: a first connecting link which is worn on a first selected side (right, left, ventral or dorsal) of a person's wrist; wherein a first (type of) wrist-worn device is attached to a proximal portion of the first link (with a snap, clip, pin, hook, or clasp) and a second (type of) wrist-worn device is attached to a distal portion of the first link (with a snap, clip, pin, hook, or clasp); and a second connecting link which is worn on a second selected side of a person's wrist; wherein the second side is opposite the first side; and wherein the first (type of) wrist-worn device is attached to a proximal portion of the second link (with a snap, clip, pin, hook, or clasp) and the second (type of) wrist-worn device is attached to a distal portion of the second link (with a snap, clip, pin, hook, or clasp). In another example, a wrist-worn device with multiple displays can comprise: a first display and a second display which are both worn on the same (ventral or dorsal) side of the person's wrist; wherein a vector connecting the centroids of the first and second displays is substantially parallel to a central longitudinal axis of the person's forearm.

In an example, a wrist-worn device with multiple displays can comprise: a first display on a first (ventral or dorsal) side of a person's wrist; and a second display on a second (dorsal or ventral) side of the person's wrist; wherein the second side is opposite the first side; and wherein the area of the first display is between 50% and 300% larger than the area of the second display. Alternatively, a wearable device with multiple displays can comprise: a first display on a first side (ventral or dorsal) of a person's wrist and a second display on a second side of the person's wrist; wherein the area second display is 25% to 300% larger than the area of the first display.

For example, a wrist-worn device with multiple displays can comprise: a first display on a first side (ventral or dorsal) of a person's wrist and a second display on a second side of the person's wrist; wherein the viewing range the second display is 30% to 90% greater than the viewing range of the first display. In another example, a wearable device with multiple displays can comprise: a first display on a selected side (ventral or dorsal) of a person's wrist which functions primarily as a human-to-computer interface (e.g. input interface); and a second display on the selected side of the person's wrist which functions primarily as a computer-to-human interface (e.g. output interface).

In an example, a wrist-worn device with multiple displays can comprise: a first display on a selected side (ventral or dorsal) of a person's wrist which functions primarily as an image display; and a second display on the selected side of the person's wrist which functions primarily as a text display. In another example, a wrist-worn device with multiple displays can comprise: a first display with a first display orientation on a first side of a person's wrist; a second display with a second display orientation on a second side the person's wrist; wherein the second side is opposite the first side; and wherein the second display orientation is perpendicular to the first display orientation.

In an example, a wearable device with multiple displays can comprise: a first display with a first image polarization which is worn on a first (ventral or dorsal) side of a person's wrist; a second display with a second image polarization which is worn on a second (dorsal or ventral) side of a person's wrist; wherein the second side is opposite the first side. Alternatively, a wrist-worn device with multiple displays can comprise: a first display with a first image resolution which is worn on a first (ventral or dorsal) side of a person's wrist; a second display with a second image resolution which is worn on a second (dorsal or ventral) side of a person's wrist; wherein the second side is opposite the first side; and wherein the second image resolution is 50% to 300% greater than the first image resolution.

For example, a wrist-worn device with multiple displays can comprise: a first Y-shaped band which spans the right side of a person's wrist; a second Y-shaped band which spans the left side of a person's wrist; wherein the non-branching ends of the first and second Y-shaped bands are connected (e.g. buckled or hooked) together on a first side (ventral or dorsal) of the person's wrist; and a proximal display and a dorsal display on a second side of the person's wrist, wherein the second side is opposite the first side; wherein the centroid of the proximal display is ½" to 4" closer to a person's elbow than the centroid of the dorsal display.

In an example, a wearable device with multiple displays can comprise: a flexible gauntlet which is worn around a person's forearm; a proximal display and a distal display which are both worn on the same side (ventral or dorsal) of the person's forearm; wherein the centroid of the proximal display is ½" to 4" closer to the person's elbow than the centroid of the distal display. In another example, a wrist-worn device with multiple displays can comprise: a flexible polymer band which is worn around a person's wrist; a proximal display and a distal display on the flexible polymer band, wherein the proximal and distal displays are both worn on the same side (ventral or dorsal) of the person's wrist; wherein the centroid of the proximal display is ½" to 4" closer to the person's elbow than the centroid of the distal display.

For example, a wrist-worn device with multiple displays can comprise: a plurality of display surfaces worn longitudinally along a (ventral or dorsal) side of a person's forearm; wherein the centroids of the display surfaces are aligned along a vector which is substantially parallel to the central longitudinal axis of the forearm; and wherein the centroids of (nearby pairs of) the displays are ¼" to 2" apart from each other. In another example, a wrist-worn device with multiple displays can comprise: a plurality of display surfaces worn longitudinally along the ventral side of a person's forearm; wherein the centroids of the display surfaces are aligned along a vector which is substantially parallel to the central longitudinal axis of the forearm.

In an example, a wrist-worn device with multiple displays can comprise: a plurality of display surfaces worn on a person's forearm; wherein the centroids of the display surfaces are aligned along a vector which is substantially parallel to the central longitudinal axis of the forearm. Alternatively, a wrist-worn device with multiple displays can comprise: a polygonal proximal display and a polygonal distal display which are both worn on the same (ventral or dorsal) side of the person's wrist; wherein the most distal edge of proximal display is tangential to the most proximal edge of the distal display.

In an example, a wearable device with multiple displays can comprise: a proximal band and a distal band around a person's wrist, wherein the proximal and distal bands are connected to each other on the lateral (right and left) sides of the person's wrist; a proximal display and a distal display which are both worn on the same side (ventral or dorsal) the person's wrist; wherein the centroid of the proximal display is ½" to 4" closer to the person's elbow than the centroid of the distal display. In another example, a wrist-worn device with multiple displays can comprise: a proximal band and a distal band around a person's wrist; wherein the proximal and distal bands are separated by at least ½" on a first (ventral or dorsal) side of the person's wrist and converge on the opposite side of the person's wrist; a proximal display and a distal display which are both on the first side; wherein the centroid of the proximal display is ½" to 4" closer to the person's elbow than the centroid of the distal display. In another example, a wearable device with multiple displays can comprise: a proximal band and a distal band around a person's wrist; wherein the proximal band is ½" to 4" closer to the person's elbow than the distal band; wherein the proximal and distal bands converge (or are connected) on the ventral side of the person's wrist; a proximal display and a distal display which are both worn on the ventral side of the person's wrist; wherein the centroid of the proximal display is ½" to 4" closer to the person's elbow than the centroid of the distal display.

For example, a wrist-worn device with multiple displays can comprise: a proximal band and a distal band around a person's wrist; wherein the proximal band is ½" to 4" closer to the person's elbow than the distal band; wherein the proximal and distal bands converge (or are connected) on the ventral side of the person's wrist; a proximal display and a distal display which are both worn on the dorsal side of the person's wrist; wherein the centroid of the proximal display is ½" to 4" closer to the person's elbow than the centroid of the distal display. Alternatively, a wrist-worn device with multiple displays can comprise: a proximal band and a distal band which are worn around a person's wrist; a circular proximal display connected to the proximal band; and a circular distal display connected to the distal band.

In an example, a wearable device with multiple displays can comprise: a proximal band and a distal band which are worn on person's wrist; wherein the proximal band is closer to the person's elbow than the distal band; wherein the proximal and distal bands converge (or connect) on a first (ventral or dorsal) side the person's wrist; a proximal display on a second side (dorsal or ventral) of the person's wrist; and a distal display on the second side of the person's wrist;

wherein the proximal display is closer to the person's elbow than the distal display. In another example, a wrist-worn device with multiple displays can comprise: a proximal band and a distal band worn around a person's wrist, wherein the proximal band is ½" to 4" closer to the person's elbow than the proximal band; a circular first display connected to the proximal band on a first (ventral or dorsal) side of the person's wrist; and a circular second display connected to the distal band on a second (dorsal or ventral) side of the person's wrist, wherein the second side is opposite the first side.

For example, a wrist-worn device with multiple displays can comprise: a proximal band and a distal band worn around a person's wrist, wherein the proximal band is ½" to 4" closer to the person's elbow than the proximal band; a first display connected to the proximal band on a first (ventral or dorsal) side of the person's wrist; and a second display connected to the distal band on the first side. In another example, a wearable device with multiple displays can comprise: a proximal band and a distal band worn around a person's wrist, wherein the proximal band is ½" to 4" closer to the person's elbow than the proximal band; a first display connected to the proximal band on a first (ventral or dorsal) side of the person's wrist; and a second display connected to the distal band on a second (dorsal or ventral) side of the person's wrist, wherein the second side is opposite the first side; and wherein the area of the first display is between 50% and 300% larger than the area of the second display.

In an example, a wrist-worn device with multiple displays can comprise: a proximal band and a distal band worn around a person's wrist, wherein the proximal band is ½" to 4" closer to the person's elbow than the proximal band; a polygonal first display connected to the proximal band on a first (ventral or dorsal) side of the person's wrist; and a polygonal second display connected to the distal band on the first side.

In an example, a wrist-worn device with multiple displays can comprise: a proximal band and a distal band worn around a person's wrist; wherein proximal means closer to (and distal means farther from) the person's elbow; wherein the proximal and distal bands converge (or are connected) on the ventral side of the person's wrist; a ventral display on the ventral side of the person's wrist; and a dorsal display on the dorsal side of the person's wrist. Alternatively, a wearable device with multiple displays can comprise: a proximal band and a distal band worn around a person's wrist; wherein proximal means closer to (and distal means farther from) the person's elbow; wherein the proximal and distal bands converge (or are connected) on the ventral side of the person's wrist; a ventral display on the ventral side of the person's wrist on the distal band; and a dorsal display on the dorsal side of the person's wrist on the proximal band.

For example, a wrist-worn device with multiple displays can comprise: a proximal band and a distal band worn around a person's wrist; wherein proximal means closer to (and distal means farther from) the person's elbow; wherein the proximal and distal bands are separated by ¼" to 4"; and a proximal display and a distal display on the dorsal side of the person's wrist; wherein the perimeters of the proximal and distal displays are separated by ¼" to 4". In another example, a wearable device with multiple displays can comprise: a proximal band and a distal band worn around a person's wrist; wherein proximal means closer to (and distal means farther from) the person's elbow; wherein the proximal and distal bands are separated by ¼" to 4"; and a proximal display and a distal display on the ventral side of the person's wrist; wherein the perimeters of the proximal and distal displays are separated by ¼" to 4".

In an example, a wrist-worn device with multiple displays can comprise: a proximal band and a distal band worn around a person's wrist; wherein proximal means closer to (and distal means farther from) the person's elbow; a first display which is connected to the proximal band; and a second display which is connected to the distal band. Alternatively, a wrist-worn device with multiple displays can comprise: a proximal band and a distal band worn around a person's wrist; wherein proximal means closer to (and distal means farther from) the person's elbow; wherein the proximal band and the distal band converge on the dorsal side of the person's wrist; a first display which is connected to the proximal band; and a second display which is connected to the distal band.

For example, a wearable device with multiple displays can comprise: a proximal band and a distal band worn around a person's wrist; wherein the proximal and distal bands converge (or are connected) on opposite sides (right and left, or ventral and dorsal) of the person's wrist; a first display on the proximal band; and a second display on the distal band. In another example, a wrist-worn device with multiple displays can comprise: a proximal band and a distal band worn around a person's wrist; wherein the proximal and distal bands converge (or are connected) on a selected side (ventral or dorsal) of the person's wrist; a proximal display and a distal display which are both worn on the selected side of the person's wrist; wherein the centroid of the proximal display is ½" to 4" closer to the person's elbow than the centroid of the distal display. In another example, a wearable device with multiple displays can comprise: a proximal band and a distal band worn around a person's wrist; wherein the proximal and distal bands converge (or are connected) on a selected (ventral or dorsal) side of the person's wrist; a proximal display on the selected side of the person's wrist; and a distal display on the selected side of the person's wrist; wherein the centroid of the proximal display is ½" to 4" closer to the person's elbow than the centroid of the distal display.

In an example, a wrist-worn device with multiple displays can comprise: a proximal band and a distal band worn around a person's wrist; wherein the proximal and distal bands converge (or are connected) on a selected side (ventral or dorsal) of the person's wrist; wherein there are openings or holes between ¼" and 2" in area in the proximal and distal bands on the selected side of the person's wrist; a proximal display on the selected side of the person's wrist; and a distal display on the selected side of the person's wrist; wherein the centroid of the proximal display is ½" to 4" closer to the person's elbow than the centroid of the distal display Alternatively, a wrist-worn device with multiple displays can comprise: a proximal band and a distal band worn around a person's wrist; wherein the proximal band is ½" to 4" closer to the person's elbow than the distal band; wherein the proximal and distal bands converge (or are connected) on a selected (ventral or dorsal) side of the person's wrist; a proximal display which is connected to the proximal band; and a distal display which is connected to the distal band; wherein the centroid of the proximal display is ½" to 4" closer to the person's elbow than the centroid of the distal display.

In an example, a wearable device with multiple displays can comprise: a proximal band and a distal band worn around a person's wrist; wherein the proximal band is ½" to 4" closer to the person's elbow than the distal band; wherein the proximal and distal bands converge (or are connected) on the dorsal side of the person's wrist; a proximal display which is connected to the proximal band; and a distal display which is connected to the distal band; wherein the centroid of the proximal display is ½" to 4" closer to the person's elbow than the centroid of the distal display. In another example, a wrist-worn device with multiple displays can comprise: a proximal band and a distal band worn around a person's wrist; wherein there are openings between ¼" and 2" in area in the proximal and distal bands on a selected (ventral or dorsal) side of the person's wrist; and wherein the proximal and distal bands converge (or are connected) on the selected side of the person's wrist; a proximal display and a distal display on the selected side of the person's wrist; wherein the centroid of the proximal display is ½" to 4" closer to the person's elbow than the centroid of the distal display.

For example, a wearable device with multiple displays can comprise: a proximal band and a distal band worn around a person's wrist; wherein there are openings greater than ¼" in area in the proximal and distal bands on a selected (ventral or dorsal) side of the person's wrist; and wherein the proximal and distal bands converge (or are connected) on the selected side of the person's wrist; a proximal display and a distal display on the selected side of the person's wrist; wherein the centroid of the proximal display is ½" to 4" closer to the person's elbow than the centroid of the distal display. Alternatively, a wrist-worn device with multiple displays can comprise: a proximal band and a distal band worn around a person's wrist; wherein there are openings in the proximal and distal bands on a selected (ventral or dorsal) side of the person's wrist; wherein the proximal and distal bands converge (or are connected) on the selected side of the person's wrist; a proximal display and a distal display on the selected side of the person's wrist; wherein the centroid of the proximal display is ½" to 4" closer to the person's elbow than the centroid of the distal display.

In an example, a wrist-worn device with multiple displays can comprise: a proximal band which is worn around a person's wrist; a distal band which is worn around the person's wrist; wherein the proximal band is closer to the person's elbow than the distal band; a proximal display which is worn on a selected (ventral or dorsal) side of the person's wrist; a distal display which is worn on the selected side of the person's wrist; wherein the proximal display is closer to the person's elbow than the distal display; wherein the proximal display is connected to the proximal band; wherein the distal display is connected to the distal band; and two connector bands on the selected side which connect the proximal display to the distal display.

For example, a wearable device with multiple displays can comprise: a proximal band which is worn around a person's wrist; a distal band which is worn around the person's wrist; wherein the proximal band is closer to the person's elbow than the distal band; a proximal display which is worn on a selected (ventral or dorsal) side of the person's wrist; a distal display which is worn on the selected side of the person's wrist; wherein the proximal display is closer to the person's elbow than the distal display; wherein the proximal display is connected to the proximal band; wherein the distal display is connected to the distal band; a first (right-side) connector band which is substantially parallel to the longitudinal axis of the person's forearm and which connects the proximal and distal displays; and a second (left-side) connector band which is substantially parallel to the longitudinal axis of the person's forearm and which connects the proximal and distal displays. In another example, a wrist-worn device with multiple displays can comprise: a proximal bracelet and a distal bracelet which each span between 50% and 90% of the circumference of a person's wrist; wherein the proximal and distal bracelets converge (or are connected) on a selected (ventral or dorsal) side of the person's wrist; and a proximal display and a distal display on the selected side of the person's wrist; wherein the centroid of the proximal display is ½" to 4" closer to the person's elbow than the centroid of the distal display.

In an example, a wearable device with multiple displays can comprise: a proximal bracelet and a distal bracelet worn around a person's wrist; wherein the proximal and distal bracelets converge (or are connected) on a first side (ventral or dorsal) of the person's wrist; a proximal display and a distal display which are both worn on a second side of the person's wrist; wherein the second side is opposite the first side; and wherein the centroid of the proximal display is ½" to 4" closer to the person's elbow than the centroid of the distal display.

In an example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an arcuate band, wherein the proximal and distal displays are within loops of the arcuate band. In another example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an arcuate band, wherein the proximal and distal displays are encircled by the arcuate band.

For example, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an oval or elliptical band which spans a portion of the proximal perimeter of the proximal display and a portion of the distal perimeter of the distal display. Alternatively, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and a figure-eight-shaped band which spans a portion of the proximal perimeter of the proximal display and a portion of the distal perimeter of the distal display.

In an example, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and a concave band which spans a portion of the proximal perimeter of the proximal display and a portion of the distal perimeter of the distal display. In another example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and a serpentine band, wherein the proximal and distal displays are nested within (and connected by) the band. Alternatively, a wrist-worn device with multiple displays can comprise: a proximal display and a distal display which are both worn on the same side (ventral or dorsal) of a person's wrist; wherein the centroid of the proximal display is ½" to 4" closer to the person's elbow than the centroid of the distal display; and a flexible polymer arcuate band, wherein the proximal and distal displays are nested within and connected by the arcuate band.

For example, a wearable device with multiple displays can comprise: a proximal display and a distal display which are both worn on the same side (ventral or dorsal) of a person's wrist; wherein the centroid of the proximal display is ½" to 4" closer to the person's elbow than the centroid of the distal display; and wherein the proximal and distal displays are connected by a flexible and/or bendable hinge. In another example, a wrist-worn device with multiple displays can comprise: a proximal display and a distal display which are both worn on the same side (ventral or dorsal) of a person's wrist; wherein the centroid of the proximal display is ½" to 4" closer to the person's elbow than the centroid of the distal display; and wherein the proximal and distal displays are connected by a flexible and/or elastic piece of fabric.

In an example, a wearable device with multiple displays can comprise: a proximal display and a distal display which are both worn on the same side (ventral or dorsal) of a person's wrist; wherein the centroid of the proximal display is ½" to 4" closer to the person's elbow than the centroid of the distal display; and wherein the proximal and distal displays are connected by a flexible and/or elastic band. In another example, a wrist-worn device with multiple displays can comprise: a proximal display and a distal display which are both worn on the same side (ventral or dorsal) of a person's wrist; wherein the centroid of the proximal display is ½" to 4" closer to the person's elbow than the centroid of the distal display; and wherein the proximal and distal displays are connected by movable interlocked chain links.

In an example, a wrist-worn device with multiple displays can comprise: a proximal display and a distal display which are both worn on the same (ventral or dorsal) side of a person's wrist; wherein the centroid of the proximal display is ½" to 4" closer to the person's elbow; and wherein the image resolution of the proximal display is greater than that of the distal display, or vice versa. Alternatively, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; wherein the distal display functions primarily as a human-to-computer interface and the proximal display functions primarily as a computer-to-human interface, or vice versa.

For example, a wearable device with multiple displays can comprise: a proximal display and a distal display which are both worn on the same (ventral or dorsal) side of a person's wrist; wherein the centroid of the proximal display is ½" to 4" closer to the person's elbow; and two straps whose ends connect to each other to hold the proximal and distal displays on the person's wrist. In another example, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and wherein the orientation of images on the distal display is rotated by 45 to 135 degrees relative to the orientation of images on the proximal display. Alternatively, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and a oval or elliptical band, wherein the proximal and distal displays are nested within (and connected by) the band.

In an example, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an figure-eight-shaped band, wherein the proximal and distal displays are nested within (and connected by) the band. In another example, a wrist-worn device with multiple displays can comprise: a proximal display and a distal display worn on a selected (ventral or dorsal) side of a person's wrist; wherein one or the two displays is on continuously and the other display is only activated when there is an incoming external communication.

In an example, a wrist-worn device with multiple displays can comprise: a proximal display and a distal display worn on a selected (ventral or dorsal) side of a person's wrist; wherein one or the two displays is on continuously and the other display is only activated at selected times. In another example, a wearable device with multiple displays can comprise: a proximal display and a distal display worn on a selected (ventral or dorsal) side of a person's wrist; wherein the centroid of the proximal display is ½" to 4" closer to the person's elbow than the centroid of the distal display; and an environmental (e.g. motion, light, sound, temperature, or GPS) sensor; wherein one of the two displays is activated based on data from the environmental sensor.

For example, a wrist-worn device with multiple displays can comprise: a proximal display and a distal display worn on a selected (ventral or dorsal) side of a person's wrist; wherein the centroid of the proximal display is ½" to 4" closer to the person's elbow than the centroid of the distal display; and a biometric (e.g. body motion, heart rate, blood pressure, glucose level, or body temperature) sensor; wherein the operation of at least one of the two displays is adjusted based on data from the biometric sensor. Alternatively, a wearable device with multiple displays can comprise: a proximal display and a distal display worn on a selected (ventral or dorsal) side of a person's wrist; wherein the centroid of the proximal display is ½" to 4" closer to the person's elbow than the centroid of the distal display; and a biometric (e.g. body motion, heart rate, blood pressure, glucose level, or body temperature) sensor; wherein one of the displays is on continuously and the other display is turned on and off automatically based on data from the biometric sensor.

In an example, a wearable system with multiple displays can comprise: a shirt sleeve or cuff; and a plurality of modular display surfaces which are removably attached to different locations on the shirt sleeve or cuff. In another example, a wearable system with multiple displays can comprise: a shirt sleeve or cuff and a plurality of modular display surfaces which are removably clipped, clasped, or pinned to different locations on the shirt sleeve or cuff.

In an example, a wrist-worn device with multiple displays can comprise: a smart watch; wherein the smart watch further comprises a circular proximal display and a circular distal display which are both worn on the same (ventral or dorsal) side of a person's wrist; and wherein the centroid of the proximal display is ½" to 4" closer to the person's elbow than the centroid of the distal display. Alternatively, a wrist-worn device with multiple displays can comprise: a tapered band around a person's wrist, wherein the band is wider on a first side of the person's wrist than on a second side of the person's wrist; a proximal display and a distal display on the first side of the person's wrist; wherein the centroid of the proximal display is ½" to 4" closer to the person's elbow than the centroid of the distal display. In another example, a wearable device with multiple displays can comprise: a tapered band around a person's wrist, wherein the band is wider on a first side of the person's wrist than on a second side of the person's wrist; a proximal display and a distal display on the first side of the person's wrist; wherein there are two holes or openings in the band to the right and left of the proximal and distal displays; wherein the centroid of the proximal display is ½" to 4" closer to the person's elbow than the centroid of the distal display.

For example, a wrist-worn device with multiple displays can comprise: a tapered band around a person's wrist; wherein the band is wider on a first (ventral or dorsal) side of the person's wrist and narrow on a second side of the person's wrist, wherein the second side is opposite the first side; and a proximal display and a distal display which are both worn on the first side; wherein the centroid of the proximal display is ½" to 4" closer to the person's elbow than the centroid of the distal display. In another example, a wearable system with multiple displays can comprise: a wearable sleeve, cuff, or gauntlet; and a plurality of modular display surfaces which are magnetically attached to different locations on the shirt sleeve, cuff, or gauntlet.

In an example, a wrist-worn device for displaying confidential information can comprise: a wrist-worn band which is worn around a person's wrist; a display on the wrist-worn band; a set of louvers, blinds, slots, lenses, or prisms on (a portion of) the display; wherein some of the information on the display is visible to anyone nearby and some of the information on the displays is only visible to the person wearing the device.

In an example, a wrist-worn device for displaying confidential information can comprise: a wrist-worn band which is worn around a person's wrist; a display on the wrist-worn band; an-tracking device which tracks the location of the person's head; a plurality of moving louvers, blinds, slots, lenses, or prisms on the display; wherein information shown on display is visible to the person wearing the device but not to other nearby people. Alternatively, a wrist-worn device for displaying confidential information can comprise: a wrist-worn band which is worn around a person's wrist; a display on the wrist-worn band; an-tracking device which tracks the location of the person's head; a plurality of moving louvers, blinds, slots, lenses, or prisms on the display; wherein the louvers, blinds, slots, lenses, or prisms move so that the person wearing the device can see information on display but other people cannot see the information.

For example, a wearable device with multiple displays can comprise: a wrist-worn band which is worn around a person's wrist; a proximal display and a distal display which are both worn on the same (ventral or dorsal) side of the person's wrist; wherein the centroid of the proximal display is ½" to 4" closer to the person's elbow than the centroid of the distal display; a set of louvers, blinds, slots, lenses, or prisms; wherein some of the information on the displays is visible to anyone nearby and some of the information on the displays is only visible to the person wearing the device. In another example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and a convex band, wherein the proximal and distal displays are nested within the convex band and connected to each other by the convex band.

In an example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and a figure-eight-shaped band, wherein the proximal and distal displays are nested within the band and connected to each other by the band. Alternatively, a wearable device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and a peanut-shaped band, wherein the proximal and distal displays are nested within the band and connected to each other by the band.

For example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and a serpentine band, wherein the proximal and distal displays are nested within the band and connected to each other by the band. In another example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and two arcuate bands, wherein the proximal and distal displays are nested within curves of the arcuate bands and connected to each other by the arcuate bands.

In an example, a wearable device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and two hourglass-shaped bands, wherein the proximal and distal displays are nested within the bands and connected to each other by the bands. In another example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and two oval bands, wherein the proximal and distal displays are nested within the oval bands and connected to each other by the oval bands.

In an example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and two sinusoidal bands, wherein the proximal and distal displays are nested within the bands and connected to each other by the bands. Alternatively, a wearable device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and two S-shaped bands, wherein the proximal and distal displays are nested within the bands and connected to each other by the bands.

For example, a wrist-worn device with multiple displays can comprise: a wrist-worn device worn by a person; a dorsal display worn on the dorsal side of the person's wrist which is on continuously and a ventral display worn on the ventral side of the person's wrist which is activated in response to an external message or communication. In another example, a wrist-worn device with multiple displays can comprise: a wrist-worn device worn by a person; a dorsal display worn on the dorsal side of the person's wrist which is on continuously and a ventral display worn on the ventral side of the person's wrist which is activated based on data from a biometric sensor.

In an example, a wearable device with multiple displays can comprise: a wrist-worn device worn by a person; a first display on a first (ventral or dorsal) side of the person's wrist which functions as a human-to-computer (touch-based) interface; and a second display on a second (dorsal or ventral) side of the person's wrist which functions as a computer-to-human (visual-based) interface, wherein the second side is opposite the first side. Alternatively, a wrist-worn device with multiple displays can comprise: a wrist-worn device worn by a person; a first display on a first (ventral or dorsal) side of the person's wrist showing a first type of content; and a second display on a second (dorsal or ventral) side of the person's wrist showing a second type of content, wherein the second side is opposite the first side.

For example, a wrist-worn device with multiple displays can comprise: a wrist-worn device worn by a person; a first display on a first (ventral or dorsal) side of the person's wrist showing confidential content; and a second display on a second (dorsal or ventral) side of the person's wrist showing non-confidential content, wherein the second side is opposite the first side. In another example, a wearable device with multiple displays can comprise: a wrist-worn device worn by a person; a motion sensor; a first display on a first (ventral or dorsal) side of the person's wrist; and a second display on a second (dorsal or ventral) side of the person's wrist, wherein the second side is opposite the first side; and a motion sensor; and wherein the first display is on continuously but the second display is activated based on data from the motion sensor.

In an example, a wrist-worn device with multiple displays can comprise: a wrist-worn device worn by a person; a ventral display worn on the ventral side of the person's wrist which is on continuously and a dorsal display worn on the dorsal side of the person's wrist which is activated in response to an external message or communication. In another example, a wrist-worn device with multiple displays can comprise: a wrist-worn device worn by a person; a ventral display worn on the ventral side of the person's wrist which is on continuously and a dorsal display worn on the dorsal side of the person's wrist which is activated based on data from a biometric sensor.

In an example, a wearable device with multiple displays can comprise: a wrist-worn device worn by a person; a ventral display, wherein the ventral display functions primarily as a human-to-computer interface (e.g. touch screen); and a dorsal display, wherein the dorsal display functions primarily as a computer-to-human interface (e.g. non-touch screen). Alternatively, a wrist-worn device with multiple displays can comprise: a wrist-worn device worn by a person; wherein the device further comprises a first display on the dorsal side of the person's wrist which is visible from a wide range of observation vectors and a second display on the ventral side of the person's wrist which is visible from a narrow range of observation vectors; wherein the information displayed by the second display is more private and/or confidential than information displayed by the first display.

For example, a wrist-worn device for displaying confidential information can comprise: a wrist-worn device worn by a person; wherein the wrist-worn device further comprises a display surface; wherein a first area of the display surface directs light beams in a wide range of directions; wherein a second area of the display surface directs light beams in a narrow range of directions; and wherein content shown in the second area is visible only (or primarily) to the person wearing the device. In another example, a wrist-worn device for displaying confidential information can comprise: a wrist-worn device worn by a person; wherein the wrist-worn device further comprises a display surface; wherein a first area of the display surface has an array of louvers, blinds, or slats which direct light beams in a wide range of directions; wherein a second area of the display surface has an array of louvers, blinds, or slats which direct light beams in a narrow range of directions; and wherein content shown in the second area is visible only (or primarily) to the person wearing the device.

In an example, a wrist-worn device for displaying confidential information can comprise: a wrist-worn device worn by a person; wherein the wrist-worn device further comprises a display surface; wherein a selected area of the display surface has an array of prisms or lenses which direct light beams in a narrow range of directions; and wherein content shown in the selected area is visible only (or primarily) to the person wearing the device. Alternatively, a wrist-worn device with multiple displays can comprise: a wrist-worn device worn by a person; wherein the wrist-worn device further comprises a first display which is visible from a first range of observation locations; and wherein the wrist-worn device further comprises a second display which is visible from a second range of observation locations; wherein the second range is less than the first range; and wherein the information displayed by the second display is more private or confidential than information displayed by the first display.

For example, a wearable device with multiple displays can comprise: a wrist-worn device; wherein the wrist-worn device further comprises a first display which is visible from a first observation vector and a second display which is visible from a second observation vector; wherein the centroid of the first display is ½" to 4" closer to the person's elbow than the centroid of the second display. In another example, a wrist-worn device with multiple displays can comprise: an environmental sensor; a proximal display and a distal display worn on a selected (ventral or dorsal) side of a person's wrist; wherein one or the two displays is on continuously and the other display is only activated based on data from the environmental sensor. In an example, a wearable system for displaying confidential information can comprise: eyewear worn by a person; a wrist-worn device worn by the person; and a display on the wrist-worn device; whereon some (or all) of the information shown on the display is displayed in a light spectral range which is not visible to a naked eye but is visible through the eyewear.

In an example, a system for connecting two wrist-worn devices can comprise: two connecting links which are worn on opposite sides (e.g. right and left, or ventral and dorsal), respectively, of a person's wrist; wherein a first (type of) wrist-worn device is attached to proximal portions of the links and a second (type of) wrist-worn device is attached to distal portions of the links. In another example, a system for connecting two wrist-worn devices can comprise: two connecting links which are worn on the right and left sides, respectively, of a person's wrist; wherein a first (type of) wrist-worn device is attached to proximal portions of the links and a second (type of) wrist-worn device is attached to distal portions of the links.

For example, a system for connecting two wrist-worn devices can comprise: two connecting links which are worn on the ventral and dorsal sides, respectively, of a person's wrist; wherein a first (type of) wrist-worn device is inserted into proximal portions of the links and a second (type of) wrist-worn device is inserted into distal portions of the links. Alternatively, a wrist-worn device with multiple displays can comprise: two displays which are both worn on the dorsal side of a person's wrist; a first Y-shaped band which connects to first lateral sides of the two displays; and a second Y-shaped band which connects to second lateral sides of the two displays; wherein the first and second Y-shaped bands connect (e.g. buckle, clip, or snap) to each other on the ventral side of the person's wrist.

In an example, a wearable device with multiple displays can comprise: two displays which are both worn on the same side (ventral or dorsal) of a person's wrist; and an array of parallel strips, louvers, or blinds which spans one of the displays and restricts the angles and/or observation positions from which content shown on that display can be seen.

For example, a wearable system with multiple displays can comprise: a band around a person's wrist; a proximal display and a distal display which are both worn on the same (ventral or dorsal) side of the person's wrist, wherein the centroid of the proximal display is ½" to 4" closer to the person's elbow than the centroid of the distal display; and eyewear worn by the person, wherein information on a selected (proximal or distal) display is only visible to the person wearing the device through the eyewear. In another example, a wrist-worn device with multiple displays can comprise: a band around a person's wrist; a ventral display on the ventral side of the person's wrist; a dorsal display on the dorsal side of the person's wrist; wherein the ventral display is an analog display and the dorsal display is a digital display, or vice versa.

In an example, a wrist-worn device with multiple displays can comprise: a band around a person's wrist; and a proximal display and a distal display which are both worn on the same (ventral or dorsal) side of the person's wrist, wherein the centroid of the proximal display is ½" to 4" closer to the person's elbow than the centroid of the distal display, and wherein images on the proximal display are visible from a first range of observation angles (or locations) and images on the distal display are visible from a second range of observation angles (or locations), wherein the first range is greater than the second range, or vice versa. Alternatively, a wearable device with multiple displays can comprise: a band around a person's wrist; and a proximal display and a distal display which are both worn on the same (ventral or dorsal) side of the person's wrist, wherein the centroid of the proximal display is ½" to 4" closer to the person's elbow than the centroid of the distal display, and wherein images on the proximal display are displayed in a first spectral range and images on the distal display are displayed in a second spectral range.

In an example, a wrist-worn device with multiple displays can comprise: a band around a person's wrist; and a proximal display and a distal display which are both worn on the same (ventral or dorsal) side of the person's wrist, wherein the centroid of the proximal display is ½" to 4" closer to the person's elbow than the centroid of the distal display, and the proximal display shows biometric information and the distal display shows environmental and/or communication related information. In another example, a wrist-worn device with multiple displays can comprise: a band around a person's wrist; wherein the band diverges into proximal and distal branches on the dorsal side of the person's wrist; a proximal display and a distal display on the dorsal side of the person's wrist; wherein the proximal display is connected to the proximal branch of the band and the distal display device is connected to the distal branch of the band; and wherein proximal means closer to (and distal means farther from) a cross-sectional perimeter of the person's arm around the person's elbow.

For example, a wearable device with multiple displays can comprise: a band worn around a person's wrist, wherein the band bifurcates into two branches on a selected side (e.g. ventral or dorsal); a proximal display and a distal display which are both worn on the selected side of the person's wrist; wherein the centroid of the proximal display is ½" to 4" closer to the person's elbow than the centroid of the distal display. In another example, a wrist-worn device with multiple displays can comprise: a band worn around a person's wrist, wherein the band is a single band on a first side (ventral or dorsal) of the person's wrist and is bifurcated into proximal and distal branches on a second side of the person's wrist, wherein the second side is opposite the first side; a circular proximal display on the proximal branch of the band and a circular distal display on the distal branch of the band; wherein the centroid of the proximal display is ½" to 4" closer to the person's elbow than the centroid of the distal display.

In an example, a wrist-worn device with multiple displays can comprise: a band worn around a person's wrist, wherein the band is a single band on a first side (ventral or dorsal) of the person's wrist and is bifurcated into proximal and distal branches on a second side of the person's wrist, wherein the second side is opposite the first side; a proximal display on the proximal branch of the band and a distal display on the distal branch of the band on the second side; wherein the centroid of the proximal display is ½" to 4" closer to the person's elbow than the centroid of the distal display. Alternatively, a wearable device with multiple displays can comprise: a band worn around a person's wrist; wherein the band which bifurcates into proximal and distal branches on a selected side (ventral or dorsal) the person's wrist; wherein a central longitudinal axis of the proximal branch is ½" to 4" closer to the person's elbow than the central longitudinal axis of the distal branch; and a proximal display and distal display which are attached to the proximal and distance branches, respectively. In another example, a wrist-worn device with multiple displays can comprise: a bifurcating band around a person's wrist, wherein the bifurcating band has two branches on a first (ventral or dorsal) side of the person's wrist and just one branch on a second (dorsal or ventral) side of the person's wrist, wherein the second side is opposite the first side; a first display on the first side of the person's wrist which is connected to the first branch; and a second display on the first side of the person's wrist which is connected to the second branch.

For example, a wrist-worn device with multiple displays can comprise: a bifurcating band around a person's wrist; a first display in the middle of a first branch of the bifurcating band; and a second display in the middle of a second branch of the bifurcating band. In another example, a wearable device with multiple displays can comprise: a bifurcating band which is worn around a person's wrist; wherein the bifurcating band divides into proximal and distal branches on a first side (ventral or dorsal) of the person's wrist and is a single band on a second side (dorsal or ventral) of the person's wrist, wherein the second side is opposite the first side; and a proximal display and a distal display which are attached to the proximal and distal branches, respectively, wherein proximal means closer to the person's elbow and distal means farther from the person's elbow.

In an example, a wrist-worn device with multiple displays can comprise: a bifurcating band which is worn around a person's wrist; wherein the bifurcating band is wider on a first side (ventral or dorsal) of the person's wrist than on a second side (dorsal or ventral) of the person's wrist, wherein the second side is opposite the first side; and a proximal display and a distal display on the first side of the person's wrist, wherein proximal means closer to the person's elbow and distal means farther from the person's elbow. Alternatively, a wrist-worn device with multiple displays can comprise: a biometric sensor; a proximal display and a distal display worn on a selected (ventral or dorsal) side of a person's wrist; wherein one or the two displays is on continuously and the other display is only activated based on data from the biometric sensor.

In an example, a wearable device with multiple displays can comprise: a bracelet which spans between 50% and 90% of the cross-sectional perimeter of a person's wrist; and a circular proximal display and a circular distal display which are both worn on the same (ventral or dorsal) side of the person's wrist, wherein the centroid of the proximal display is ½" to 4" closer to the person's elbow than the centroid of the distal display. In another example, a wrist-worn device with multiple displays can comprise: a bracelet which spans between 50% and 90% of the cross-sectional perimeter of a person's wrist; and a proximal display and a distal display which are both worn on the same (ventral or dorsal) side of the person's wrist, wherein the centroid of the proximal display is ½" to 4" closer to the person's elbow than the centroid of the distal display, and wherein the proximal display is 20% to 200% larger than the distal display, or vice versa.

For example, a wrist-worn device with multiple displays can comprise: a circular proximal display and a circular distal display which are both worn on the same (ventral or dorsal) side of a person's wrist; wherein the centroid of the proximal display is ½" to 4" closer to the person's elbow than the centroid of the distal display; and an arcuate band, wherein the proximal and distal displays are inside convex sections of the arcuate band. In another example, a wearable device with multiple displays can comprise: a circular proximal display and a circular distal display which are both worn on the same (ventral or dorsal) side of a person's wrist; wherein the centroid of the proximal display is ½" to 4" closer to the person's elbow than the centroid of the distal display; and an undulating band, wherein the proximal and distal displays are inside convex sections of the arcuate band.

In an example, a wrist-worn device with multiple displays can comprise: a circular proximal display and a circular distal display which are both worn on a first (ventral or dorsal) side of a person's wrist; wherein the centroid of the proximal display is ½" to 4" closer to the person's elbow than the centroid of the distal display; a first Y-shaped band, wherein bifurcated ends of the first Y-shaped band connect to the right sides of the proximal and distal displays, respectively; a second Y-shaped band, wherein bifurcated ends of the second Y-shaped band connect to the left sides of the proximal and distal displays, respectively; wherein the non-bifurcated ends of the first and second Y-shaped bands connect (e.g. buckle, clip, or snap) to each other a second side of the person's wrist, wherein the second side is opposite the first side; and wherein the proximal and distal displays are connected to each other on the first side of the person's wrist by a flexible arcuate band or strip.

For example, a wrist-worn device with multiple displays can comprise: a circular proximal display and a circular distal display which are both worn on a first (ventral or dorsal) side of a person's wrist; wherein the centroid of the proximal display is ½" to 4" closer to the person's elbow than the centroid of the distal display; a first Y-shaped band, wherein bifurcated ends of the first Y-shaped band connect to the right sides of the proximal and distal displays, respectively; a second Y-shaped band, wherein bifurcated ends of the second Y-shaped band connect to the left sides of the proximal and distal displays, respectively; wherein the non-bifurcated ends of the first and second Y-shaped bands connect (e.g. buckle, clip, or snap) to each other a second side of the person's wrist, wherein the second side is opposite the first side; and wherein the proximal and distal displays are connected to each other on the first side of the person's wrist by a flexible membrane. Alternatively, a wearable device with multiple displays can comprise: a circular proximal display and a circular distal display which are both worn on the same (ventral or dorsal) side of the person's wrist; wherein the most distal edge of proximal display is tangential to the most proximal edge of the distal display.

In an example, a system for connecting two wrist-worn devices can comprise: a connecting link which is worn on a person's wrist; wherein a proximal portion of the link has an opening into which the band of a first (type of) wrist-worn device (selected from the group consisting of smart watch, fitness band, and biometric sensor band) is inserted; and wherein a distal portion of the link has an opening into which the band of a second (type of) wrist-worn device (selected from the group consisting of smart watch, fitness band, and biometric sensor band) is inserted.

In an example, a system for connecting two wrist-worn devices can comprise: a connecting link which is worn on a person's wrist; wherein the connecting link has a proximal portion into which a first (type of) wrist-worn device is inserted and a distal portion to which a second (type of) wrist-worn device is inserted. In another example, a system for connecting two wrist-worn devices can comprise: a connecting link which is worn on a person's wrist; wherein the connecting link has a proximal portion into which a first (type of) wrist-worn device selected from the group consisting of smart watch, fitness band, and biometric sensor band is inserted and a distal portion to which a second (type of) wrist-worn device selected from the group consisting of smart watch, fitness band, and biometric sensor band is inserted.

For example, a system for connecting two wrist-worn devices can comprise: a connecting link which is worn on a right or left side of a person's wrist; wherein a proximal end of the link has an opening into which a proximal wrist-worn band is inserted; and wherein a distal end of the link has an opening into which a distal wrist-worn band is inserted. Alternatively, a system for connecting two wrist-worn devices can comprise: a connecting link which is worn on a selected side (e.g. right, left, ventral, or dorsal) of a person's wrist; wherein a first (type of) wrist-worn device is attached to a proximal portion of the link and a second (type of) wrist-worn device is attached to a distal portion of the link.

In an example, a system for connecting two wrist-worn devices can comprise: a connecting link which is worn on a ventral or dorsal side of a person's wrist; wherein a band of a first (type of) wrist-worn device is attached to the proximal end of the link and a band of a second (type of) wrist-worn device is attached to the distal end of the link. In another example, a system for connecting two wrist-worn devices can comprise: a connecting link which is worn on a ventral or dorsal side of a person's wrist; wherein a first (type of) wrist-worn device is attached to a proximal portion of the link and a second (type of) wrist-worn device is attached to a distal portion of the link.

For example, a system for connecting two wrist-worn devices can comprise: a connecting link which is worn on the ventral or dorsal side of a person's wrist; wherein a display of a first (type of) wrist-worn device is inserted into a proximal portion of the link and a display of a second (type of) wrist-worn device is inserted into a distal portion of the link. In another example, a system for connecting two wrist-worn devices can comprise: a connecting link which is worn on the ventral or dorsal side of a person's wrist; wherein an band of a first (type of) wrist-worn device is inserted into a proximal portion of the link and an band of a second (type of) wrist-worn device is inserted into a distal portion of the link. Alternatively, a system for connecting two wrist-worn devices can comprise: a connecting link which is worn on the ventral or dorsal side of a person's wrist; wherein an electronics housing of a first (type of) wrist-worn device is inserted into a proximal portion of the link and an electronics housing of a second (type of) wrist-worn device is inserted into a distal portion of the link.

In an example, a wrist-worn device with multiple displays can comprise: a distal display and a proximal display; wherein the centroid of the proximal display is ½" to 4" closer to the person's elbow than the centroid of the distal display; and wherein the area of the proximal display is between 50% and 300% larger than the area of the distal display. In another example, a wrist-worn device with multiple displays can comprise: a distal display and a proximal display; wherein the centroid of the proximal display is ½" to 4" closer to the person's elbow than the centroid of the distal display; and wherein the number of image elements (e.g. pixels) in the proximal display is between 50% and 300% greater than the number of image elements in the distal display. Alternatively, a wrist-worn device with multiple displays can comprise: a distal display and a proximal display; wherein the centroid of the proximal display is ½" to 4" closer to the person's elbow than the centroid of the distal display; and wherein the light spectral range of images in the proximal display is different than the light spectral range in the distal display.

In an example, a wearable device with multiple displays can comprise: a distal display and a proximal display; wherein the centroid of the proximal display is ½" to 4" closer to the person's elbow than the centroid of the distal display; and wherein images in a selected (proximal or distal) display are projected so as to be visible to the person but not visible to other people. In an example, a wrist-worn device with multiple displays can comprise: a dorsal display on the dorsal side of a person's wrist; and a ventral display on the ventral side of the person's wrist; wherein content on the ventral display is substantially oriented in parallel with the longitudinal axis of the person's forearm; and wherein content on the dorsal display is substantially oriented perpendicular to the longitudinal axis of the person's forearm.

In another example, a system for connecting two wrist-worn devices can comprise: a first connecting link which is worn on a first selected side (right, left, ventral or dorsal) of a person's wrist; wherein a first (type of) wrist-worn device is inserted into a proximal portion of the first link and a second (type of) wrist-worn device is inserted into a distal portion of the first link; and a second connecting link which is worn on a second selected side of a person's wrist; wherein the second side is opposite the first side; and wherein the first (type of) wrist-worn device is inserted into a proximal portion of the second link and the second (type of) wrist-worn device is inserted into a distal portion of the second link.

For example, a wearable device with multiple displays can comprise: a first display on a first (ventral or dorsal) side of a person's wrist; and a second display on a second (dorsal or ventral) side of the person's wrist; wherein the second side is opposite the first side; and wherein the image resolution of the first display is greater than that of the second display. In another example, a wrist-worn device with multiple displays can comprise: a first display on a first side (ventral or dorsal) of a person's wrist which functions primarily as a human-to-computer interface (e.g. input interface); and a second display on a second side (dorsal or ventral) of the person's wrist which functions primarily as a computer-to-human interface (e.g. output interface).

In an example, a wrist-worn device with multiple displays can comprise: a first display on a first side (ventral or dorsal) of a person's wrist which functions primarily as an image display; and a second display on a second side (dorsal or ventral) of the person's wrist which functions primarily as a text display. Alternatively, a wearable device with multiple displays can comprise: a first display on a first side (ventral or dorsal) of a person's wrist and a second display on a second side of the person's wrist; wherein the image resolution of the second display is 25% to 300% greater than the image resolution of the first display.

For example, a wrist-worn device with multiple displays can comprise: a first display on a first side (ventral or dorsal) of a person's wrist and a second display on a second side of the person's wrist; wherein the range or viewing angles for content on the second display is 50% to 100% greater than the range of viewing angles for content on the first display. In another example, a wearable device with multiple displays can comprise: a first display on a selected side (ventral or dorsal) of a person's wrist which functions primarily as a human-to-computer interface (e.g. input interface); and a second display on the selected side of the person's wrist which functions primarily as a computer-to-human interface (e.g. output interface).

In an example, a wrist-worn device with multiple displays can comprise: a first display which is visible from a first observation vector; and a second display which is visible from a second observation vector; wherein the information displayed by the first and second displays differs with respect to privacy and/or confidentiality. Alternatively, a wrist-worn device with multiple displays can comprise: a first display with a first display orientation on a first side of a person's wrist; a second display with a second display orientation on a second side the person's wrist; wherein the second side is opposite the first side; and wherein the second display orientation is rotated by 45 to 135 degrees relative to the first display orientation.

In an example, a wearable device with multiple displays can comprise: a first display with a first image orientation which is worn on a first (ventral or dorsal) side of a person's wrist; a second display with a second image orientation which is worn on a second (dorsal or ventral) side of a person's wrist; wherein the second side is opposite the first side; and wherein the second image orientation is rotated at least 45 degrees relative to the first image orientation. In another example, a wrist-worn device with multiple displays can comprise: a first display with a first image viewing range which is worn on a first (ventral or dorsal) side of a person's wrist; a second display with a second image viewing range which is worn on a second (dorsal or ventral) side of a person's wrist; wherein the second side is opposite the first side.

For example, a wearable device with multiple displays can comprise: a first display with a first surface area which is worn on a first (ventral or dorsal) side of a person's wrist; a second display with a second surface area which is worn on a second (dorsal or ventral) side of a person's wrist; wherein the second side is opposite the first side; and wherein the second surface area is 50% to 300% larger than the first surface area. In another example, a wrist-worn device with multiple displays can comprise: a first Y-shaped band which spans the right side of a person's wrist; a second Y-shaped band which spans the left side of a person's wrist; wherein the non-branching ends of the first and second Y-shaped bands are connected (e.g. buckled or hooked) together on a first side (ventral or dorsal) of the person's wrist; and a proximal display and a dorsal display on a second side of the person's wrist, wherein the second side is opposite the first side, wherein the right sides of the proximal and distal displays are connected to the branching ends of the first Y-shaped band, and wherein the left sides of the proximal and distal displays are connected to the branching ends of the second Y-shaped band; wherein the centroid of the proximal display is ½" to 4" closer to a person's elbow than the centroid of the dorsal display.

In an example, a wrist-worn device with multiple displays can comprise: a flexible sleeve or cuff which is worn around a person's forearm; a proximal display and a distal display which are both worn on the same side (ventral or dorsal) of the person's forearm; wherein the centroid of the proximal display is ½" to 4" closer to the person's elbow than the centroid of the distal display.

For example, a wearable device with multiple displays can comprise: a metal band which is worn around a person's wrist; a proximal display and a distal display on the metal band, wherein the proximal and distal displays are both worn on the same side (ventral or dorsal) of the person's wrist; wherein the centroid of the proximal display is ½" to 4" closer to the person's elbow than the centroid of the distal display. Alternatively, a wrist-worn device with multiple displays can comprise: a motion sensor; a proximal display and a distal display worn on a selected (ventral or dorsal) side of a person's wrist; wherein one or the two displays is on continuously and the other display is only activated based on data from the motion sensor.

In an example, a wrist-worn device with multiple displays can comprise: a plurality of display surfaces worn longitudinally along a (ventral or dorsal) side of a person's forearm; wherein the centroids of the display surfaces are aligned along a vector which is substantially parallel to the central longitudinal axis of the forearm.

In an example, a wrist-worn device with multiple displays can comprise: a plurality of display surfaces worn longitudinally along the dorsal side of a person's forearm; wherein the centroids of the display surfaces are aligned along a vector which is substantially parallel to the central longitudinal axis of the forearm. In another example, a wearable device with multiple displays can comprise: a polygonal proximal display and a polygonal distal display which are both worn on a first (ventral or dorsal) side of a person's wrist; wherein the centroid of the proximal display is ½" to 4" closer to the person's elbow than the centroid of the distal display; a first Y-shaped band, wherein bifurcated ends of the first Y-shaped band connect to the right sides of the proximal and distal displays, respectively; a second Y-shaped band, wherein bifurcated ends of the second Y-shaped band connect to the left sides of the proximal and distal displays, respectively; and wherein the non-bifurcated ends of the first and second Y-shaped bands connect (e.g. buckle, clip, or snap) to each other a second side of the person's wrist, wherein the second side is opposite the first side.

For example, a wrist-worn device with multiple displays can comprise: a proximal band and a distal band around a person's wrist, wherein the proximal and distal bands are connected to each other on a selected (ventral or dorsal) side of the person's wrist; a proximal display and a distal display which are both worn on the selected side the person's wrist; wherein the centroid of the proximal display is ½" to 4" closer to the person's elbow than the centroid of the distal display. Alternatively, a wrist-worn device with multiple displays can comprise: a proximal band and a distal band around a person's wrist; wherein the proximal and distal bands are separated by at least ½" on a first (ventral or dorsal) side of the person's wrist and converge on the opposite side of the person's wrist; a proximal display and a distal display which are both on the second side; wherein the centroid of the proximal display is ½" to 4" closer to the person's elbow than the centroid of the distal display.

In an example, a wearable device with multiple displays can comprise: a proximal band and a distal band around a person's wrist; wherein the proximal and distal bands converge (or are connected) on a first (ventral or dorsal) side of the person's wrist; a first display on the proximal band on the first side of the person's wrist; and a second display on the distal band on a second side of the person's wrist; wherein the second side is opposite the first side. In another example, a wrist-worn device with multiple displays can comprise: a proximal band and a distal band around a person's wrist; wherein the proximal band is ½" to 4" closer to the person's elbow than the distal band; wherein the proximal and distal bands converge (or are connected) on a first (ventral or dorsal) side of the person's wrist; a first display on the first side of the person's wrist which is connected to the proximal band; and a second display on a second side of the person's wrist which is connected to the distal band; wherein the second side is opposite the first side.

For example, a wearable device with multiple displays can comprise: a proximal band and a distal band around a person's wrist; wherein the proximal band is ½" to 4" closer to the person's elbow than the distal band; wherein the proximal and distal bands converge (or are connected) on the dorsal side of the person's wrist; a proximal display and a distal display which are both worn on the dorsal side of the person's wrist; wherein the centroid of the proximal display is ½" to 4" closer to the person's elbow than the centroid of the distal display. In another example, a wrist-worn device with multiple displays can comprise: a proximal band and a distal band around a person's wrist; wherein the proximal band is ½" to 4" closer to the person's elbow than the distal band; wherein the proximal and distal bands converge (or are connected) on the dorsal side of the person's wrist; a proximal display and a distal display which are both worn on the ventral side of the person's wrist; wherein the centroid of the proximal display is ½" to 4" closer to the person's elbow than the centroid of the distal display. Alternatively, a wrist-worn device with multiple displays can comprise: a proximal band and a distal band which are worn around a person's wrist; a polygonal proximal display connected to the proximal band; and a polygonal distal display connected to the distal band.

In an example, a wearable device with multiple displays can comprise: a proximal band and a distal band which are worn on person's wrist; wherein the proximal band is closer to the person's elbow than the distal band; wherein the proximal and distal bands converge (or connect) on a selected (ventral or dorsal) side the person's wrist; a proximal display on the selected side of the person's wrist; and a distal display on the selected side of the person's wrist; wherein the proximal display is closer to the person's elbow than the distal display. In another example, a wrist-worn device with multiple displays can comprise: a proximal band and a distal band worn around a person's wrist, wherein the proximal band is ½" to 4" closer to the person's elbow than the proximal band; a circular first display connected to the proximal band on a first (ventral or dorsal) side of the person's wrist; and a circular second display connected to the distal band on the first side. Alternatively, a wearable device with multiple displays can comprise: a proximal band and a distal band worn around a person's wrist, wherein the proximal band is ½" to 4" closer to the person's elbow than the proximal band; a first display connected to the proximal band on a first (ventral or dorsal) side of the person's wrist; and a second display connected to the distal band on a second (dorsal or ventral) side of the person's wrist, wherein the second side is opposite the first side.

In an example, a wrist-worn device with multiple displays can comprise: a proximal band and a distal band worn around a person's wrist, wherein the proximal band is ½" to 4" closer to the person's elbow than the proximal band; a first display connected to the proximal band on a first (ventral or dorsal) side of the person's wrist; and a second display connected to the distal band on a second (dorsal or ventral) side of the person's wrist, wherein the second side is opposite the first side; and wherein the area of the second display is between 50% and 300% larger than the area of the first display. In another example, a wrist-worn device with multiple displays can comprise: a proximal band and a distal band worn around a person's wrist, wherein the proximal band is ½" to 4" closer to the person's elbow than the proximal band; a polygonal first display connected to the proximal band on a first (ventral or dorsal) side of the person's wrist; and a polygonal second display connected to the distal band on a second (dorsal or ventral) side of the person's wrist, wherein the second side is opposite the first side.

For example, a wearable device with multiple displays can comprise: a proximal band and a distal band worn around a person's wrist; wherein proximal means closer to (and distal means farther from) the person's elbow; wherein the proximal and distal bands converge (or are connected) on the ventral side of the person's wrist; a ventral display on the ventral side of the person's wrist on the proximal band; and a dorsal display on the dorsal side of the person's wrist on the distal band. In another example, a wrist-worn device with multiple displays can comprise: a proximal band and a distal band worn around a person's wrist; wherein proximal means closer to (and distal means farther from) the person's elbow; wherein the proximal and distal bands are separated by ¼" to 4"; and a proximal display and a distal display on the dorsal side of the person's wrist; wherein the centroids of the proximal and distal displays are separated by ¼" to 4".

In an example, a wearable device with multiple displays can comprise: a proximal band and a distal band worn around a person's wrist; wherein proximal means closer to (and distal means farther from) the person's elbow; wherein the proximal and distal bands are separated by ¼" to 4"; and a proximal display and a distal display on the ventral side of the person's wrist; wherein the centroids of the proximal and distal displays are separated by ¼" to 4". Alternatively, a wrist-worn device with multiple displays can comprise: a proximal band and a distal band worn around a person's wrist; wherein proximal means closer to (and distal means farther from) the person's elbow; wherein the proximal and distal bands are parallel to each other; a first display which is connected to the proximal band; and a second display which is connected to the distal band.

For example, a wrist-worn device with multiple displays can comprise: a proximal band and a distal band worn around a person's wrist; wherein proximal means closer to (and distal means farther from) the person's elbow; wherein the proximal band and the distal band converge on the ventral side of the person's wrist; a first display which is connected to the proximal band; and a second display which is connected to the distal band. In another example, a wearable device with multiple displays can comprise: a proximal band and a distal band worn around a person's wrist; wherein proximal means closer to (and distal means farther from) the person's elbow; wherein the proximal band and the distal band converge on the right and left sides of the person's wrist; a first display which is connected to the proximal band; and a second display which is connected to the distal band.

In an example, a wrist-worn device with multiple displays can comprise: a proximal band and a distal band worn around a person's wrist; wherein the proximal and distal bands converge (or are connected) on the ventral and dorsal sides of the person's wrist; a ventral display on the ventral side of the person's wrist; and a dorsal display on the dorsal side of the person's wrist. Alternatively, a wearable device with multiple displays can comprise: a proximal band and a distal band worn around a person's wrist; wherein the proximal and distal bands converge (or are connected) on the dorsal side of the person's wrist; a proximal display on the dorsal side of the person's wrist which is on the proximal band; and a distal display on the dorsal side of the person's wrist which is on the distal band; wherein proximal means closer to (and distal means farther from) the person's elbow.

In an example, a wrist-worn device with multiple displays can comprise: a proximal band and a distal band worn around a person's wrist; wherein the proximal and distal bands converge (or are connected) on a first side (ventral or dorsal) of the person's wrist; a proximal display and a distal display which are both worn on a the second side of the person's wrist; wherein the second side is opposite the first side; and wherein the centroid of the proximal display is ½" to 4" closer to the person's elbow than the centroid of the distal display. In another example, a wrist-worn device with multiple displays can comprise: a proximal band and a distal band worn around a person's wrist; wherein the proximal and distal bands converge (or are connected) on a first (ventral or dorsal) side of the person's wrist; a proximal display on a second side of the person's wrist, wherein the second side is opposite the first side; and a distal display on the second side of the person's wrist; wherein the centroid of the proximal display is ½" to 4" closer to the person's elbow than the centroid of the distal display.

For example, a wearable device with multiple displays can comprise: a proximal band and a distal band worn around a person's wrist; wherein the proximal and distal bands converge (or are connected) on a selected side (ventral or dorsal) of the person's wrist; wherein there are larger openings or holes in the proximal and distal bands on the selected side than on other sides of the person's wrist; a proximal display on the selected side of the person's wrist; and a distal display on the selected side of the person's wrist; wherein the centroid of the proximal display is ½" to 4" closer to the person's elbow than the centroid of the distal display In another example, a wrist-worn device with multiple displays can comprise: a proximal band and a distal band worn around a person's wrist; wherein the proximal band is ½" to 4" closer to the person's elbow than the distal band; wherein the proximal and distal bands converge (or are connected) on the ventral side of the person's wrist; a proximal display which is connected to the proximal band; and a distal display which is connected to the distal band; wherein the centroid of the proximal display is ½" to 4" closer to the person's elbow than the centroid of the distal display.

In an example, a wearable device with multiple displays can comprise: a proximal band and a distal band worn around a person's wrist; wherein there are openings between ¼" and 2" in diameter in the proximal and distal bands on a selected (ventral or dorsal) side of the person's wrist; and wherein the proximal and distal bands converge (or are connected) on the selected side of the person's wrist; a proximal display and a distal display on the selected side of the person's wrist; wherein the centroid of the proximal display is ½" to 4" closer to the person's elbow than the centroid of the distal display. Alternatively, a wrist-worn device with multiple displays can comprise: a proximal band and a distal band worn around a person's wrist; wherein there are openings greater than ¼" in diameter in the proximal and distal bands on a selected (ventral or dorsal) side of the person's wrist; and wherein the proximal and distal bands converge (or are connected) on the selected side of the person's wrist; a proximal display and a distal display on the selected side of the person's wrist; wherein the centroid of the proximal display is ½" to 4" closer to the person's elbow than the centroid of the distal display.

For example, a wrist-worn device with multiple displays can comprise: a proximal band which is worn around a person's wrist; a distal band which is worn around the person's wrist; wherein the proximal band is closer to the person's elbow than the distal band; a proximal display which is worn on a selected (ventral or dorsal) side of the person's wrist; a distal display which is worn on the selected side of the person's wrist; wherein the proximal display is closer to the person's elbow than the distal display; wherein the proximal display is connected to the proximal band; wherein the distal display is connected to the distal band; a first (right-side) connector band between the proximal and distal displays; and a second (left-side) connector band between the proximal and distal displays. In another example, a wearable device with multiple displays can comprise: a proximal bracelet and a distal bracelet which are worn on a person's wrist; wherein the proximal and distal bracelets converge (or are connected) on a selected (ventral or dorsal) side of the person's wrist; and a proximal display and a distal display on the selected side of the person's wrist; wherein the centroid of the proximal display is ½" to 4" closer to the person's elbow than the centroid of the distal display. In an example, a wrist-worn device with multiple displays can comprise: a proximal bracelet and a distal bracelet worn around a person's wrist; wherein the proximal and distal bracelets converge (or are connected) on a selected side (ventral or dorsal) of the person's wrist; a proximal display and a distal display which are both worn on the selected side of the person's wrist; wherein the second side is opposite the first side; and wherein the centroid of the proximal display is ½" to 4" closer to the person's elbow than the centroid of the distal display.

In an example, a wearable device with multiple displays can comprise: a proximal display and a distal display which are both worn on a first (ventral or dorsal) side of a person's wrist; wherein the centroid of the proximal display is ½" to 4" closer to the person's elbow than the centroid of the distal display; a first Y-shaped band, wherein bifurcated ends of the first Y-shaped band connect to the right sides of the proximal and distal displays, respectively; a second Y-shaped band, wherein bifurcated ends of the second Y-shaped band connect to the left sides of the proximal and distal displays, respectively; and wherein the non-bifurcated ends of the first and second Y-shaped bands connect (e.g. buckle, clip, or snap) to each other a second side of the person's wrist, wherein the second side is opposite the first side. Alternatively, a wrist-worn device with multiple displays can comprise: a proximal display and a distal display which are both worn on the same (ventral or dorsal) side of the person's wrist; wherein the centroid of the proximal display is ½" to 4" closer to the person's elbow than the centroid of the distal display; and wherein a vector connecting the centroids of the proximal and distal displays is substantially parallel to a central longitudinal axis of the person's forearm.

For example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and two arcuate bands, wherein the proximal and distal displays are nested within and connected by the arcuate bands.

In an example, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an arcuate band, wherein the proximal and distal displays are nested within the curves of the arcuate band. In another example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an arcuate band, wherein the proximal and distal displays are linked to each other by the arcuate band. In another example, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an arcuate band, wherein the proximal and distal displays are nested within and connected by the arcuate band.

For example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an hourglass-shaped band which spans a portion of the proximal perimeter of the proximal display and a portion of the distal perimeter of the distal display. Alternatively, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and a convex band which spans a portion of the proximal perimeter of the proximal display and a portion of the distal perimeter of the distal display.

In an example, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an S-shaped band, wherein the proximal and distal displays are nested within (and connected by) the band. In another example, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an oval or elliptical band, wherein the proximal and distal displays are nested within (and connected by) the band.

In an example, a wearable device with multiple displays can comprise: a proximal display and a distal display which are both worn on the same side (ventral or dorsal) of a person's wrist; wherein the centroid of the proximal display is ½" to 4" closer to the person's elbow than the centroid of the distal display; and a metal arcuate band, wherein the proximal and distal displays are nested within and connected by the metal arcuate band. Alternatively, a wrist-worn device with multiple displays can comprise: a proximal display and a distal display which are both worn on the dorsal side of a person's wrist; wherein the centroid of the proximal display is ½" to 4" closer to the person's elbow than the centroid of the distal display; a first Y-shaped band which connects to first lateral sides of the displays; and a second Y-shaped band which connects to second lateral sides of the displays; wherein the first and second Y-shaped bands connect (e.g. buckle, clip, or snap) to each other on the ventral side of the person's wrist.

For example, a wrist-worn device with multiple displays can comprise: a proximal display and a distal display which are both worn on the same side (ventral or dorsal) of a person's wrist; wherein the centroid of the proximal display is ½" to 4" closer to the person's elbow than the centroid of the distal display; and wherein the proximal and distal displays are connected by a flexible and/or bendable joint. In another example, a wearable device with multiple displays can comprise: a proximal display and a distal display which are both worn on the same side (ventral or dorsal) of a person's wrist; wherein the centroid of the proximal display is ½" to 4" closer to the person's elbow than the centroid of the distal display; and wherein the proximal and distal displays are connected by a flexible and/or elastic strip.

In an example, a wrist-worn device with multiple displays can comprise: a proximal display and a distal display which are both worn on the same side (ventral or dorsal) of a person's wrist; wherein the centroid of the proximal display is ½" to 4" closer to the person's elbow than the centroid of the distal display; and wherein the proximal and distal displays are connected by a flexible and/or elastic membrane. In another example, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; wherein the distal display functions primarily as a human-to-computer interface and the proximal display functions primarily as a computer-to-human interface, or vice versa; and an arcuate band, wherein the proximal and distal displays are nested within (and connected by) the band.

In an example, a wrist-worn device with multiple displays can comprise: a proximal display and a distal display which are both worn on the same (ventral or dorsal) side of a person's wrist; wherein the centroid of the proximal display is ½" to 4" closer to the person's elbow; and an elastic band which holds the proximal and distal displays on the person's wrist. Alternatively, a wrist-worn device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an arcuate band, wherein the proximal and distal displays are nested within (and connected by) the band.

In an example, a wearable device with multiple displays can comprise: a proximal display and a distal display which are both worn on the same (ventral or dorsal) side of a person's wrist; wherein the centroid of the proximal display is ½" to 4" closer to the person's elbow than the centroid of the distal display; and an hourglass-shaped band, wherein the proximal and distal displays are nested within (and connected by) the band. In another example, a wrist-worn device with multiple displays can comprise: a proximal display and a distal display which are both worn on the same (ventral or dorsal) side of the person's wrist; wherein the most distal edge of proximal display is tangential to the most proximal edge of the distal display.

For example, a wearable device with multiple displays can comprise: a proximal display and a distal display which are worn on a person's wrist; wherein the centroid of the proximal display is ½" to 4" closer to the person's elbow than the centroid of the distal display; and wherein the area of the distal display is between 50% and 300% larger than the area of the proximal display, or vice versa. Alternatively, a wrist-worn device with multiple displays can comprise: a proximal display and a distal display which are worn on a person's wrist; wherein the centroid of the proximal display is ½" to 4" closer to the person's elbow than the centroid of the distal display; and wherein the proximal display shows an image of the person wearing the device and the distal display shows an image of a person with whom the person wearing the device is communicating, or vice versa.

In an example, a wrist-worn device with multiple displays can comprise: a proximal display and a distal display worn on a selected (ventral or dorsal) side of a person's wrist; wherein the centroid of the proximal display is ½" to 4" closer to the person's elbow than the centroid of the distal display; and an environmental (e.g. motion, light, sound, temperature, or GPS) sensor; wherein the operation of at least one of the two displays is adjusted based on data from the environmental sensor. In another example, a wearable device with multiple displays can comprise: a proximal display and a distal display worn on a selected (ventral or dorsal) side of a person's wrist; wherein the centroid of the proximal display is ½" to 4" closer to the person's elbow than the centroid of the distal display; and an environmental (e.g. motion, light, sound, temperature, or GPS) sensor; wherein one of the displays is on continuously and the other display is turned on and off automatically based on data from the environmental sensor.

For example, a wrist-worn device with multiple displays can comprise: a proximal display and a distal display worn on a selected (ventral or dorsal) side of a person's wrist; wherein the centroid of the proximal display is ½" to 4" closer to the person's elbow than the centroid of the distal display; and a biometric (e.g. body motion, heart rate, blood pressure, glucose level, or body temperature) sensor; wherein one of the two displays is activated based on data from the biometric sensor. In another example, a wearable device with multiple displays can comprise: a proximal display which is visible from a first range of observation positions or vectors; and a distal display which is visible from a second range of observation positions or vectors; wherein the centroid of the distal display is ½" to 4" closer to the person's elbow than the centroid of the proximal display; and wherein the information displayed by the distal and proximal displays differ with respect to level of privacy and/or confidentiality.

In an example, a wrist-worn device with multiple displays can comprise: a proximal display with a first surface area; a distal display with a second surface area; wherein the centroid of the proximal display is ½" to 4" closer to the person's elbow than the centroid of the distal display; and wherein the second surface area is 50% to 300% larger than the first surface area. Alternatively, a wrist-worn device with multiple displays can comprise: a shirt sleeve or cuff which is worn around a person's forearm; a proximal display and a distal display which are both worn on the same side (ventral or dorsal) of the person's forearm; wherein the centroid of the proximal display is ½" to 4" closer to the person's elbow than the centroid of the distal display. In an example, a wearable system with multiple displays can comprise: a shirt sleeve or cuff; and a plurality of modular display surfaces which are magnetically attached to different locations on the shirt sleeve or cuff.

For example, a wearable device with multiple displays can comprise: a tapered band around a person's wrist, wherein the band is wider on a first side of the person's wrist than on a second side of the person's wrist; a proximal display and a distal display on the first side of the person's wrist; wherein there are two holes or openings in the band on the first side of the person's wrist to the right and left of the proximal and distal displays; wherein the centroid of the proximal display is ½" to 4" closer to the person's elbow than the centroid of the distal display. In another example, a wrist-worn device with multiple displays can comprise: a ventral display which is visible from a first observation vector and a dorsal display which is visible from a second observation vector; wherein the information displayed by the ventral and dorsal displays differ with respect to privacy and/or confidentiality level.

In an example, a wearable system with multiple displays can comprise: a wearable sleeve, cuff, or gauntlet; and a plurality of modular display surfaces which are removably attached to different locations on the shirt sleeve, cuff, or gauntlet. Alternatively, a wearable system with multiple displays can comprise: a wearable sleeve, cuff, or gauntlet; and a plurality of modular display surfaces which are removably clipped, clasped, or pinned to different locations on the shirt sleeve, cuff, or gauntlet.

In an example, a wearable device with multiple displays can comprise: a wrist band which spans between 50% and 90% of the cross-sectional perimeter of a person's wrist; and a circular proximal display and a circular distal display which are both worn on the same (ventral or dorsal) side of a person's wrist; wherein the centroid of the proximal display is ½" to 4" closer to the person's elbow than the centroid of the distal display. In another example, a wrist-worn device for displaying confidential information can comprise: a wrist-worn band which is worn around a person's wrist; a display on the wrist-worn band; a plurality of louvers, blinds, slots, lenses, or prisms on selected areas of the display; wherein information shown on the selected areas of the display is visible to the person wearing the device but not to other nearby people.

In an example, a wrist-worn device for displaying confidential information can comprise: a wrist-worn band which is worn around a person's wrist; a display on the wrist-worn band; an-tracking device which tracks the location of the person's head; a plurality of moving louvers, blinds, slots, lenses, or prisms on the display; wherein the person wearing the device can see information on display but other people cannot see the information. In another example, a wrist-worn device with multiple displays can comprise: a wrist-worn band which is worn around a person's wrist; a proximal display and a distal display which are both worn on the same (ventral or dorsal) side of the person's wrist; wherein the centroid of the proximal display is ½" to 4" closer to the person's elbow than the centroid of the distal display; and wherein information on one of the two displays is visible to anyone nearby and information on the other display is only visible to the person wearing the device.

For example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and a sinusoidal band, wherein the proximal and distal displays are nested within the band and connected to each other by the band. Alternatively, a wearable device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and an arcuate band, wherein the proximal and distal displays are nested within curves of the arcuate band and connected to each other by the arcuate band.

In an example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and an hourglass-shaped band, wherein the proximal and distal displays are nested within the band and connected to each other by the band. In another example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and an oval band, wherein the proximal and distal displays are nested within the oval band and connected to each other by the oval band.

For example, a wearable device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and an S-shaped band, wherein the proximal and distal displays are nested within the band and connected to each other by the band. Alternatively, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and two convex bands, wherein the proximal and distal displays are nested within the convex bands and connected to each other by the convex bands.

In an example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and two figure-eight-shaped bands, wherein the proximal and distal displays are nested within the bands and connected to each other by the bands. In another example, a wearable device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and two peanut-shaped bands, wherein the proximal and distal displays are nested within the bands and connected to each other by the bands.

For example, a wrist-worn device with multiple displays can comprise: a wrist-worn device which is worn around a person's wrist, wherein the wrist-worn device further comprises a proximal display and a distal display which are both worn on the same (ventral or dorsal) side of the person's wrist, and wherein the centroid of the proximal display is ½" to 4" closer to the person's elbow than the centroid of the distal display; and two serpentine bands, wherein the proximal and distal displays are nested within the bands and connected to each other by the bands. In another example, a wearable device with multiple displays can comprise: a wrist-worn device worn by a person; a dorsal display worn on the dorsal side of the person's wrist which is on continuously and a ventral display worn on the ventral side of the person's wrist which is activated based on data from an environmental sensor.

In an example, a wrist-worn device with multiple displays can comprise: a wrist-worn device worn by a person; a dorsal display worn on the dorsal side of the person's wrist which is visible from a first observation vector and a ventral display worn on the ventral side of the person's wrist which is visible from a second observation vector. Alternatively, a wrist-worn device with multiple displays can comprise: a wrist-worn device worn by a person; a first display on a first (ventral or dorsal) side of the person's wrist with a first display function; and a second display on a second (dorsal or ventral) side of the person's wrist with a second display function, wherein the second side is opposite the first side.

For example, a wearable device with multiple displays can comprise: a wrist-worn device worn by a person; a first display on a first (ventral or dorsal) side of the person's wrist showing incoming content; and a second display on a second (dorsal or ventral) side of the person's wrist showing outgoing content, wherein the second side is opposite the first side. In another example, a wrist-worn device with multiple displays can comprise: a wrist-worn device worn by a person; a proximal display and a distal display worn on the same (ventral or dorsal) side of the person's wrist; and wherein the proximal display is visible from a first viewing location and the distal display is not visible from the first viewing location.

In an example, a wrist-worn device with multiple displays can comprise: a wrist-worn device worn by a person; a ventral display worn on the ventral side of the person's wrist which is on continuously and a dorsal display worn on the dorsal side of the person's wrist which is activated based on data from an environmental sensor. Alternatively, a wearable device with multiple displays can comprise: a wrist-worn device worn by a person; a ventral display worn on the ventral side of the person's wrist which is visible from a first observation vector and a dorsal display worn on the dorsal side of the person's wrist which is visible from a second observation vector.

In an example, a wrist-worn device with multiple displays can comprise: a wrist-worn device worn by a person; an analog first display on a first (ventral or dorsal) side of the person's wrist; and a digital display on a second (dorsal or ventral) side of the person's wrist showing non-confidential content, wherein the second side is opposite the first side. In another example, a wrist-worn device for displaying confidential information can comprise: a wrist-worn device worn by a person; wherein the wrist-worn device further comprises a display surface; wherein a first area of the display surface has an array of prisms or lenses which direct light beams in a wide range of directions; wherein a second area of the display surface has an array of prisms or lenses which direct light beams in a narrow range of directions; and wherein content shown in the second area is visible only (or primarily) to the person wearing the device.

In an example, a wrist-worn device for displaying confidential information can comprise: a wrist-worn device worn by a person; wherein the wrist-worn device further comprises a display surface; wherein a selected area of the display surface directs light beams in a narrow range of directions; and wherein content shown in the selected area is visible only (or primarily) to the person wearing the device. In another example, a wrist-worn device for displaying confidential information can comprise: a wrist-worn device worn by a person; wherein the wrist-worn device further comprises a display surface; wherein a selected area of the display surface has an array of louvers, blinds, or slats which direct light beams in a narrow range of directions; and wherein content shown in the selected area is visible only (or primarily) to the person wearing the device.

For example, a wrist-worn device with multiple displays can comprise: a wrist-worn device; wherein the wrist-worn device further comprises a ventral display on the ventral side of a person's wrist which is visible from a first observation vector and a dorsal display on the dorsal side of the person's wrist which is visible from a second observation vector; wherein the centroid of the first display is ½" to 4" closer to the person's elbow than the centroid of the second display. Alternatively, a wearable system for displaying confidential information can comprise: eyewear worn by a person; a wrist-worn device worn by the person; and a display on the wrist-worn device; whereon some (or all) of the information shown on the display is not seen by a naked eye but is seen through the eyewear.

In an example, a system for connecting two wrist-worn devices can comprise: two connecting links which are worn on opposite sides (e.g. right and left, or ventral and dorsal), respectively, of a person's wrist; wherein a first (type of) wrist-worn device is inserted into proximal portions of the links and a second (type of) wrist-worn device is inserted into distal portions of the links. In another example, a system for connecting two wrist-worn devices can comprise: two connecting links which are worn on the right and left sides, respectively, of a person's wrist; wherein a first (type of) wrist-worn device is inserted into proximal portions of the links and a second (type of) wrist-worn device is inserted into distal portions of the links.

For example, a system for connecting two wrist-worn devices can comprise: two connecting links which are worn on the ventral and dorsal sides, respectively, of a person's wrist; wherein a first (type of) wrist-worn device is attached to proximal portions of the links and a second (type of) wrist-worn device is attached to distal portions of the links. In an example, a wearable device with multiple displays can comprise: two displays which are both worn on the ventral and dorsal sides, respectively, of a person's wrist; and an array of parallel strips, louvers, or blinds which spans one of the displays and restricts the angles and/or observation positions from which content shown on that display can be seen.

In the above examples, a device can also be specified as having a "bangle," instead of being specified as having a "bracelet." In the above examples, a "lateral" side of a person's wrist can also be more precisely specified as a "right" or "left" side of the person's wrist. In the above examples, a device can also be specified relative to a person's "wrist and/or arm," instead being specified relative to the person's "wrist." In the above examples, being "closer to the person's elbow" can also be more precisely defined as being "closer to a cross-sectional perimeter of the person's arm around the person's elbow."

In the above examples, a device can also be specified as having a "display screen" or just a "screen," instead of being specified as having a "display surface" or just a "display." In the above examples, a device can also be more precisely specified as having a band selected from the group consisting of "arcuate band," "oval or elliptical band," "figure-eight-shaped band," "hourglass-shaped band," and "S-shaped or serpentine band" instead of being specified as having an "arcuate band" or just a "band." In the above examples, a device can also be specified as having a "strap," "coil," "cable," "link," "wire," or "loop," instead of being specified as having just a "band."

I claim:

1. A wearable computing device comprising:
a band which is configured to be worn around at least 50% of the circumference of a person's wrist and/or forearm, wherein a central longitudinal axis is defined as a line along the person's forearm from the person's elbow to the person's hand which is equidistant from the right and left sides of the person's forearm;
a dorsal display which is configured to be worn on the dorsal side of the person's wrist and/or forearm;
a left display, wherein the left display is connected by a joint or hinge to the dorsal display, and wherein the left display has: (a) a first configuration in which the left display is worn on the left side of the person's wrist and (b) a second configuration in which the left display is lifted, rotated by 90 degrees, and worn on the dorsal side of the person's wrist and/or forearm; and
a right display, wherein the right display is connected by a joint or hinge to the dorsal display, and wherein the right display has: (a) a third configuration in which the right display is worn on the right side of the person's wrist and (b) a fourth configuration in which the right display is lifted, rotated by 90 degrees, and worn on the dorsal side of the person's wrist and/or forearm;
wherein the dorsal display, the left display, and the right display are not coplanar when the left display is in the first configuration and the right display is in the third configuration; wherein the dorsal display, the left display, and the right display are coplanar when the left display is in the second configuration and the right display is in the fourth configuration; wherein the dorsal display, the left display, and the right display together are perpendicular to the central longitudinal axis when the left display is in the first configuration and the right display is in the third configuration; and wherein the dorsal display, the left display, and the right display together are parallel to the central longitudinal axis when the left display is in the second configuration and the right display is in the fourth configuration.

* * * * *